US006082185A

United States Patent [19]

Saaski

[11] Patent Number: 6,082,185

[45] Date of Patent: Jul. 4, 2000

[54] DISPOSABLE FLUIDIC CIRCUIT CARDS

[75] Inventor: Elric W. Saaski, Bothell, Wash.

[73] Assignee: Research International, Inc., Woodinville, Wash.

[21] Appl. No.: 08/900,649

[22] Filed: Jul. 25, 1997

[51] Int. Cl.[7] .......................... F16K 27/00; B01D 35/02; G01N 33/48

[52] U.S. Cl. .................... 73/64.56; 73/53.01; 73/DIG. 8; 422/68.1; 436/180

[58] Field of Search ................................ 73/64.56, 53.01, 73/DIG. 8, 61.59; 436/180; 422/68.1

[56] References Cited

U.S. PATENT DOCUMENTS

| | | | |
|---|---|---|---|
| D. 284,699 | 7/1986 | Jolley | D24/29 |
| D. 293,374 | 12/1987 | Herzberg et al. | D24/17 |
| 3,825,410 | 7/1974 | Bagshawe | 23/230 R |
| 4,152,098 | 5/1979 | Moody et al. | 417/413 |
| 4,169,125 | 9/1979 | Rodriquez et al. | 422/65 |
| 4,264,327 | 4/1981 | Blum | 23/230 B |

(List continued on next page.)

FOREIGN PATENT DOCUMENTS

| | | | |
|---|---|---|---|
| 0 134 614 | 3/1985 | European Pat. Off. | F04B 43/14 |
| 0 164 089 | 12/1985 | European Pat. Off. | B01D 46/00 |
| 0 369 997 | 5/1990 | European Pat. Off. | A61M 5/168 |
| 3917423C1 | of 0000 | Germany | F16K 1/00 |
| 25 17 786 | 12/1975 | Germany | G01N 21/26 |
| 152273 | of 0000 | Norway | G01N 21/64 |

OTHER PUBLICATIONS

Small Business Innovation Research Program, Saaski, Fiber Optic Immunoassay System For Infectious Disease Agent Detection, pp. 1–61 and cover sheet and Appendices and pp. i–ii; May 1, 1995.

International Journal of Food Microbiology, 27 (1995) pp. 129–137, Development Of A Flow Injection Analysis (FIA) Immunosensor For The Detection Of *Escherichoa coli*; Bouvrette, et al., 1995.

Analytica Chimica Acta 292 (1994) 281–295, An Automated System For Multichannel Flow–Injection Analysis; Spohn et al.

Photonics Spectra; Jan. 1987; pp. 59–60, 62, 64, 66, 68, and70; Designer's Handbook, Fiber Optic Sensors: Intensity Modulation; Krohn.

Applied Optics, vol. 26, No. 11, pp. 2181–2187, Jun. 1987, Effect Of Numerical Aperture On Signal Level In Cylindrical Waveguide Evanescent Fluorosensors; Glass et al.

(List continued on next page.)

*Primary Examiner*—Hezron Williams
*Assistant Examiner*—J. David Wiggins
*Attorney, Agent, or Firm*—Gregory W. Moravan

[57] ABSTRACT

A compact fluidic circuit card having a main body with internal sensing elements and with fluidic circuit components (FCCs) located on both its front and back surfaces. An immunoassay sensing element may be used either in the form of a optical waveguide around which the liquid test sample may flow, or a disc through which the liquid test sample may flow. The card may be made inexpensive enough to be disposable by forming its main body and all of its FCCs so that they are suitable for being integrally formed in one piece by injection molding from plastic, regardless of the number of its FCCs; and by using thin strips of adhesively attached material for the main body's cover, needle septum strip and valve membrane strip. Heat-shrink plastic may be used for the valve membranes. The strength of the heat-shrink plastic's adhesive bonds may be increased by using a corona or plasma discharge to intentionally damage the surface of the heat-shrink plastic. Cross contamination between liquids in the card may be prevented by using separating bubbles, large radius turns in the channels, and valve cavities shaped to permit the valve membranes to empty them completely when the valve is closed. Mass transfer enhancing components may be provided to increase the rate at which the target material in the liquid test sample reaches the sensing element. Either transmissive or reflective light source and photodetector pairs may be used to detect fluids and bubbles in the card; and to read information encoded on the card.

37 Claims, 12 Drawing Sheets

U.S. PATENT DOCUMENTS

| | | | |
|---|---|---|---|
| 4,447,546 | 5/1984 | Hirschfeld | 436/527 |
| 4,450,375 | 5/1984 | Siegal | 310/331 |
| 4,558,014 | 12/1985 | Hirschfeld et al. | 426/527 |
| 4,582,809 | 4/1986 | Block et al. . | |
| 4,671,938 | 6/1987 | Cook | 422/57 |
| 4,673,657 | 6/1987 | Christian | 436/501 |
| 4,704,255 | 11/1987 | Jolley | 422/101 |
| 4,708,931 | 11/1987 | Christian | 435/7 |
| 4,716,121 | 12/1987 | Block et al. | 436/514 |
| 4,756,508 | 7/1988 | Giachino et al. | 251/331 |
| 4,768,751 | 9/1988 | Giachino et al. | 251/331 |
| 4,852,967 | 8/1989 | Cook et al. | 350/96.29 |
| 4,869,282 | 9/1989 | Sittler et al. | 137/15 |
| 4,933,147 | 6/1990 | Hollar et al. | 422/64 |
| 4,956,148 | 9/1990 | Grandone | 422/64 |
| 4,999,285 | 3/1991 | Stiso | 435/7.9 |
| 5,019,047 | 5/1991 | Kriesel | 604/132 |
| 5,035,861 | 7/1991 | Grandone | 422/64 |
| 5,061,857 | 10/1991 | Thompson et al. | 250/458.1 |
| 5,075,077 | 12/1991 | Durley, III et al. | 422/56 |
| 5,100,626 | 3/1992 | Levin | 422/100 |
| 5,126,276 | 6/1992 | Fish et al. | 436/531 |
| 5,138,868 | 8/1992 | Long | 73/1 R |
| 5,141,871 | 8/1992 | Kureshy et al. | 436/47 |
| 5,162,237 | 11/1992 | Messenger et al. | 436/523 |
| 5,167,922 | 12/1992 | Long | 422/58 |
| 5,171,533 | 12/1992 | Fine et al. | 422/72 |
| 5,200,321 | 4/1993 | Kidwell | 435/7.9 |
| 5,219,526 | 6/1993 | Long | 422/64 |
| 5,223,219 | 6/1993 | Subramanian et al. | 422/55 |
| 5,230,866 | 7/1993 | Shartle et al. | 422/103 |
| 5,324,481 | 6/1994 | Dunn et al. | 422/64 |
| 5,369,007 | 11/1994 | Kidwell | 435/7.9 |
| 5,430,813 | 7/1995 | Anderson et al. | 385/12 |
| 5,449,621 | 9/1995 | Klein | 436/45 |
| 5,478,751 | 12/1995 | Oosta et al. | 436/165 |
| 5,492,674 | 2/1996 | Meserol | 422/82.08 |
| 5,559,000 | 9/1996 | Janda et al. | 435/6 |
| 5,585,011 | 12/1996 | Saaski et al. | 216/2 |
| 5,597,702 | 1/1997 | Wong et al. | 435/18 |
| 5,601,991 | 2/1997 | Oberhardt | 435/7.91 |
| 5,602,037 | 2/1997 | Ostgaard et al. | 436/69 |
| 5,606,170 | 2/1997 | Saaski et al. | 250/458.1 |
| 5,617,632 | 4/1997 | Saaski et al. | 29/890.122 |
| 5,660,728 | 8/1997 | Saaski et al. | 210/251 |
| 5,697,153 | 12/1997 | Saaski et al. | 21/890.128 |
| 5,702,618 | 12/1997 | Saaski et al. | 216/2 |
| 5,705,070 | 1/1998 | Saaski et al. | 210/446 |
| 5,839,467 | 11/1998 | Saaski et al. . | |

OTHER PUBLICATIONS

Biosensors & Bioelectronics 5 (1990) 125–135; A Fiber–Optic Biosensor Based On Fluorometric Detection Using Confined Macromolecular Nicotinamide Adenine Dinucleotide Derivatives1; Scheper.

Circuits and Devices, Nov. 1990, pp. 12–19; Fiber–Optic Sensors Make Waves In Acoustics, Control, and Navigation, Dandridge.

American Chemical Society; 1989; pp. 318–330; Design Considerations For AntibodyBased Fiber–Optic Chemical Sensors; Sepaniak et al.

Sensors And Actuators B.; 17 (1994); 113–119; Calculation Of The Angular Distribution And Waveguide Capture Efficiency Of The Light Emitted By A Fluorophore Situated At Or Adsorbed To The Waveguide Side Wall, Ratner.

Applied Spectroscopy; vol. 46 No. 6; 1992; Determination Of The Effective Depth For Double–Fiber Fluorometric Sensors; Zhu et al.

Sensors And Actuators B; 11 (1993); 73–78; Reversible Fiber–Optic Immunosensor Measurements; Astles et al.

Pollution Prevention In Industrial Processes; 1992; pp. 270–283; Development Of Fiber–Optic Immunosensors For Enviromental Analysis; Vo–Dinh.

Analytica Chimica Acta; 279 (1993) 141–147; Reusable Fiber–Optic–Based Immunosensor For Rapid Detection Of Imazethapyr Herbicide; Wong et al.

Optics And Lasers In Engineering; 3 (1982) 155–182; Development Of Fibre Optic Sensing Systems—A Review; Kyuma et al.

Cold Plasma In Materials Fabrication From Fundamentals To Applications; 1994; pp. 151–166; Grill.

Semiconductor Integrated Circuit Processing Technology; 1990; pp. 34 and 189–190; Runyan.

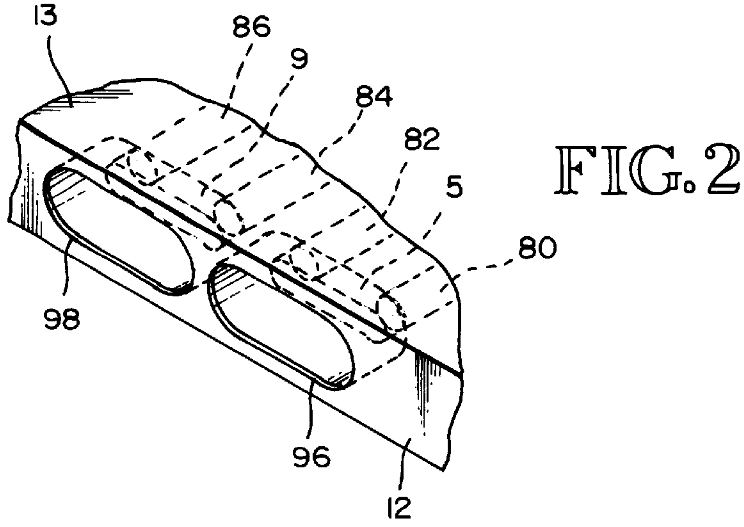
FIG. 2
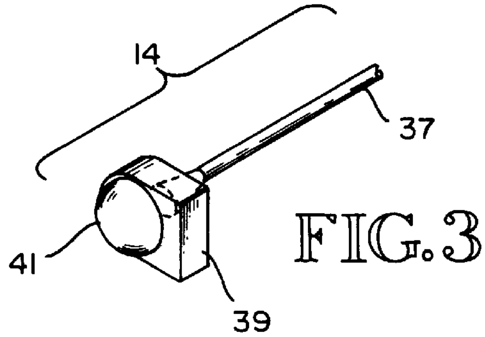
FIG. 3
FIG. 4
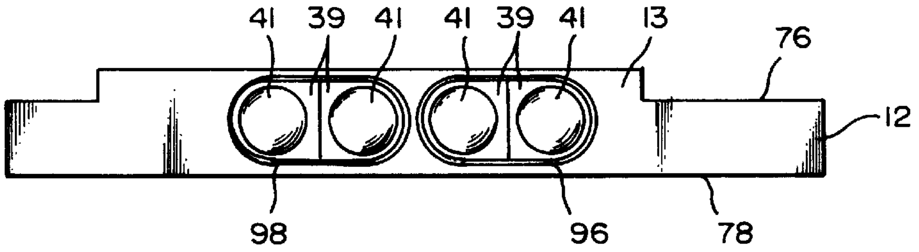
FIG. 5
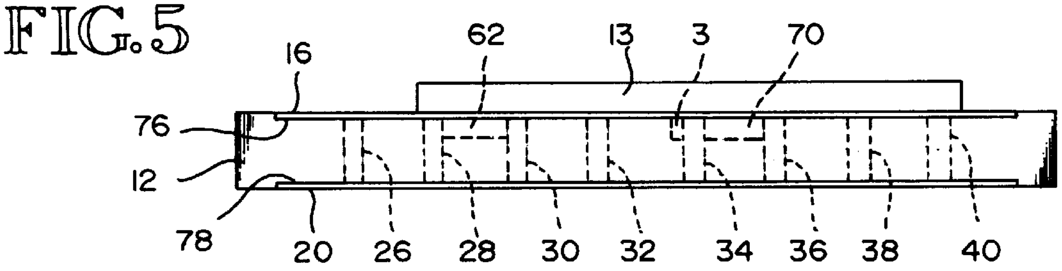

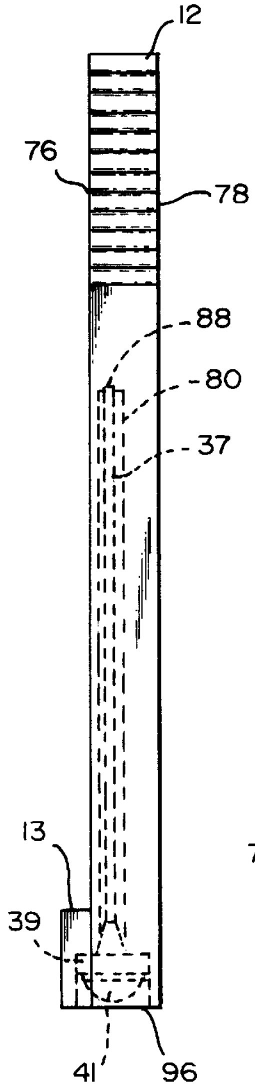
FIG. 6
FIG. 7
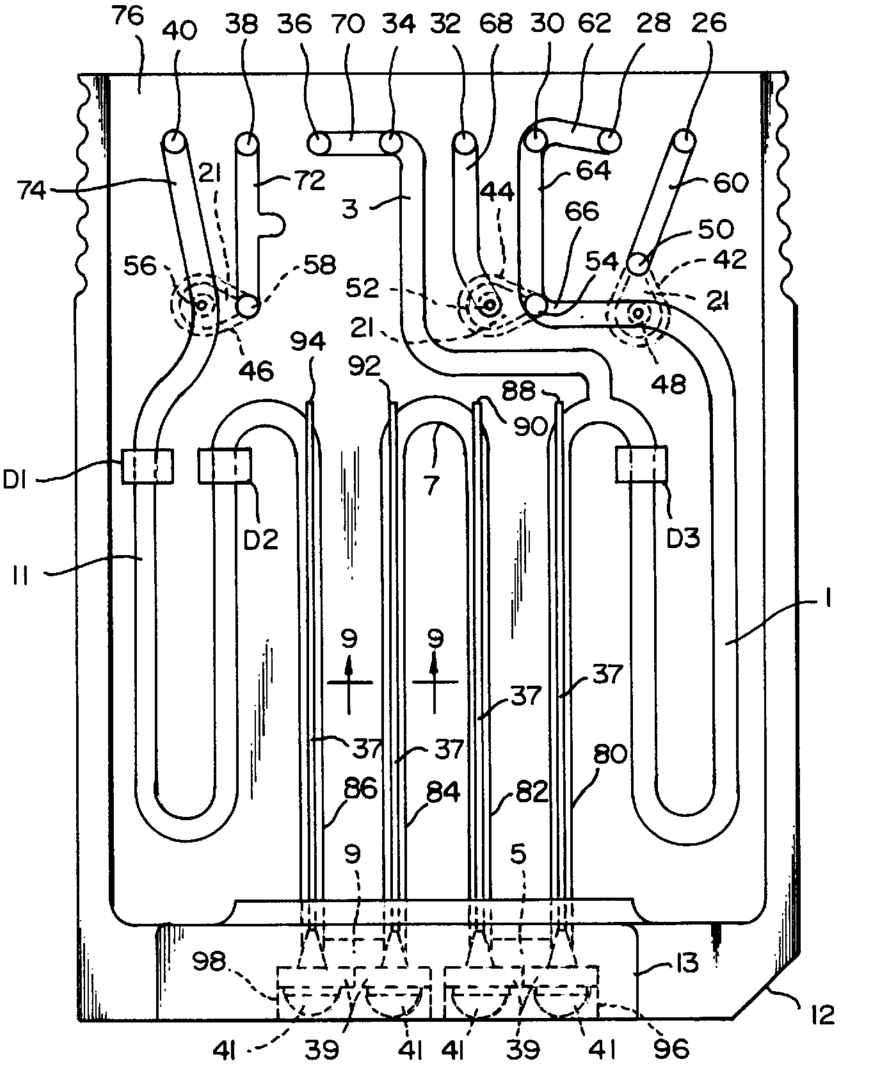

FIG.8
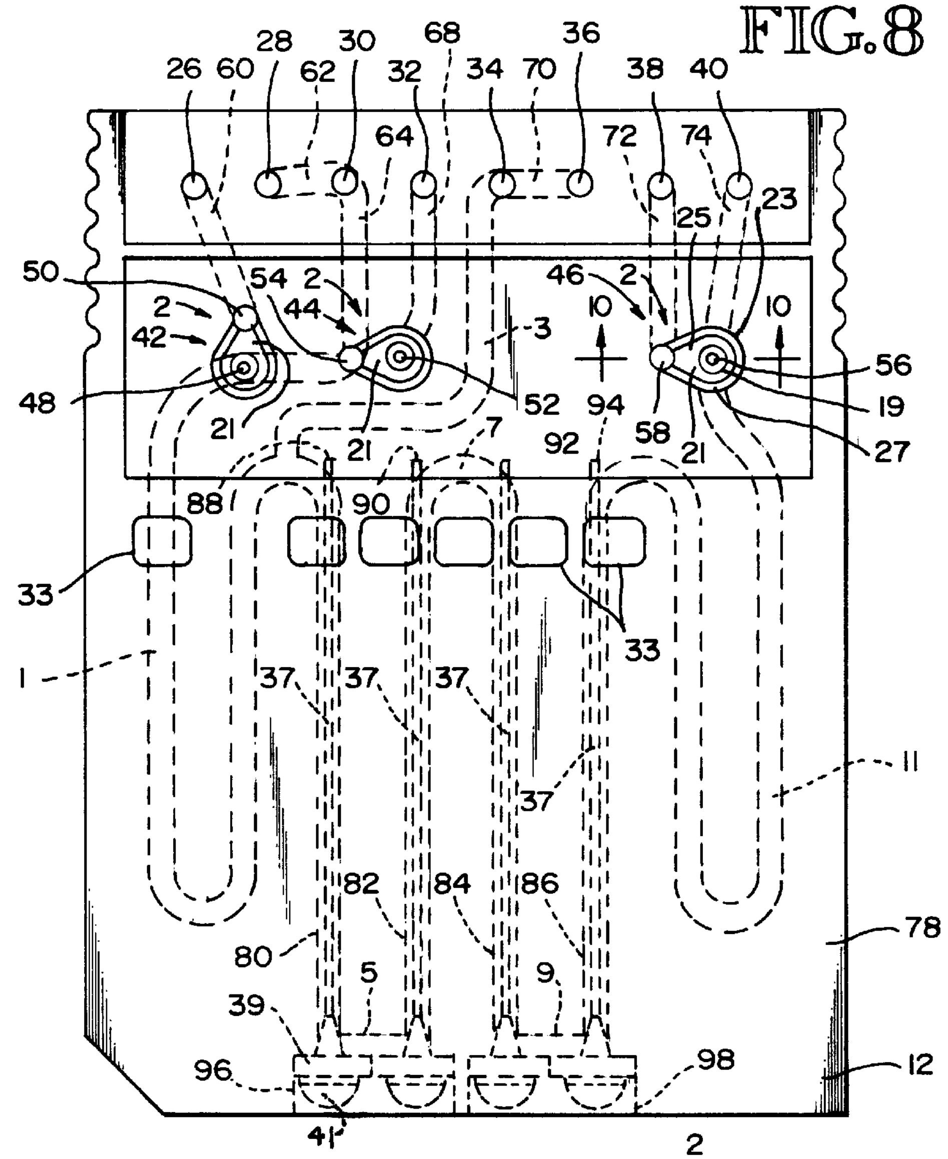
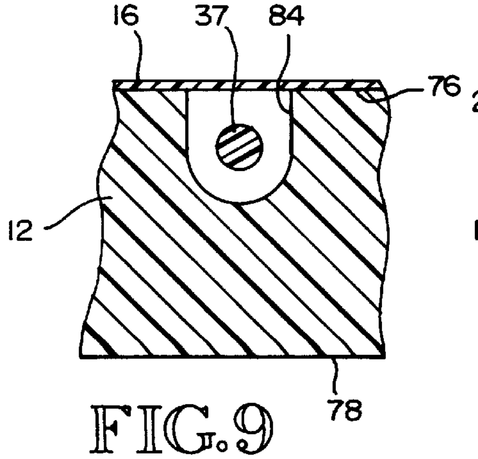
FIG.9
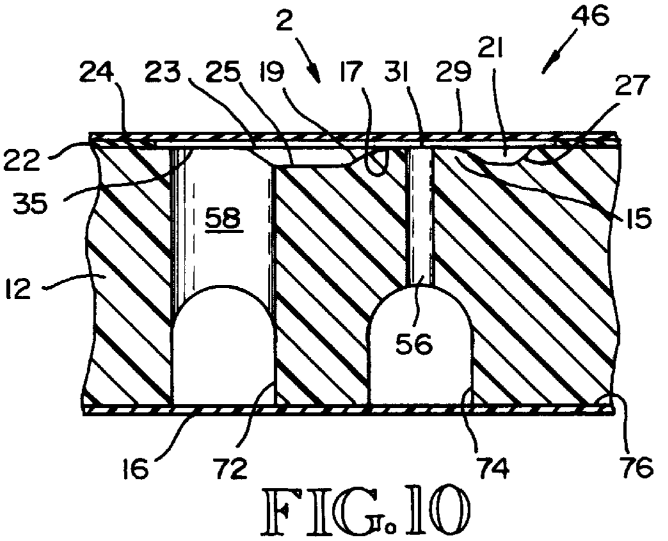
FIG.10

FIG. 10A
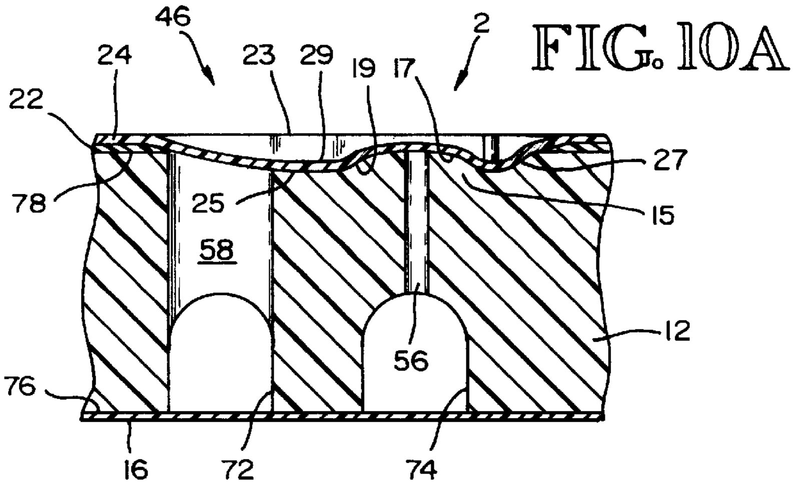
FIG. 11
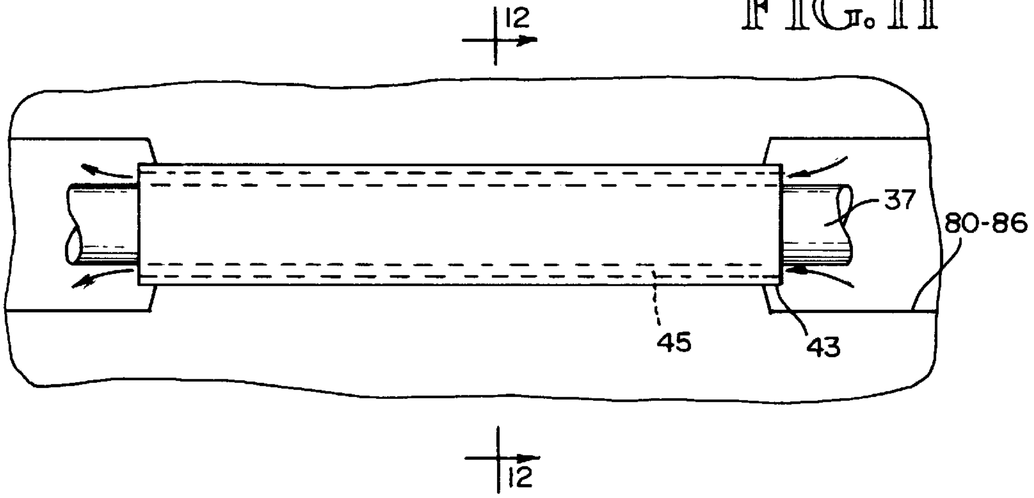
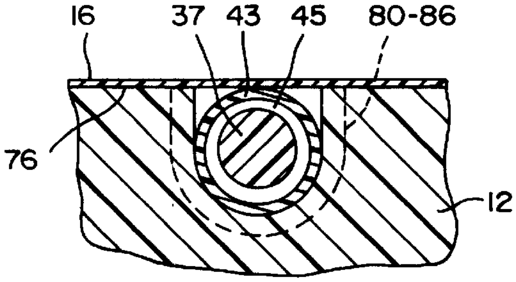
FIG. 12
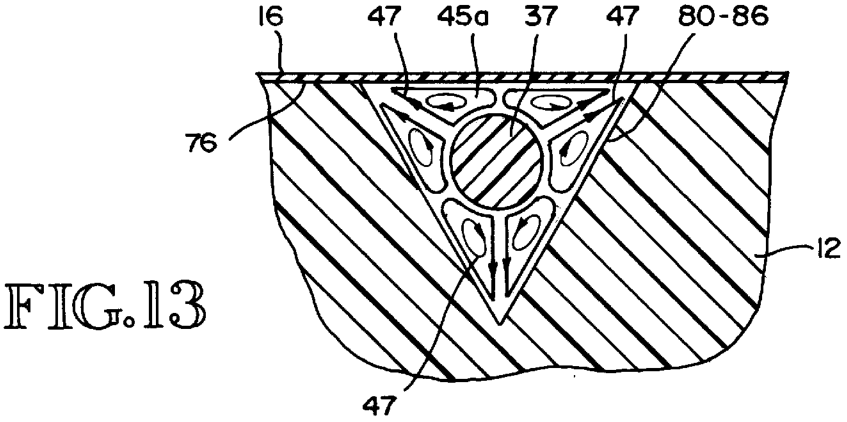
FIG. 13

FIG. 14
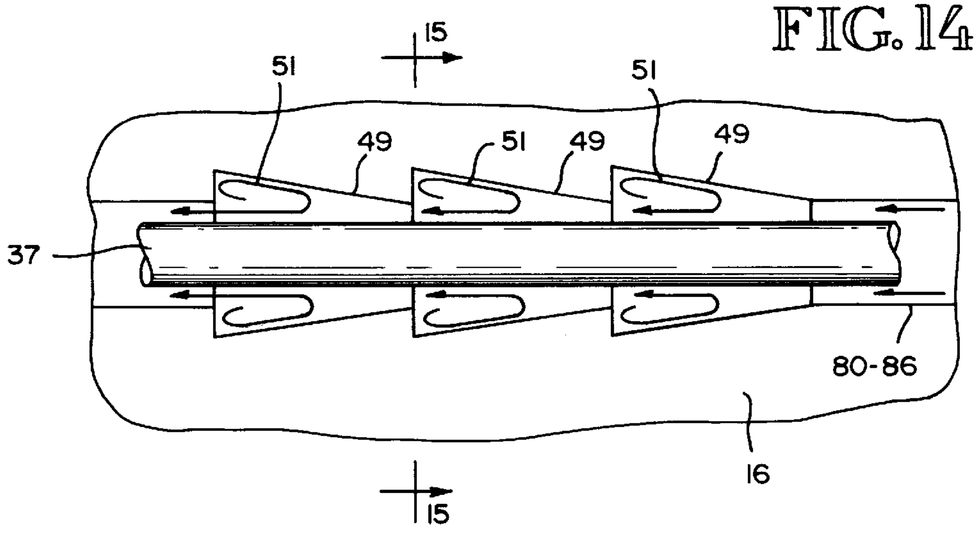
FIG. 15
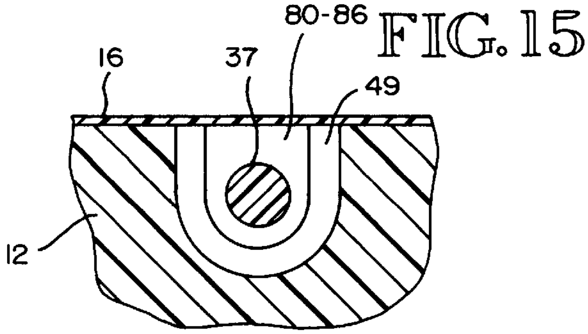
FIG. 16
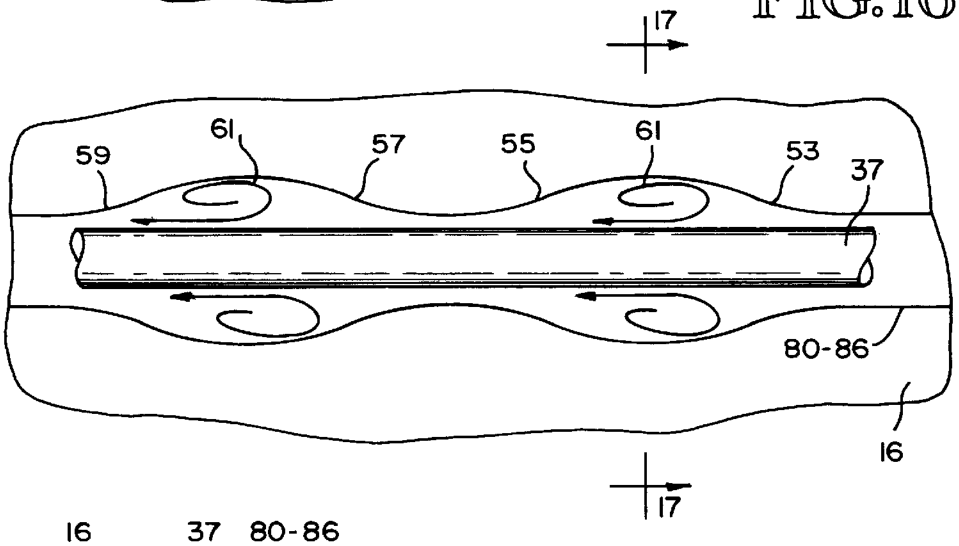
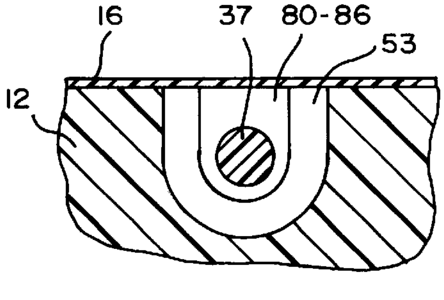
FIG. 17

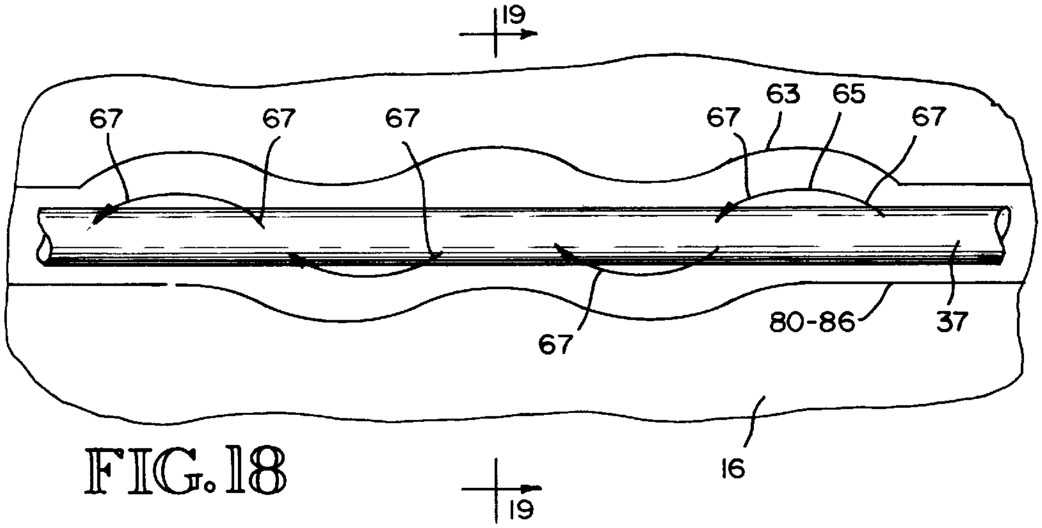
FIG. 18
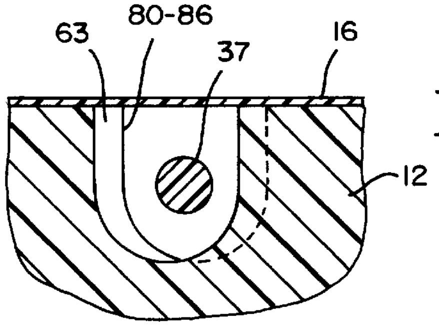
FIG. 19
FIG. 20
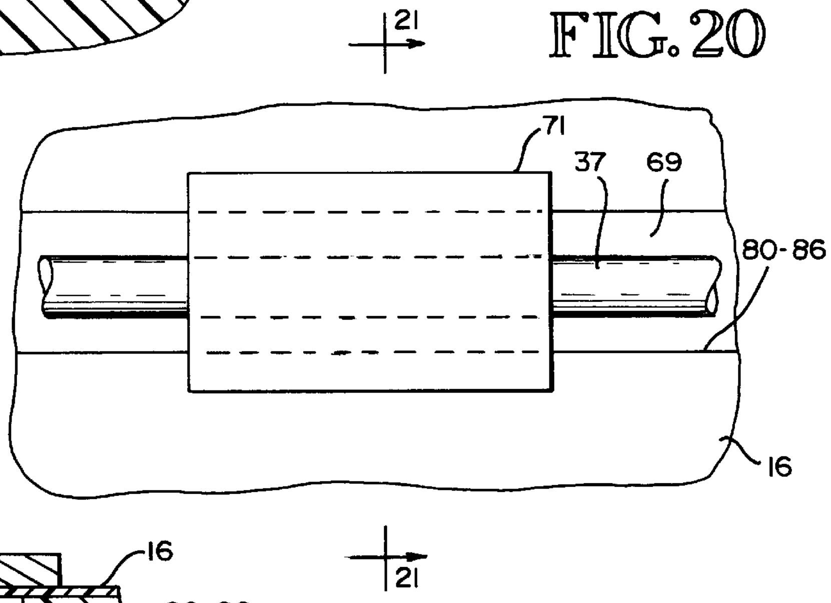
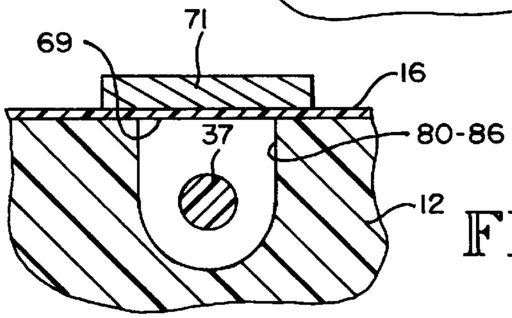
FIG. 21

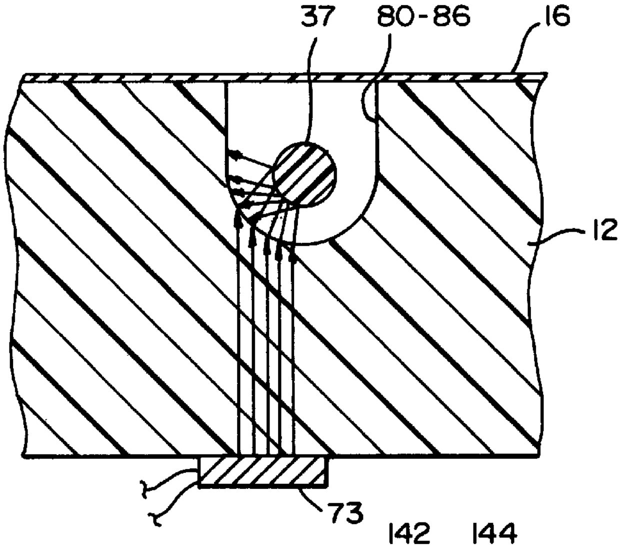
FIG. 22
FIG. 24
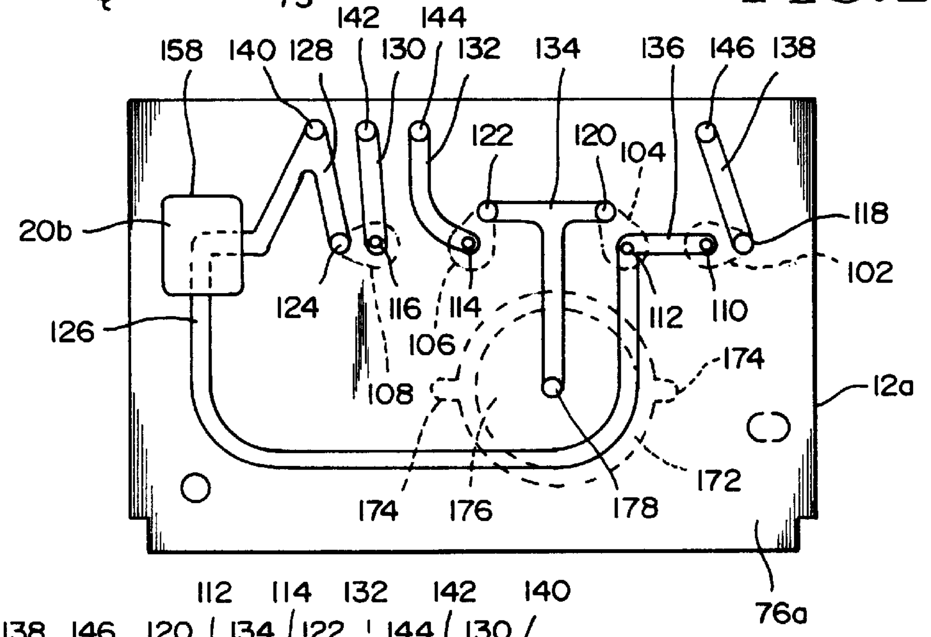
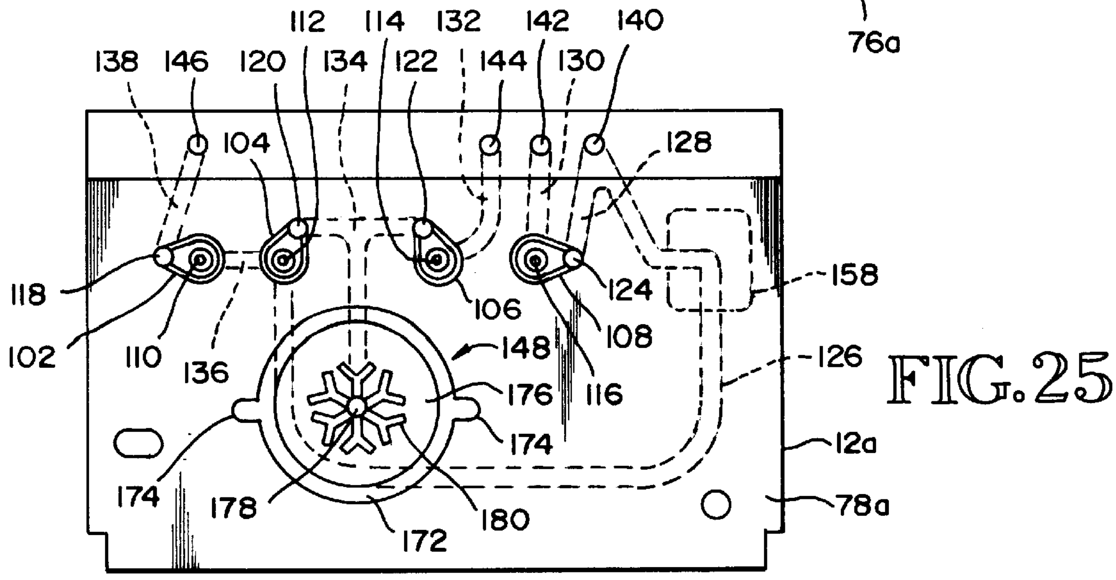
FIG. 25

DISPOSABLE FLUIDIC CIRCUIT CARDS

BACKGROUND OF THE INVENTION

The present invention may relate to devices for sensing the presence, or the amount, of one or more targeted materials in a liquid test sample. The target materials may be inorganic, organic and/or biological in nature. If biological in nature, the target material may, for example, comprise, or be part of, biological fragments, bacteria, viruses and organisms. More particularly, the present invention may relate to such a device comprising a disposable fluidic circuit card. It may further relate to methods for making and using the disposable fluidic circuit card and its various components.

SUMMARY OF THE INVENTION

One aspect of the present invention may be to provide a fluidic circuit card comprising a sensor and all of the fluidic circuit components that may be needed to receive the liquid test sample and deliver the liquid test sample to the sensor. The fluidic circuit card may further comprise fluidic circuit components for disposing of the liquid test sample, and for receiving, delivering, and/or disposing of other fluids used with the fluidic circuit card. Such fluidic circuit components may comprise one or more inlet ports; flow channels; sensor channels or cavities; outlet ports; and/or valves. The term "fluid" as used herein may include both liquids and gases, unless the context should clearly indicate otherwise.

Further aspects of the present invention may be to provide a fluidic circuit card that is suitable for performing immunoassays; and/or to provide immunoassay sensing elements for the fluidic circuit card in any suitable form. Suitable forms for the immunoassay sensing elements may comprise, for example, an optical waveguide around which the liquid test sample may flow; a disc of material through which the liquid test sample may flow; or an area of target material-specific immunoassay chemical material that is bonded to an internal surface of the fluidic circuit card which is exposed to the liquid test sample.

One aspect of the present invention may be to provide a fluidic circuit card that may be used to perform the desired test on more than one liquid test sample (i.e., the card may be used more than once). A further aspect of the present invention may be to provide a fluidic circuit card that may be renewed, such as by replacing or regenerating its sensing element when its sensing element has been used up, or depleted.

Another aspect of the present invention may be to provide an unusually compact fluidic circuit card. This may be done by locating the card's sensor inside the card; by locating the various fluidic circuit components on both the front and back surfaces of the card; and by providing bores extending between the card's front and back surfaces for furnishing fluid communication between the various fluidic circuit components located on its front and back surfaces.

A further aspect of the present invention may be to provide a fluidic circuit card that is so inexpensive to manufacture that it may be considered to be disposable. This may be done by structuring the card's main body, and its various fluidic circuit components, in such a way that the main body, and its various fluidic circuit components, may be integrally molded in one piece by injection molding the main body from plastic, regardless of how many fluidic circuit components the main body may have.

An additional aspect of the present invention may be that the valves on the fluidic circuit card may be selected to occupy only those functional positions that may be exposed to debris-laden sample fluids. Hence, fouling may be cured by simply discarding the entire fluidic circuit card with little economic impact, since the card is designed to be so low in cost that it may be considered to be a disposable item.

The fluidic circuit card may also be inexpensive to manufacture because its cover for its channels, its valve membrane strip for its valves, and its needle septum strip for its fluidic card ports, may all comprise thin strips of inexpensive sheet material (such as rubber or plastic), which may quickly, easily and inexpensively be adhesively mounted to the fluidic circuit card's front and back surfaces. In addition, the valve membrane strip may be made from a heat-shrink plastic, so that the valve membranes may be quickly, easily and inexpensively drawn taut and wrinkle-free to the desired degree by simply briefly heating the valve membranes after the valve membrane strip has been secured to the fluidic circuit card's main body.

A further aspect of the present invention may be to provide methods for increasing the strength of the adhesive bonds that may be formed between a heat-shrink plastic and a layer of adhesive. Such adhesive bonds may be increased in strength by intentionally damaging the surface of the heat-shrink plastic, such as by the use of a corona discharge or an ionized plasma discharge.

Another aspect of the present invention may be to prevent cross-contamination between the various different liquids that may be used in the fluidic circuit card. This may be accomplished in a variety of ways. First, the card may permit a separating gas bubble to be introduced between the different, successive liquids. Second, tight bends in the card's fluid channels, which may tend to trap liquids, may be avoided by the use of bends having a relatively large radius. Third, the valve cavities may have chamfers to permit the valve membranes to smoothly seat against the bottoms and sides of the cavities when the valve is closed, thereby avoiding spaces between the valve membranes and the bottoms and sides of the cavities which might otherwise tend to trap fluids when the valves are closed.

A further aspect of the present invention may be to provide a fluidic circuit card in which fluid flow in at least some of its fluidic circuit components is bi-directional. Such bi-directional fluid flow may permit the recovery of valuable fluids, and/or may aid in the emptying or cleaning of the card's various fluidic circuit components.

Other aspects of the present invention may be to provide a fluidic circuit card that comprises mass transfer enhancement means for increasing the rate at which the target material in a liquid test sample may reach the surface of the card's sensing element. Such mass transfer enhancement means may take many forms, such as: (a) providing a narrow flow channel for the liquid test sample; (b) alternating the direction of flow of the liquid test sample with respect to the sensing element; (c) providing a sensing element and a sensor channel comprising turbulence producing, non-corresponding cross-sectional shapes; (d) providing a sensor channel comprising turbulence producing, diverging and/or converging nozzle shapes; (e) providing a sensor channel whose path with respect to the sensing element produces a cross-flow component of the liquid test sample with respect to the sensing element; (f) providing a sensor channel having a deformable wall that moves with respect to the sensing element, to produce a cross-flow component of the liquid test sample with respect to the sensing element; (g) providing a means for inducing the sensing element to resonate or vibrate within the sensor channel, to produce a cross-flow component of the liquid test sample with respect to the sensing element; and (h) providing asymmetric pressure fields in the sensor channel, to produce a cross-flow component of the liquid test sample with respect to the sensing element.

A further aspect of the present invention may be to provide means for detecting the presence of liquids and/or bubbles within the main body's fluid channels, such as by the use of at least one light source/photodetector pair that may be operated in a reflective and/or a transmissive mode.

Another aspect of the present invention may be to provide the main body with at least one window that may be used to encode information about the fluidic circuit card; wherein the window may be read by the use of at least one light source/photodetector pair that may be operated in a reflective and/or a transmissive mode.

It should be understood that the foregoing summary of the present invention does not set forth all of its features, advantages, characteristics, structures, methods and/or processes; since these and further features, advantages, characteristics, structures, methods and/or processes of the present invention will be directly or inherently disclosed to those skilled in the art to which it pertains by all of the disclosures herein.

BRIEF DESCRIPTION OF THE FIGURES

FIG. 2 is an enlarged, perspective view, partially broken away, of the sensor socket portion of the fluidic circuit card of FIG. 1;

FIG. 3 is an enlarged perspective view, partially broken away, of a sensor 14 of FIG. 1;

FIG. 4 is an enlarged end elevational view of the assembled fluidic circuit card, taken from the right hand side of FIG. 1;

FIG. 5 is an enlarged end elevational view of the assembled fluidic circuit card, taken from the left hand side of FIG. 1;

FIG. 6 is an enlarged side elevational view of the assembled fluidic circuit card of FIG. 1;

FIG. 7 is an enlarged front elevational view of the assembled fluidic circuit card of FIG. 1, with its cover 16 and reflective strip 18 removed, for clarity;

FIG. 8 is an enlarged back elevational view of the assembled fluidic circuit card of FIG. 1, with its needle septum strip 20, adhesive strip 22 and valve membrane strip 24 removed, for clarity;

FIG. 9 is an enlarged cross-sectional view, partially broken away, taken along line 9—9 of FIG. 7;

FIG. 10 is an enlarged cross-sectional view, partially broken away, taken along line 10—10 of FIG. 8, showing the valve 46 in an open condition;

FIG. 10A is an enlarged cross-sectional view, partially broken away, taken along line 10—10 of FIG. 8, showing the valve 46 in a closed condition;

FIG. 11 is an enlarged front elevational view, partially broken away, of a first embodiment of a mass transfer enhancement means that may be used with the fluidic circuit card of FIG. 1;

FIG. 12 is a cross-sectional view, partially broken away, taken along line 12—12 of FIG. 11;

FIG. 13 is a cross-sectional view, partially broken away, of a second embodiment of a mass transfer enhancement means that may be used with the fluidic circuit card of FIG. 1;

FIG. 14 is an enlarged front elevational view, partially broken away, of a third embodiment of a mass transfer enhancement means that may be used with the fluidic circuit card of FIG. 1;

FIG. 15 is a cross-sectional view, partially broken away, taken along line 15—15 of FIG. 14;

FIG. 16 is an enlarged front elevational view, partially broken away, of a fourth embodiment of a mass transfer enhancement means that may be used with the fluidic circuit card of FIG. 1;

FIG. 17 is a cross-sectional view, partially broken away, taken along line 17—17 of FIG. 16;

FIG. 18 is an enlarged front elevational view, partially broken away, of a fifth embodiment of a mass transfer enhancement means that may be used with the fluidic circuit card of FIG. 1;

FIG. 19 is a cross-sectional view, partially broken away, taken along line 19—19 of FIG. 18;

FIG. 20 is an enlarged front elevational view, partially broken away, of a sixth embodiment of a mass transfer enhancement means that may be used with the fluidic circuit card of FIG. 1;

FIG. 21 is an enlarged cross-sectional view, partially broken away, taken along line 21—21 of FIG. 20;

FIG. 22 is a cross-sectional view, partially broken away, of a seventh embodiment of a mass transfer enhancement means that may be used with the fluidic circuit card of FIG. 1;

FIG. 24 is an enlarged front elevational view of the main body 12*a* of the fluidic circuit card of FIG. 23;

FIG. 25 is a back elevational view of the main body 12*a* of the fluidic circuit card of FIG. 23;

DESCRIPTION OF THE PREFERRED EMBODIMENTS

THE FLUIDIC CIRCUIT CARD 10 (FIGS. 1–10)

Figure 1:
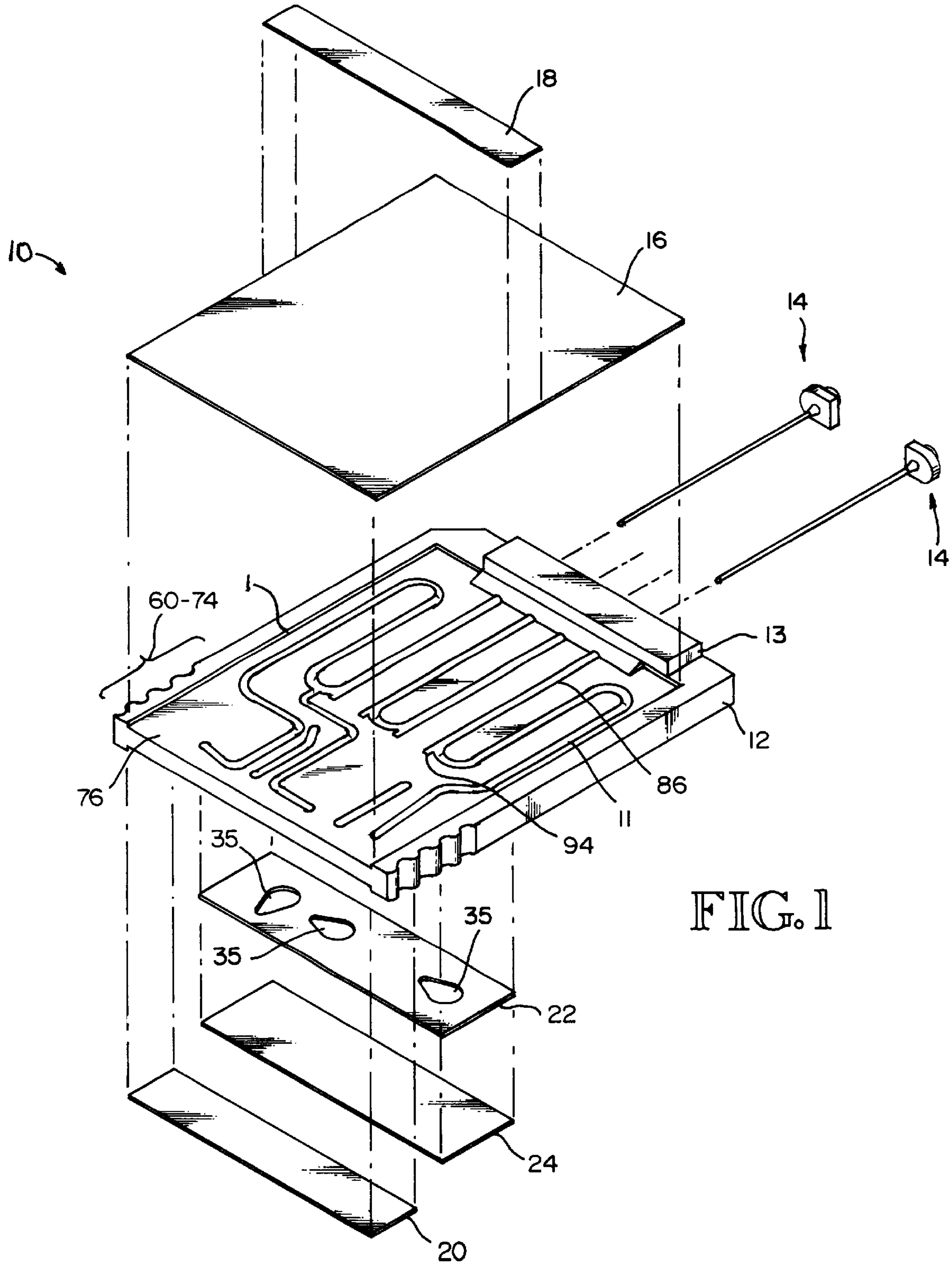
FIG. 1 is an exploded front perspective view of a first embodiment 10 of a disposable fluidic circuit card of the present invention.

Referring now to FIGS. 1–10, which are drawn to scale, they illustrate a first embodiment 10 of the fluidic circuit card of the present invention that may comprise a main body 12; four sensors 14; a cover 16; a reflective strip 18; a needle septum strip 20; an adhesive strip 22; and a valve membrane strip 24. For clarity, in FIG. 1 only two sensors 14 are illustrated; and only one sensor 12 channel 86 and one end recess 94 have been labeled with reference numerals.

The term "fluid" as used herein regarding the fluidic circuit card 10 is defined to encompass both liquids and gases, unless the context should clearly indicate otherwise.

All of the components of the fluidic circuit card 10 may be made from materials that are selected to be compatible with the various fluids with which any particular fluidic circuit card 10 may be intended to be used.

THE MAIN BODY 12:

By way of example, the main body 12 may comprise eight fluidic card ports 26, 28, 30, 32, 34, 36, 38 and 40, each extending between the main body 12's front and back surfaces 76, 78; as best seen in FIG. 5.

As best seen in FIGS. 7 and 8, the main body 12 may also comprise three valves 42, 44 and 46, each of which may be located in its back surface 78. The valves 42–46 may comprise respective inlet and outlet ports 48 and 50, 52 and 54, and 56 and 58; and each of the ports 48–58 may extend between the main body 12's front and back surfaces 76, 78. Also located on the main body 12's back surface 78 may be six windows 33.

As best seen in FIG. 7, the main body 12 may further comprise the following components, each of which may be located in its front surface 76: (a) eight channels 60, 62, 64, 66, 68, 70, 72 and 74; (b) four sensor housing means in the form of four sensor channels 80, 82, 84 and 86, and their respective four end recesses 88, 90, 92 and 94; (c) first and second input channels 1 and 3; (d) three end channels 5, 7 and 9; and (e) an output channel 11.

The channels 60–74 may provide fluid communication between their respective fluidic card ports 26–40 and valve ports 48–58, in the manner illustrated.

The first input channel 1 may provide fluid communication between the sensor channel 80 and the channel 66; while the second input channel 3 may provide fluid communication between the input channel 1 and the channel 70.

The end channel 5 may provide fluid communication between the sensor channels 80 and 82; the end channel 7 may provide fluid communication between the sensor channels 82 and 84; and the end channel 9 may provide fluid communication between the sensor channels 84 and 86.

The output channel 11 may provide fluid communication between sensor channel 86 and the channel 74.

As best seen in FIGS. 2, 4, 7 and 8, the main body 12 may further comprise two sensor sockets 96, 98, each of which may be located in an enlarged end portion 13 of the main body 12.

In the following discussion regarding the valve 46, it will be understood that the same comments may apply to the valves 42 and 44, since the valves 42–46 may all be identical. Referring now to FIGS. 7, 8, 10 and 10A, the valve 46 may comprise an inlet port 56, an outlet port 58, a valve body 2 and a valve membrane 29. The valve body 2 may comprise a raised valve seat 15; a valve seat top 17; a valve seat chamfer 19; a valve cavity 21; a valve cavity periphery 23; a flat valve cavity floor 25; and a valve cavity chamfer 27. A valve gap 31 may be defined between the valve seat top 17 and the valve membrane 29.

Although the valve cavity 21 (see FIG. 10) is illustrated in FIGS. 7 and 8 as having a teardrop shape, it may have any other suitable shape, such as round, or oval, for example.

In order to close the valve 46, the valve membrane 29 may be urged against the valve seat top 17, to stop fluid flow through its inlet port 56. The valve membrane may be urged against the valve seat top 17 by any suitable externally applied closure force. Such a closure force may be applied in any suitable way such as, for example, mechanically, electrically, magnetically, pneumatically, or hydraulically.

If the valve membrane 29 is selected to be made from a resilient or elastic material, the valve 46 may be normally open, and may automatically return to its normally open condition when the externally applied closure force is removed from the valve membrane 29.

The height of the valve seat 15 may be selected so that the valve seat top 17 is below, co-planar with, or above the main body 12's back surface 78, depending on such factors as the size of the desired valve gap 31 and the thickness of the adhesive strip 22.

The valve seat top 17 is illustrated as being convex, for a better seal with the valve membrane 29 when the valve 46 is closed. The amount of curvature of the convex valve seat top 17 may be selected to enable all, or at least most, of the valve seat top 17 to be in contact with the valve membrane 29 when the valve 46 is closed. Alternatively, the valve seat top 17 and the valve seat chamfer 19 may not be separate elements; but may, instead, merge smoothly into each other. As a further alternative, the valve seat top 17 may be flat, or even concave.

As an additional alternative, the raised valve seat 15 and the valve seat chamfer 19 may be eliminated. In such an event, the valve cavity floor 25, or the valve cavity chamfer 27, may extend all of the way to the inlet port 56 and serve as a replacement for the valve seat 15 for the valve membrane 29.

One of the features of the fluidic circuit card 10 may be its ability to eliminate, or at least minimize, the amount of liquid that may be trapped in the valve cavity 21 when the valve 46 is closed. This feature may be important since it may eliminate, or at least minimize, the possibility of cross-contamination between the different liquids that may flow successively through the valve during use of the fluidic circuit card 10.

Accordingly, in order to eliminate, or at least minimize, such undesirable trapping of liquids in the valve cavity 21, the valve seat chamfer 19 and/or the valve cavity chamfer 27 may be suitably sized and shaped to enable the valve membrane 29 to press smoothly against one, or both, of the chamfers 19, 27 when the valve 46 is closed. Alternatively, the flat valve cavity floor 25 may be eliminated, and the valve chamfers 19, 27 may be sized and shaped so as to extend towards and smoothly merge with each other, to enable the valve membrane 29 to press smoothly against the merged chamfers 19, 27 when the valve 46 is closed. Either construction may enable the valve membrane 29 to force all, or at least most, of the liquid out of the valve cavity 21 when the valve 46 is closed. In addition, either construction will provide positive support for the valve membrane 29, when the valve membrane is subjected to an externally applied closure force, to thereby help prevent the valve membrane 29 from being ruptured by the externally applied closure force.

However, as an alternative, one or both of the chamfers 19, 27 may be eliminated, in which case the valve cavity floor 25 may make a right angle intersection with the valve seat 15 and the valve periphery 23, respectively. As an additional alternative, the various components of the valve 46 may be sized and shaped such that the valve membrane 29 does not touch all, or part, of the chamfers 19, 27 or the valve cavity floor 25 when the valve 46 is closed.

By way of example, the various components of the valve 46 may have the following dimensions; although all, or some of them, may be larger or smaller. The teardrop shaped valve cavity 21 may have a maximum length of about 0.265 inches; a maximum width of about 0.188 inches; a minimum width of about 0.063 inches; and a maximum depth in the range of about 0.010–0.020 inches, with respect to the main body 12's back surface 78. The valve seat 15 may extend about 0.010–0.020 inches above the valve cavity floor 25, and may be about 0.063 inches in diameter. The valve seat chamfer 19 may have a maximum thickness in the range of about 0.010–0.020 inches, and may extend outwardly from the valve seat 15 about 0.062 inches. The valve cavity chamfer 27 may have a maximum thickness in the range of about 0.010–0.020 inches, and may extend inwardly from the valve cavity periphery 23 about 0.062 inches. The valve inlet port 56 may be about 0.031 inches in diameter; and the valve outlet port 58 may be about 0.062 inches in diameter. A valve 46 having such dimensions may, when open, and when driven with an input pressure of about 1.0 psi, have a maximum liquid flow rate in the range of about 20–40 cc/min (assuming the liquid to have the viscosity of water).

By way of further example, for an externally applied closure force for the membrane 29 in the range of about 0.2–0.5 psi, and for forward fluid pressures at the inlet port 58 of the valve 46 in the range of about 1.0–2.5 psi; the valve seat 15 may have a diameter of about 0.063 inches and an area of about 0.0031 square inches; and the valve cavity 21 may have an area in the range of about 0.028–0.049 square inches.

Such areas for the valve seat 15 and the valve cavity 21 will result in the ratio of the area of the valve seat 15 to the area of the valve cavity 21 being relatively small, i.e., in the range of from about 1:5–1:20. It may be preferred that the valve seat 15 to valve cavity 21 area ratio be relatively small for several reasons.

First, a relatively small valve seat 15 to valve cavity 21 area ratio may aid forward flow of fluids through the valve 46, from its inlet port 56 to its outlet port 58, when the valve 46 is open, by reducing the pressure drop across the valve 46. The pressure drop across the valve 46 may be reduced because the relatively small area ratio means that the valve outlet port 58 can be made comparatively large compared to its inlet port 56, and because it means that an increased flow cross-sectional area within the valve cavity 21 is available.

Second, a relatively small valve seat 15 to valve cavity 21 area ratio may be important in view of the relatively low pressures used in the fluidic circuit card 10 and its valve 46. This is because any air bubbles trapped within the valve cavity 21 tend to move away from the high flow rate area around the relatively small inlet valve seat 15 towards more stagnant areas within the valve cavity 21, thereby minimizing the impact of any trapped bubbles on the pressure drop across the valve 46.

Third, a relatively small valve seat 15 to valve cavity 21 area ratio may aid the valve 46 in resisting leakage of fluids in a forward flow direction when the valve 46 is off and subjected to a forward fluid pressure at its inlet port 56. This may be because a small valve seat 15 to valve cavity 21 area ratio may produce fluidic force multiplication, thereby enabling a small externally applied closure pressure for the membrane 29 (that turns the valve 46 off), to defeat a much larger forward fluid pressure at its inlet port 56.

For example, if the valve seat 15 and the valve cavity 21 areas are similar (so that the valve seat 15 to valve cavity 21 area ratio is approximately 1), then the closed valve 46 may be expected to defeat a forward fluid pressure that is approximately equal to the applied closure pressure. On the other hand, if the valve seat 15 to valve cavity 21 area ratio is 1:10, for example, then the closed valve 46 may be expected to defeat a forward fluid pressure at its inlet port 56 that is about 10 times as large as the closure pressure; a fluidic force multiplication of about 10 times. In actual practice, the fluidic force multiplication actually achieved may be less than the valve seat 15 to valve cavity 21 area ratio, due to such factors as the elasticity of the valve membrane 29 and due to bottoming out of the valve membrane 29 on the valve cavity floor 25.

However, even a 2–3 times fluidic force multiplication may be important since it may allow the fluidic circuit card 10 to use a single, relatively low pressure, fluidic pressure source that both urges fluids to flow through the card 10, and controls the valve 46. Thus, a valve 46 which provides fluidic force multiplication may allow the design of simpler and less costly systems in which the fluidic circuit card 10 may be used. This is because a separate, relatively high pressure, fluidic pressure source to control the valve 46 may not be not needed in addition to the relatively low pressure fluidic pressure source that urges fluids to flow through the card 10.

One of the features of the fluidic circuit card 10 may be its ability to minimize undesirable cross-contamination between liquids, if different liquids flow in succession through any of the channels 60–74, sensor channels 80–86, input channels 1 and 3, end channel 7, and output channel 11. This may be accomplished by providing turns having a relatively large radius of curvature where any of these channels change direction. This is because a turn having a relatively large radius of curvature may not tend to trap liquids, as compared to a sharply angled turn, such as a right angle turn, which may tend to trap liquids.

It has been discovered that the above undesirable trapping of liquids in the turns in the channels 60–74, sensor channels 80–86, input channels 1 and 3, end channel 7, and output channel 11 may be eliminated, or at least minimized, if the turns have a radius of curvature of at least about 3–4 times the radius or half-width of the particular channels 60–74, sensor channels 80–86, input channels 1 and 3, end channel 7, and output channel 11 having the turns.

Another of the features of the fluidic circuit card 10 may be its unusual compactness, which may be provided by the fact it may utilize both the front and back surfaces 76, 78 of its main body 12 as locations for its various fluidic circuit components, with through bores providing fluid communication between the fluidic circuit components on the front and back surfaces 76, 78. For example, the channels 60–74, sensor channels 80–86, end recesses 88–94, input channels 1 and 3, end channel 7, and output channel 11 may be located on the front surface 76; the valves 42–46 may be located on the back surface 78; and fluid communication may be provided therebetween by the inlet and outlet ports 48–58.

As alternatives, some or all of the channels 60–74, sensor channels 80–86, end recesses 88–94, input channels 1 and 3, end channel 7, and output channel 11 that are shown located on the front surface 76 may be located on the back surface 78; and some or all of the valves 42–46 that are shown located on the back surface 78 may be located on the front surface 76. In either event, any needed fluid communication may be provided between the various fluidic circuit components on the front and back surfaces 76, 78 by a suitable number of appropriately located bores extending between the front and back surfaces 76, 78, as needed.

The card 10's unusual compactness may also be due, in part, to the fact that the sensors 14 may be mounted at one end of the card 10 in the sensor sockets 96, 98, with their sensing elements 37 extending inwardly into the card 10's sensing channels 80–86.

The overall length of the card 10, and of its sensor channels 80–86, may be a function of the particular assay or other sensing strategy being utilized by the card 10 to detect the target material. For example, if an optical waveguide evanescent wave assay is being performed to detect the target material, then the sensing elements 37 may be optical waveguides about 1.5 inches long; with their sensor channels 80–86 being slightly longer. Alternatively, the sensing elements 37 may be as short as a few microns in length, such as if a micromachined sensing element 37 is utilized, or if an assay is employed that is based on the use of dot-type assay geometries, such as ELISA (enzyme-linked immunosorbant assay). In such an event, the sensor channels 80–86 would may also be as short as a few microns in length; and the overall length and width of the card 10 may then be dominated by the size of its other elements, such its valves 42–46, channels 60–74, input channels 1 and 3, end channels 5–9, and output channel 11.

It is understood that, depending on the intended use of the fluidic circuit card 10: (a) the main body 12 may have more than one output channel 11; (b) the main body 12 may have fewer or more fluidic card ports 26–40, valves 42–44, channels 60–74, sensor channels 80–86, end recesses 88–94, input channels 1–3, end channels 5–9 and sensor sockets 96, 98; and (c) that any needed fluid communication between all of the foregoing components of the main body 12 may be provided by suitably arranging the foregoing components with respect to each other on the main body 12.

Another of the features of the fluidic circuit card 10 may be that the main body 12, and all of the main body 12's ports 26–40, valves 42–46 (except for the valve membranes 29), channels 60–74, sensor channels 80–86, end recesses 88–94, input channels 1–3, end channels 5–9, and sensor sockets 96, 98 may be intentionally shaped in such a way that the main body 12, and all of its foregoing components, are suitable for being integrally formed in one piece, by being injection molded from plastic.

This feature may be important because it permits the cost of the main body 12 to be minimized, thereby permitting the fluidic circuit card 10 to be so low in cost that it may be a disposable item. Such cost minimization may be achieved in at least two ways. First, the injection molding of a product in one piece from plastic is inherently relatively inexpensive. Second, once the molding dies have been made, the cost to mold the main body 12 is independent of how many of its foregoing components there may be. For example, it would be just as inexpensive to injection mold a main body 12 having eight valves 42–46, as it would be to mold a main body 12 having only three valves 42–46.

However, as an alternative, the main body 12, and one or more of its foregoing components, may be made by any other suitable way besides being injection molded, such as being formed as two or more separate pieces that are then assembled together.

The main body 12 may be molded from any suitable tough, durable plastic, such as polycarbonate, polymethylmethacrylate or polystyrene.

The main body 12 may be molded from a plastic that is clear, or at least translucent, so that liquids and bubbles within the main body 12's channels 1–11, 60–74 and 80–86 may be observed; or may be detected, such as by the use of at least one light source 91 and photodetector 93 pair, as will be described below.

Alternatively, the main body 12 may be molded from a plastic that absorbs strongly at the wavelength of the input light that may be used to interrogate the sensors 14, in order to prevent cross-talk between the adjacent sensors 14. If the plastic does not, itself, absorb strongly at the wavelength of the input light, then it may be dyed with any suitable dye which does. The main body 12 may be made thin enough in the vicinity of the windows 33 and the bubble detectors D1–D3 to permit light from the light sources 91 to reach their respective photodetectors 93, despite the absorbance of the main body 12. Alternatively, the light sources 91 may be selected to emit light at wavelengths that are not strongly absorbed by the main body 12.

By way of example, the main body 12, and its various features, may have the following dimensions; although all, or some of them, may be larger or smaller.

The main body 12 may have an overall length of about 2.7 inches; an overall width of about 2.1 inches; and an overall thickness of about 0.19 inches, except for its enlarged end portion 13 which may have a thickness of about 0.27 inches. The enlarged end portion 13 may have a length of about 0.27 inches, and a width of about 1.4 inches.

The channels 1–11, 60–74, and 80–86, and the sensor channel end recesses 88–94, may each have a generally U-shaped cross-section. The channels 1, 3, 7, 11, 60–74, and 80–86 may each have a width of about 0.070 inches, a maximum depth of about 0.070 inches, and a semicircular bottom. The sensor channel end recesses 88–94 may each have a width of about 0.038 inches, a maximum depth of about 0.049 inches, and a semicircular bottom. The end channels 5 and 9 may each have a width of about 0.070 inches, a maximum depth of about 0.050 inches, and a semicircular bottom. The fluidic card ports 26–40 may each have a diameter of about 0.063 inches.

Alternatively, one or more of the channels 1–11, 60–74 and 80–86 may have any other suitable cross-sectional configuration which would enable them to be injection molded as an integral part of the main body 12, such as a V-shape or a C-shape, for example.

Each sensor socket 96, 98 may be about 0.2 inches high, may have a maximum width of about 0.45 inches, and may be about 0.15 inches deep. There may be fewer, or more, sensor sockets 96, 98, depending on how many sensors 14 the card 10 may comprise. The sensor sockets 96, 98 may also vary in shape and size, depending on the shape and size of the particular sensors 14 with which they may be adapted to be used.

Although six windows 33 are illustrated, there may be fewer, or more windows 33; and although the windows 33 are illustrated as being small rectangles, they may have any other suitable size and shape. By way of example, each window 33 may be about 0.12 inches long and about 0.16 inches wide. Each window 33 may be recessed into the main body 12's back surface by about 0.04 inches, to help prevent damage to the windows 33, which might otherwise cause them to be misread.

Alternatively, the windows may not be recessed into the main body 12's back surface 78; but may be simple outlines on the back surface 78, or may extend above the back surface 78.

Figure 7A:
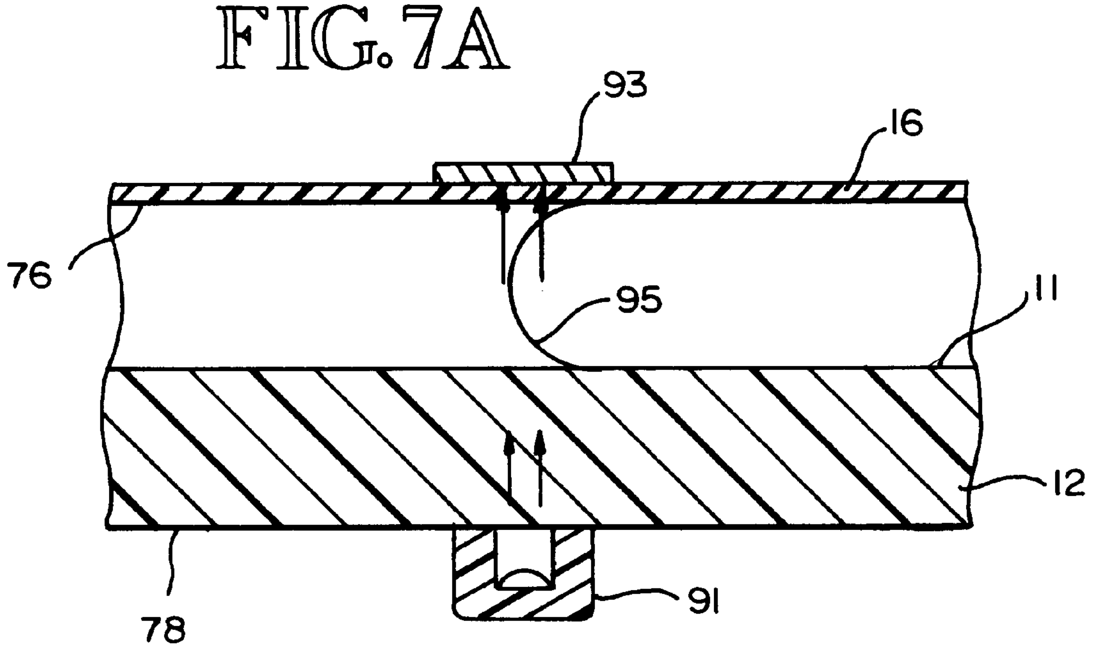
FIGS. 7A and 7B are enlarged cross-sectional views, partially broken away, illustrating a transmissive and a reflective light source/photodetector detection apparatus, respectively, that may be used with the fluidic circuit card 10 of FIG. 1 and with the fluidic circuit card 100 of FIG. 23.
Figure 7B:
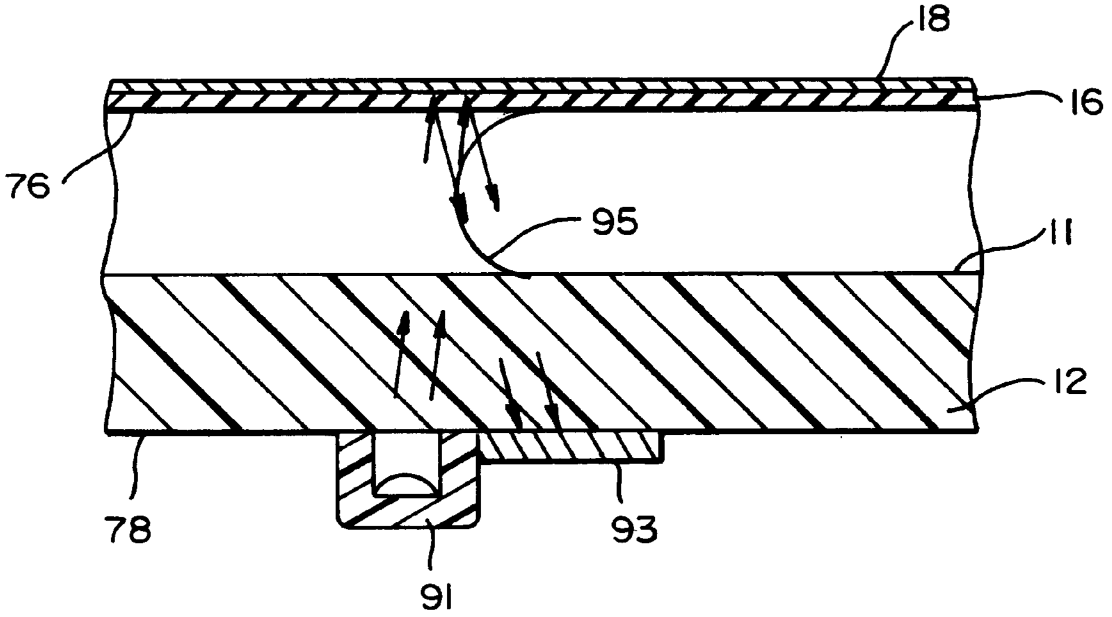

THE LIGHT SOURCE 91 AND PHOTODETECTOR 93 PAIR(S):

Referring now to FIGS. 7A and 7B, they illustrate, respectively, a transmissive system and a reflective system for the detection of fluids and bubbles within any of the main body 12's channels 1–11, 60–74 and 80–86, such as within its channel 11, for example.

In the transmissive system of FIG. 7A, a light source 91 and photodetector 93 may be located on opposite surfaces 76, 78 of the main body 12. The photodetector 93 may detect changes in the light it receives from the light source 91, such as those changes caused by the edge 95 of a bubble; or those caused by light refraction or absorption by a fluid within the channel 11.

In the reflective system of FIG. 7B, the light source 91 and photodetector 93 may be located on the same surface 76 or 78 of the main body 12. A reflective strip 18 may be secured in any suitable way, as with an adhesive, to the opposite surface 76 or 78 of the main body 12. For example, if the light source 91 and the photodetector 93 were located on the back surface 78, then the reflective strip 18 may be secured to the cover 16 on the front surface 76. The reflective strip 18 may be made from any suitable reflective plastic or metallic material, such as Laser Colorstick, metallic silver, manufactured by Paperdirect, Inc. located in Secaucus, N.J. The reflective strip 18 may be about 1.9 inches long, about 2.7 inches wide, and about 0.005 inches thick.

In the reflective system of FIG. 7B, the photodetector 93 may detect changes in the light it receives from the light source 91 that has been reflected by the reflective strip 18, such as those changes caused by the edge 95 of a bubble; or those caused by light refraction or absorption by a fluid within the channel 11.

Alternatively, in a reflective system the reflective strip 18 may be eliminated if the photodetector 93 is to detect changes in the light from the light source 91 that it receives that has been reflected directly from the fluids or bubbles within the main body 12; such as the light that has been reflected from the edge 95 of a bubble within the channel 11, for example. In general, more light may be reflected by a fluid within the channel 11 which is a gas, than is reflected by a fluid which is a liquid.

Any particular light source 91 and photodetector 93 pair, whether transmissive or reflective, may be located adjacent the particular channel 1–11, 60–74 and 80–86 it is to monitor. One, more than one, or all of the channels 1–11, 60–74 and 80–86 may be monitored, as desired; and any particular channel 1–11, 60–74 and 80–86 may be monitored at any desired position along its length where the light would not be obstructed by some other part or feature of the fluidic circuit card 10.

By way of example, if there were three light source 91 and photodetector 93 pairs D1, D2 and D3, they may be located as seen in FIG. 7, i.e.: (a) the pair D1 may be located adjacent to a first end of the channel 11, near the valve 42, to monitor the passage of gases, liquid test samples, liquid buffers, and waste gases and liquids through the first end the channel 11; (b) the pair D2 may be located adjacent to a second end of the channel 11, to monitor the passage of gases and liquid reagents through the second end of the channel 11; and (c) the pair D3 may be located adjacent to the channel 1, near the sensor channel 80, to monitor the passage through the channel 1 of gases, liquid buffers, and waste gases and liquids.

Turning now to the six windows 33 on the main body's back surface 78 (see FIG. 8), they may be used in conjunction with at least one light source 91 and detector 93 pair as part of a data encoding system for the fluidic circuit card 10 (see FIGS. 10 and 10A). By way of example, a particular fluidic circuit card 10 may be data encoded by selectively whitening or blackening one or more of the windows 33, as with ink, or paint. Alternatively, one or more of the windows 33 may be left clear. Such data encoding may be used, for example, where the fluidic circuit card 10 is to be employed with an automated assay system; and may provide any desired information to the automated assay system, such as what particular assay protocols to use with that particular fluidic circuit card 10.

Any suitable whitening material for the windows 33 may be used, such as a white paint that is solvent-compatible with the main body 10; or Liquid Paper, which is manufactured by the Gillette Company of Boston, Mass. Any suitable blackening material for the windows 33 may be used, such as a black paint that is solvent-compatible with the main body 10; or a pencil with a high proportion of charcoal or carbon, such as a type 1B.

In order to read the data encoded on the fluidic circuit card 10, the automated assay system with which it may be used may be provided with a light source 91 and photodetector 93 pair for one, or more, of the windows 33. Such a light source 91 and photodetector 93 pair may be used either in a transmissive system or in a reflective system.

In a transmissive system like that of FIG. 7A, the portion of the main body 10 that is located between the light source 91 and the photodetector 93 may be made from a material that is transparent, or at least translucent, so that light from the light source 91 may pass through the main body 10. This will enable the photodetector 93 to detect the presence of light from the light source 91 that passes through the main body 10 and a clear window 33, or to detect the absence of light that is blocked by a whitened or blackened window 33.

In a reflective system, the light source 91, the window 33 and the photodetector 93 may be arranged so as to enable the photodetector 93 to detect the presence of light from the light source 91 that is reflected from a whitened window 33, or to detect the absence of reflected light from a clear or blackened window 33. In such a reflective system the light source/photodetector pair 91, 93 may be located either on the same side of the main body 12 as the window 33, or on the side of the main body 12 that is opposite from the window 33.

In the alternative reflective system seen in FIG. 7B, a reflector 18 may be used. This will enable the photodetector 93 to detect light from the light source 91 and the reflector 18 that passes through the main body 10 and a clear window 33, or to detect the absence of light that is blocked by a whitened or blackened window 33.

THE COVER 16:

As best seen in FIG. 1, the cover 16 may be sized to cover the fluidic card ports 26–40, channels 60–74, sensor channels 80–86, end recesses 88–94, input channels 1–3, end channel 7, and output channel 11. Naturally, the cover 16 need not cover those portions of the sensor channels 80–86 that are located within the main body 12's enlarged end portion 13. For a main body 12 having the dimensions set forth above, the cover 16 may be about 1.9 inches wide, and about 2.4 inches long; and may be about 0.005 inches thick.

The cover 16 may be made from any suitable material, such as from a flexible or rigid sheet of polycarbonate plastic, or an adhesive backed tape such as tape #5421 manufactured by the 3M Corporation of St. Paul, Minn. Preferably, the cover 16 may be clear, in order to permit observation, or detection, of the passage of fluids and bubbles through the various fluidic circuit components on the main body 12.

The cover 16 may be secured to the main body 12 in any suitable way, such as by the use of an adhesive, or by any suitable fasteners. A suitable adhesive may be type 9460PC transfer tape, manufactured by the 3M Corporation. Preferably, the cover 16 may be pre-coated with a layer of adhesive, like pre-gummed plastic box tape, and may be die cut to size on release media. Such a cover may then be quickly, easily and inexpensively installed on the main body 12 simply by removing it from the release paper, and then applying it to the main body's front surface 76.

Alternatively, if the layer of adhesive on the cover 16 is not compatible with the fluids to be used in the fluidic circuit card 10, then prior to installing the cover 16, the portions of the cover 16's adhesive that would overlie the fluidic card ports 26–40, channels 60–74, sensor channels 80–86, end recesses 88–94, input channels 1–3, end channel 7, and output channel 11 may be covered with a layer of a suitable protective material, such as a die cut plastic that is compatible with the fluids to be used in the fluidic circuit card 10, leaving the rest of the adhesive layer on the cover 16 exposed.

Alternatively, if the layer of adhesive on the cover 16 is not compatible with the fluids to be used in the fluidic circuit card 10, the layer of adhesive may be applied to the main body 12's front surface 76 as a layer that may be die cut to the same size as the cover 16, but which is applied to the main body 12 separately from the cover 16. Such an adhesive layer may be provided on a release media, and may have been die cut in such as way so as to cut out those of its portions that would correspond to the fluidic card ports 26–40, channels 60–74, sensor channels 80–86, end recesses 88–94, input channels 1–3, end channel 7, and output channel 11. After such a layer of adhesive has been applied to the main body 12's front surface 76, the cover 16 may then be applied to it.

Alternatively, the layer of adhesive for the cover 16 may be screen printed onto either the main body 12 or the cover 16 prior to applying the cover 16 to the main body 12. If the layer of adhesive is screen printed onto the main body 12, care may be taken to prevent the entry of the adhesive into the card ports 26–40, channels 60–74, sensor channels 80–86, end recesses 88–94, input channels 1–3, end channel 7, and output channel 11. Any suitable screen-printable adhesive may be used, such as type P-92 ultraviolet-curing adhesive manufactured by Summers Optical of Fort Washington, Pa.

THE NEEDLE SEPTUM STRIP 20:

Referring again to FIG. 1, the needle septum strip 20 may be secured to the main body 12 over its fluidic card ports 26–40 in any suitable way, such as by the use of a pre-applied adhesive such as type CHR 300 silicone with PSA backing, manufactured by the Furon Company, located in New Haven, Conn.

Alternatively, if the layer of adhesive on the needle septum strip 20 is not compatible with the fluids to be used in the fluidic circuit card 10, then prior to installing the needle septum strip 20, the portions of the needle septum strip 20's adhesive that would overlie the fluidic card ports 26–40 may be covered with a layer of a suitable protective material, such as a die cut plastic that is compatible with the fluids to be used in the fluidic circuit card 10, leaving the rest of the adhesive layer on the needle septum strip 20 exposed.

Alternatively, if the layer of adhesive on the needle septum strip 20 is not compatible with the fluids to be used in the fluidic circuit card 10, the layer of adhesive may be applied to the main body 12's back surface 78 as a layer that is the same size as the needle septum strip 20, but which is applied to the main body 12 separately from the needle septum strip 20. Such an adhesive layer may be provided on a release media, may have been die cut to size, and may have been further die cut in such as way as to cut out those of its portions that would correspond to the fluidic card ports 26–40. After such a layer of adhesive has been applied to the main body 12's back surface 78, the needle septum strip 20 may then be applied to it.

Alternatively, the layer of adhesive for the needle septum strip 20 may be screen printed onto either the main body 12 or the needle septum strip 20 prior to applying the needle septum strip 20 to the main body 12.

The purpose of the needle septum strip 20 may be to provide a sealing contact with needles, or other probes, that may be inserted through the needle septum strip 20 in order to insert fluids into the fluidic card ports 26–40, and to remove fluids from the fluidic card ports 26–40.

By way of example, the needle septum strip 20 may be about 1.9 inches long, about 0.30 inches wide, and about 0.031 inches thick. The needle septum strip 20 may be made from any suitable sealing material, such as natural rubber or silicone rubber.

Alternatively, the needle septum strip 20 may be eliminated, such as if the external equipment with which the fluidic circuit card 10 was to be used was provided with suitable means for sealing the fluidic card ports 26–40 during use of the fluidic circuit card 10, such as O-seals or a flat gasket.

THE ADHESIVE STRIP 22 AND THE VALVE MEMBRANE STRIP 24:

Referring again to FIG. 1, the valve membrane strip 24 may be secured to the main body 12's back surface 78 in any suitable way, such as by the use of an adhesive strip 22 having valve holes 35 cut into it.

To install the valve membrane strip 24, the adhesive strip 22 may first be applied to the main body 12 with its valve holes 35 in registration with the valve cavities 21 of the valves 42–46. Then the valve membrane strip 24 may be stuck to the top surface of the adhesive strip 22. The height of the valve gap 31 (see FIG. 10), may be selected by suitably varying such factors as: (a) the thickness of the adhesive strip 22, and/or (b) the distance, if any, that the valve seat top 17 may lie above, or below, the main body 12's back surface 78.

Alternatively, the adhesive strip 22 may be eliminated, and the valve membrane strip 24, except for those portions that may serve as the valve membranes 29, may be coated with adhesive material in any suitable way, such as by printing the adhesive material on the valve membrane strip 24, or by spraying the adhesive on the valve membrane strip 24 through a stencil.

Alternatively, the adhesive strip 22 (or an adhesive coating on the valve membrane strip 24) may be eliminated, and the valve membrane strip 24 may be secured to the main body 12 by the use of an overlying securing member having valve holes 35 cut into it; with the valve membrane strip 24 being tightly sandwiched between such a securing member and the main body 12.

By way of example, the valve membrane strip 24 and the adhesive strip 22 may each be about 0.6 inches long and about 1.9 inches wide. The adhesive strip 22 may be in the range of about 0.002–0.005 inches thick, and may be made from type 9460PC transfer tape, manufactured by the 3M Corporation. Preferably, both the valve membrane strip 24 and the adhesive strip 22 may be die cut and mounted on release media, for easier installation on the main body 12.

It has been discovered that the valve membrane strip 24 may be made from conventional plastic shrink film (in an unshrunk condition), such as polyolefin shrink film or type LD-935 film, manufactured by W.R. Grace & Co., located in Duncan, S.C. The polyolefin shrink film may have a thickness of in the range of about 0.00030–0.0010 inches. As is known, such shrink films shrink when heated to a predetermined temperature, such as about 250° F.–350° F. Alternatively, a non-polyolefin shrink film may be used, such as the PVDF films used for the home storage of foodstuffs.

After the unshrunk valve membrane strip 24 has been secured to the main body 12, the main body 12 and its valve membrane strip 24 may then be briefly heated, as with a hot air stream, or in an oven. The temperature and duration of the heating process may be selected to be just sufficient to shrink the valve membranes 29 to the point that they are drawn taut enough so that all significant wrinkles may have been eliminated from the valve membranes 29. A significant wrinkle may be a wrinkle that is sufficient to prevent a sealing contact between the valve membrane 29 and the valve seat top 17 when the valve 42–46 is closed. By way of example, heating the main body 12 and its valve membrane strip 24 in an oven heated to about 120° C. (248° F.) for about 30 seconds may be sufficient to eliminate all significant wrinkles from the valve membranes 29.

The tautness in the valve membranes 29 that results from the heat shrinking process may also have the desirable effects of: (a) automatically keeping the valves 42–46 in an open position when no externally applied closure force is being applied to their valve membranes 29, and (b) of automatically returning the valves 42–46 to an open position upon the removal of any externally applied closure force that had previously urged the valve membranes 29 against their respective valve seat tops 17.

It has also been discovered that the heating process does not harm the adhesion between the main body 12, the adhesive strip 22, and the valve membrane strip 24; and does not cause significant wrinkles to form in the portions of the valve membrane strip 24 that are secured to the main body 12. This is apparently because the heating process does not cause the secured portions of the valve membrane strip 24 to shrink a significant amount.

This may be due to the fact that since the valve membranes 29 are not in contact with the main body 12, they may be heated to the desired temperature in a very short period of time since they weigh virtually nothing, and thus may have a thermal inertia that is essentially zero. However, the rest of the valve membrane strip 24, which is firmly secured to the main body 12, may have a very high thermal inertia since the main body 12 may act as a heat sink for it. As a result, it has been discovered that a heating process that is sufficient to cause the valve membranes 29 to shrink to the desired degree of tautness, is not sufficient to cause the portions of the valve membrane strip 24 that are secured to the main body 12 to shrink a significant amount.

It has been further discovered that any wrinkles in the adhered portions of the valve membrane strip 24 that may have been formed when the valve membrane strip 24 was first adhered to the adhesive strip 22 may be automatically rendered harmless, since they may be glued flat by the adhesive strip 22, and thereby not cause any leaks.

One problem with making the valve membrane strip 24 from a polyolefin shrink film is that polyolefin shrink films are known to bond to adhesives with only moderate strength, since all olefin polymers may form rather weak adhesive bonds. This may be due to polyolefins being saturated hydrocarbon polymers which, in their natural state, may have a closed electronic configuration that renders them chemically resistant. Polyethylene may be a typical example of such a polyolefin. The weak adhesive bonds made by polyolefin shrink wrap may result in the undesirable delaminating of the valve membrane strip 24 from the adhesive strip 22, such as when the valve cavities 21 are pressurized with fluids during use of the fluidic circuit card 10.

Two ways of increasing the bonding strength of polymers, and in particular olefin polymers, have been discovered. Both ways involve processing methods that may intentionally damage the surface of the valve membrane strip 24, to make it more reactive, while leaving the underlying substrate of the valve membrane strip 24 unharmed. It is theorized that both of the following processing methods may cause one or more of the following changes to the affected surface of the valve membrane strip 24, thereby increasing the strength of the adhesive bonds which the valve membrane strip 24 may form with the adhesive strip 22: (a) significant bond breakage, (b) the formation of reactive compounds, (c) temporary electrical charging, and (d) piezoelectric poling. Naturally, the processing methods would be used to treat the bonding surface of the valve membrane strip 24 prior to its being secured to the adhesive strip 22.

The first processing method for increasing the adhesive bonding strength of polymers, and in particular olefin polymers, is conventional, and comprises applying in air (or in a mixture of gases containing a suitable amount of oxygen), a high voltage corona discharge to the surface of the valve membrane strip 24. This may be effective because the high voltage corona discharge may produce a high concentration of ozone, which may then, it turn, cause the desired changes to the affected surface of the valve membrane strip 24. By way of example, the corona discharge may have a voltage in the range of about 10,000–50,000 volts; the corona discharge may be applied to the valve membrane strip 24 with a metal bar type electrode; the electrode may be spaced from the valve membrane strip 24 a distance in the range of about 0.010–0.20 inches; and the corona discharge may be applied for a time in the range of about 1–5 minutes. The corona discharge may be applied at atmospheric pressure in air, or in any other mixture of gases containing oxygen in the range of about 5%–100%, by volume.

The second processing method for increasing the adhesive bonding strength of polymers, and in particular olefin polymers, is a discovery, and comprises applying a low pressure ionized plasma discharge to the surface of the valve membrane strip 24. The plasma generating equipment may use conventional radio frequency excitation. The term "low pressure" in this context means that the ionized plasma discharge may take place in a low pressure gas or in a low pressure mixture of gases (which may or may not comprise oxygen). The term "low pressure" in this context means a pressure less than about 10 mmHg.

If the low pressure gas(es) comprise oxygen, then the low pressure ionized plasma discharge may "char" the surface of the valve membrane strip 24, thereby increasing its adhesive bonding strength.

But whether or not the low pressure gas(es) comprise oxygen, each ionized particle generated by the low pressure ionized plasma discharge may have a much greater velocity and energy, as compared to an ionized plasma generated at atmospheric pressure, for example. This is because each ionized particle may acquire more energy from the electric field in the ionized plasma generator before suffering a collision with a neutral gas molecule or the surface of the valve membrane strip 24. Hence, the amount of surface modification of the valve membrane strip 24 (and the corresponding increase in its adhesive bonding strength) that is caused by a low pressure ionized plasma discharge may be considerably greater and more permanent than would be the case if the ionized plasma was generated at atmospheric pressure. This may be because the higher energy ions produced by a low pressure plasma discharge may generate more dangling bonds and penetrate more deeply into the surface of the valve membrane strip 24.

Although it is conventional to use low pressure plasma discharges for such applications as removing photoresist from silicon wafers with minimal physical damage, their use for a non-destructive application, such as promoting the adhesion of the surface of a valve membrane strip 24, is an important discovery.

Similarly, although it is conventional to use plasma discharge hardware for adhesion promotion at atmospheric pressure, where the plasma is produced inside a machine and mixed with air to provide a "cold" plasma at atmospheric pressure; the low pressure ionized plasma discharge of the present invention is an entirely different, important discovery, since it is a "hot" plasma approach that requires putting the valve membrane strip 24 inside the plasma-producing chamber, with no introduction of "cold" gas(es) at atmospheric pressure.

Further, it is also a discovery that the adhesion strength of plastic shrink films can be increased by any method, since plastic shrink films are normally not used in situations where a high degree of adhesion strength is required, as in the valve membrane strip 24.

By way of example, significant adhesion improvements were gained by treating the films forming the valve membrane strip 24 in a Yanaco type LTA-2sN RF (radio frequency) Plasma Asher for a period of 30 seconds at a RF power level of 20 watts and at a pressure of 0.75 microns, using air as the active gas.

Testing of the adhesive bond strength between adhesive strips 22 and valve membrane strips 24 has been done by using adhesive strips 22 made from type 9460PC transfer tape, manufactured by the 3M Corporation. The adhesive strips 22 were used to adhere corona discharge modified, plasma discharge modified, and unmodified polyolefin shrink valve membrane strips 24 to respective glass slides. The glass slides were then placed in a peel test station where increasing loads were applied to the bonds between the adhesive strips 22 and the valve membrane strips 24, until delamination of the valve membrane strips 24 from the glass slides was initiated.

It was found that the adhesive bonding strength of a corona discharge modified or a plasma discharge modified olefin shrink valve membrane 24 was increased by a minimum of from 5 times to 7 times, as compared to the adhesive bonding strength of an unmodified olefin shrink valve membrane 24. However, the actual true upper limit on the increase in the adhesive bonding strength could not be determined by the above test since the bond between the glass slides and the adhesive strips 22 failed before the bond between the adhesive strips 22 and the corona discharge modified or plasma discharge modified valve membrane strips 24 failed.

It is anticipated that corona discharge modification or plasma discharge modification of the surface of non-olefin plastics or polymers, such as PVDF, may also result in an increase in their adhesive bonding strengths.

THE SENSORS 14:

Turning now to FIGS. 1–4 and 6–9, each sensor 14 may comprise a sensing element 37, a mounting collar 39 and a lens 41. The sensing element 37 may comprise any suitable optical waveguide. The sensors 14 may be molded in one piece from any suitable optical plastic, or may be assembled by gluing together the sensing element 37, the mounting collar 39 and/or the lens 41 with any suitable optical adhesive. Although four sensors 14 are illustrated in FIG. 1, there may be fewer, or more sensors 14.

Alternatively, although the sensing element 37 is illustrated as being elongated, it may be as short as a few microns in length, such as if a micromachined sensing element 37 is utilized, or if an assay is employed that is based on the use of dot-type assay geometries, such as ELISA, in which an area of target material-specific immunoassay chemical material is bonded to an internal surface of one or more of the sensor channels 80–86.

As a further alternative, one or more of the sensors 14 may comprise any suitable conventional sensor that is capable of sensing the particular substance or physical parameter of interest regarding the fluid in the sensor channels 80–86.

By way of example, the sensor 14's lens 41 may be spherical, and may have a diameter of about 4.8 mm. However, the lens 41 may have any other suitable shape, and may have a diameter that is larger, or smaller, than the example given.

By way of further example, the optical waveguide sensing element 37 may be cylindrical, may have a diameter of about 0.76 mm, and a length of about 38 mm. However, the optical waveguide sensing element 37 may have a diameter and/or a length that is greater, or smaller, than the example given. In general, at a constant optical input power, the sensitivity of the optical waveguide sensing element 37 may vary as an inverse function of its surface area; i.e., its sensitivity may increase as its surface area decreases, and may decrease as its surface area increases. The surface area of a cylindrical optical waveguide sensing element 37 may be a function of its diameter and length.

By way of example, the sensing element 37 may comprise any conventional tapered or non-tapered optical waveguide in which the sensing element 37 may be affected directly by the substance or the physical parameter being sensed, and/or which may be coated with one or more substances that may be affected by the substance or the physical parameter being sensed.

For the fluidic circuit card 10, input light from an external light source may be focused by the lens 41 into the sensing element 37. The sensing element 37 may then modify the input light as a function of the substance or the physical parameter being sensed regarding the fluid in the sensor channels 80–86, to produce modified output light that is modified as a function of the sensed substance of physical parameter. The modified output light may then leave the sensing element 37 through the lens 41, where it may be received and utilized by any suitable external detection equipment.

There are a multitude of conventional immunoassay detection methods that may be used with the sensing element 37, such as, by way of non-limiting example, displacement immunoassays, sandwich immunoassays and competitive immunoassays.

In a displacement immunoassay detection method the immobilized antibody coating on the outer surface of the sensing element 37 is first tagged with fluorescent antigen. A single incubation step may then be used in which the target antigen in the liquid test sample binds with the antibodies on the outer surface of the sensing element 37, thereby displacing the fluorescently-tagged antigen. The amount of displaced fluorescently-tagged antigen may be a function of the amount of the target antigen in the liquid test sample.

In a sandwich immunoassay detection method, two incubation steps are used. In the first incubation step, the target antigen in the liquid test sample binds with the antibody coating on the outer surface of the sensing element 37, to form bound antibody/target antigen pairs on the outer surface of the sensing element 37. In the second incubation step, a fluorescent dye-tagged antibody binds to the bound antibody/target antigen pairs on the outer surface of the sensing element 37. The amount of bound fluorescently-tagged antibody may be a function of the amount of the target antigen in the liquid test sample.

In a competitive immunoassay detection method, a known amount of dye-tagged antigen is mixed with the liquid test sample containing the target antigen, to form a test mixture. Then, in a single incubation step, the dye-tagged antigen and the target antigen in the test mixture bind with the antibody on the outer surface of the sensing element 37 in respective proportions that are a function of their respective relative concentrations in the test mixture.

By way of further example, if the sensing element 37 is to be used in a displacement immunoassay, such as to detect small molecules such as TNT (trinitrotoluene) or biological molecules such as botulin toxin or Ricin toxin, any suitable antibody of choice may be immobilized on the outer surface of the sensing element 37 in any suitable way, such as by covalent binding techniques.

During preparation of the sensing element 37 for the detection of small molecules (like TNT), the antibody sites on the outer surface of the sensing element 37 may be filled with a fluorescently-tagged variant of the target antigen, such as fluorescently-tagged TNT. During use of such a sensing element 37, the target antigens (or other target material) in the liquid test sample may bind to the antibodies on the outer surface of the sensing element 37. As a result, the output fluorescent light from the sensing element 37 may decrease as a function of the amount of target material in the liquid test sample, thereby giving an indication of the presence, or the amount, of the target material in the liquid test sample.

As an additional example, during preparation of the sensing element 37 for use in a sandwich assay for the detection of both large and small molecules, a recognition antibody may be prepared that is tagged with a fluorophore, while the capture antibody-coated outer surface of the sensing element 37 may be left with all of its antibody sites available for reaction. During the sandwich assay, the sensing element 37 may first be incubated with the sample containing the possible target antigen. The sensing element 37 may then be incubated in a reagent containing the fluorophore-tagged antibody. At this point the fluorophore-tagged antibody attaches to the outer surface of the sensing element 37 at sites that contain antigen that was bound during the sample incubation step. As a result, the fluorescent signal light from the sensing element 37 increases with time as a function of the amount of the target antigen that was bound.

Two sensors 14 may be mounted in each sensor socket 96, 98, as seen in FIG. 4. Their mounting collars 39 may be glued in the sockets 96, 98 with an adhesive to form a leak-proof seal between the mounting collars 39 and the sockets 96, 98. Any suitable adhesive may be used, such as UV adhesive #61, manufactured by Norland Products, Inc., located in New Brunswick, N.J.

Alternatively, the sensors 14 may not be glued in the sockets 96, 98, so that they can be replaced by the user, as needed. In such an event, the enlarged end portion 13 of the main body 12 may be made removable, and a gasket may be located between such a removable end portion 13 and the rest of the main body 12. The gasket may have a hole corresponding to each of the lenses 41 for the sensors 14, and may seat against the outer surface of the mounting collars 39 of the sensors 14. The removable end portion 13 may be secured to the rest of the main body 12 in any suitable way, such as by the use of a pair of screws.

Prior to any particular sensor 14 being mounted in its respective sensor socket 96, 98, the distal end of its sensing element 37 may be dipped in a liquid black material to form a ball of black material on the distal end of its sensing element 37. Then, when the sensor 14 is mounted in its respective sensor socket 96, 98, the black ball of material on the distal end of its sensing element 37 may: (a) help hold the distal end in place in its respective end recess 88–94; (b) help accommodate differential temperature induced expansion between the sensing element 37 and the main body 12; and (c) to act as a light trap for input light reaching the distal end, so that it may not be reflected back towards the sensor's lens 41. Alternatively, prior to mounting the sensor 14 in its respective sensor socket 96, 98, the liquid black material may be placed in the sensing element 37's respective end recess 88–94. Any suitable liquid black material may be used to form a ball of black material on the distal end of the sensing element 37, such as T-1 gloss black super enamel paint, manufactured by the Plasticote Co., Inc. of Medina, Ohio. Any suitable liquid black material may be placed in the sensing element 37's respective end recess 88–94, such as the black paint just described, or a black silicone gel.

As best seen in FIG. 9, the sensing element 37's sensor channel 84 may be sized to closely approach the sensing element 37, in order to increase interaction between the sensing element 37 and the fluid in the sensor channel 84. For example, if the sensing element 37 was an optical waveguide having a diameter of about 600 microns, then the distance between the sensing element 37 and the walls of the sensor channel 84 may preferably be in the range of about 25–100 microns.

Alternatively, the sensor 14 may not include a mounting collar 39 or a lens 41, in which event the sensor 14 may comprise, by way of example, a length of clad optical waveguide having a sensing element 37 comprising a portion of the clad optical waveguide from which the cladding has been stripped. For such a sensor 14, the sensor sockets 96, 98 may comprise simple bores 96, 98 in the end of the main body 12 that are sized to closely receive the clad optical waveguide portion of the sensor, which may be sealed in such bores 96, 98 in any suitable way, such as by the use of an adhesive.

Alternatively, the sensor 14 comprise any conventional optical, electrical, chemical or mechanical sensor; and need not necessarily utilize an optical or electrical waveguide. Naturally, the sensor sockets 96, 98 and the sensor channels 80–86, may have to be modified in order to accommodate the particular sensor 14 with which they were intended to be used.

THE OPERATION OF THE FLUIDIC CIRCUIT CARD 10:

The operation of the fluidic circuit card 10 will now be described. In general, any of the fluidic card ports 26–40 may handle the input and/or output of any desired fluid, and the fluidic card ports 26–40 may be connected with each other by the valves 42–46 in a variety of ways. Accordingly, the following descriptions of the operation of the fluidic circuit card 10 are only a few examples of the many ways in which it might be operated.

As has been previously described, the valves 42–46 may all be normally open, due to the tension in their valve membranes 29; and may be closed by any suitable externally applied closure force applied to their valve membranes 29. Thus, when the following description indicates that any of the valves 42–46 are opened, that may mean either that an already open valve 42–46 is left open, or that a closed valve 42–46 is opened by ceasing to apply the externally applied closure force that acts on its valve membrane 29. Similarly, when the following description indicates that any of the valves 42–46 are closed, that may mean either that an already closed valve 42–46 is left closed, or that an open valve 42–46 is closed by applying a suitable externally applied closure force to its valve membrane 29.

For simplicity of description, sensor channel A may be defined as comprising sensor channel 80, end channel 5, sensor channel 82, end channel 7, sensor channel 84, end channel 9, and sensor channel 86.

As part of the following examples of the operation of the fluidic card 10, it may be assumed (unless the context should clearly indicate otherwise), that the fluidic card port 26 may be a second fluid waste output port; card port 28 may be a liquid buffer input port; card port 30 may be a first gas input/output port; card port 32 may be a liquid test sample input port; card port 34 may be a first liquid reagent input/output port; card port 36 may be a second liquid reagent input/output port; card port 38 may be a first fluid waste output port; and card port 40 may be a second gas input/output port.

Since the fluidic circuit card 10 may be used to test more than one liquid test sample before it is discarded because it is used up or contaminated, operation of the card 10 may start by running any suitable liquid buffer through the input channel 1, sensor channel A (see the above definition), and output channel 11 to clean those channels of residual liquid reagents or liquid test samples that may remain in those channels from the last use of the fluidic circuit card 10. A suitable liquid buffer may be one that is compatible with the antibodies and the liquid test sample, such as a phosphate buffered saline solution.

Such cleaning may be done by first closing valves 42 and 44, to prevent back flow of liquid buffer through those valves; opening valve 46; and injecting a suitable amount of the liquid buffer into the card port 28. The liquid buffer would then flow sequentially through channels 62, 64, 66, 1, sensor channel A (see the above definition), channel 11, valve 46, channel 72 and out the first fluid waste output port 38.

Undesired back flow of the liquid buffer into the port 30; into the channel 3, port 34, channel 70 and port 36; and into the channel 74 and port 40, may be prevented by permanent valves comprising part of the companion instrument with which the fluidic circuit card 10 is intended to interface. The valves 42–46 on the fluidic circuit card 10 may be selected to occupy only those functional positions that may be exposed to debris-laden sample fluids. Hence, fouling may be cured by simply discarding the fluidic circuit card 10 with little economic impact, since the card 10 is designed to be so low in cost that it may be considered to be a disposable item. On the other hand, the valves that comprise part of the companion instrument may see only clean fluids, and hence can be made comparatively inaccessible and may comprise more costly valve structures that are designed for long-term, permanent operation.

The liquid buffer may then be removed from the card 10 by forward flushing it out through the first waste output port 38. This may be done by first closing valves 42 and 44, and opening valve 46. A gas may then be injected into the card 10 through the first gas input/output port 30. The gas may then flow sequentially through channels 64, 66, 1, sensor channel A (see the above definition), channel 11, valve 46, channel 72 and out of the first fluid waste output port 38, until all of the liquid buffer has also been forced out of the first fluid waste output port 38. Undesired back flow of the gas and liquid buffer into the channel 62 and port 28; into the channel 3, port 34, channel 70 and port 36; and into the channel 74 and port 40, may be prevented by permanent valves comprising part of the companion instrument with which the fluidic circuit card 10 is intended to interface.

Alternatively, the liquid buffer may be removed from the card 10 by back flushing it out through the second fluid waste output port 26. This may be done by first closing valves 44 and 46, and opening valve 42. A gas may then be injected into the card 10 through the second gas input/output port 40. The gas may then flow sequentially through channels 74, 11, sensor channel A (see the above definition), channel 1, valve 42, channel 60 and out of the second fluid waste output port 40, until all of the liquid buffer has also been forced out of the second fluid waste output port 40. Undesired back flow of gas and liquid buffer through the channel 3, port 34, channel 70 and port 36; and through the channels 66, 64, port 30, channel 62 and port 28 may be prevented by permanent valves comprising part of the companion instrument with which the fluidic circuit card 10 is intended to interface.

In order to run a liquid test sample through the fluidic circuit card 10, valves 44 and 46 may be opened, and valve 42 may be closed. The liquid test sample may then be injected into the card 10 through the sample input port 32, from which it may then flow sequentially through channel 68, valve 44, channels 66 and 1, sensor channel A (see the above definition), channel 11, valve 46, channel 72 and out the first fluid waste output port 38. Undesired back flow of the liquid test sample through the channel 64, port 30, channel 62 and port 28; through the channel 3, port 34, channel 70 and port 36; and through the channel 74 and port 40 may be prevented by permanent valves comprising part of the companion instrument with which the fluidic circuit card 10 is intended to interface.

The liquid test sample may be run continuously through the fluidic circuit card 10 until the sensing elements 37 have provided the desired information regarding the liquid test sample.

Alternatively, after the sensor channel A (see the above definition) has been filled with the liquid test sample, injection of more liquid test sample into the card 10 may be halted, to allow the liquid test sample to interact with the sensing elements 37 for a time sufficient to enable the sensing elements 37 to provide the desired information regarding the liquid test sample.

Alternatively, it may be advantageous to agitate the liquid test sample back and forth over the sensing elements 37, in order to increase the interaction between the liquid test sample and the sensing elements 37, to thereby increase the sensitivity of the sensing elements 37.

This may be done by first injecting into the sample inlet port 32 a quantity of liquid test sample that would be a little more than sufficient to fill the sensor channel A (see the above definition). This precision injection of the liquid test sample may be accomplished in any suitable way. One suitable way will now be described with reference to FIG. 7, which shows the location of the detectors D1–D3. A long bubble is introduced into the fluidic circuit card 10 by closing the valves 42, 44; opening valve 46; and injecting air into the card port 30 until the leading edge of the long bubble is detected by the detector D3. At that time, the injection of air is stopped; the valve 44 is opened; and the injection of the liquid test sample into the card port 32 is started. The liquid test sample will sever the long bubble at the intersection of channels 64 and 66. Injection of the liquid test sample is continued until the trailing edge of the severed gas bubble (the leading edge of the liquid test sample) is detected by the detector D2, at which time the sensor channel A (see the above definition) has been completely filled.

After the desired amount of liquid test sample has been injected into the card port 32, the valves 42 and 44 may be closed, and the valve 46 may be opened. A gas may be injected into the first gas input port 30 until the trailing edge of the severed gas bubble (the leading edge of the liquid test sample) is detected by the detector D1.

At this point in time, the sensor channel A, a small adjoining portion of the input channel 1, and substantially all of the output channel 11 contain the liquid test sample; and the rest of the input and output channels 1 and 11 contain a gas. The liquid test sample in the card 10 may then be agitated back over the sensing elements 37 in the sensor channels 80–86 in the following manner. To cause at least part of the liquid test sample to move over the sensing elements 37 and back into the input channel 1, the valves 44, 46 are closed and gas may be injected into the second gas input/output port 40 until the leading edge of the newly injected gas bubble (the trailing edge of the liquid test sample) is detected by the detector D2. Gas and any liquid in the channels 1, 60 ahead of the liquid test sample may then exit through the waste output port 26.

It should now be apparent that such alternating movement of the liquid test sample back and forth into the output and input channels 11, 1 will cause the liquid test sample to also move, as was desired, back and forth over the sensing elements 37 in the sensor channels 80–86. Such desired alternating movement of the liquid test sample back and forth over the sensing elements 37 may be repeated as many times as may be needed to complete the desired test or incubation.

After the testing or incubation of the liquid test sample has been completed, a gas may be used to force the liquid test sample out of the card 10, either by forward flushing it out through the first fluid waste output port 38, or by back flushing it out through the second fluid waste port 26, in a manner similar to that described above regarding using a gas for forward flushing and back flushing the liquid buffer out of the card 10.

As was described above, sandwich assays require a second incubation with a reagent containing a fluorophore-tagged antibody. However, by way of example, the use of a first liquid reagent that may be injected into the first liquid reagent input/output port 34 will now be described, it being understood that the use of a second liquid reagent that may be injected into the second liquid reagent input/output port 36 may be similar.

Typically, a fresh buffer may first be used to flush the liquid test sample out of the channel A (see the above definition). A long bubble may then be created, in the manner described above, that extends to the detector D3. The valves 42, 44 may then be closed; the valve 46 may be opened; and the desired amount of the first liquid reagent may be injected into the first liquid reagent input/output port 34. From the port 34, the first liquid reagent may then pass sequentially through channels 3 and 1, and into the sensor channel A (see the above definition). Injection of the first liquid reagent into the port 34 may be stopped when the trailing edge of the air bubble (the leading edge of the first liquid reagent) is detected by the detector D2. Undesired back flow of the first reagent into channels 1, 66, 64, port 30, channel 62, and port 28; and into channel 74 and port 40 may be prevented by permanent valves comprising part of the companion instrument with which the fluidic circuit card 10 is intended to interface.

After the sensing elements 37 have been treated with the desired amount of the first liquid reagent, and/or have been treated for the desired amount of time with the first liquid reagent, a gas may then be used to force the first liquid reagent out of the card 10 if the reagent is inexpensive. This may be done by using a gas to either forward flush the used first liquid reagent out through the first fluid waste output port 38, or to back flush it out through the second fluid waste port 26, in a manner similar to that described above regarding forward flushing and back flushing the liquid buffer out of the card 10.

However, the first liquid reagent may be relatively costly and/or it may be used more than once before its usefulness is depleted. Accordingly, it may be useful, and valuable, to be able to recover the first liquid reagent after it has been use to treat the sensing elements 37.

The first liquid reagent may be recovered by first closing valves 42–46. Then a gas may be injected into the second gas input/output port 40 at a pressure sufficient to force all of the used first liquid reagent out through the first liquid reagent input/output port 34, and into any suitable container used to store the first liquid reagent in the external supply source. Undesired back flow of the used liquid reagent into the channels 1, 66 and 64, port 30, channel 62 and port 28 may be prevented by permanent valves comprising part of the companion instrument with which the fluidic circuit card 10 is intended to interface.

In order to help prevent cross-contamination of the different liquids used in the fluidic circuit card 10, it may be useful to use a bubble to separate the different liquids that may be used in the card 10. For example, let us assume that we start with a new, empty card 10; and that we then want to sequentially inject into the card 10 a liquid test sample and then a first liquid reagent.

First, the sensor channels 80–86 may be filled with the liquid test sample in the manner describe above. After the test has been completed, the valves 42 and 44 may be closed and the valve 46 may be opened. A gas may then be injected into the first gas input/output port 30 until it fills the channels 64 and 66, and until the leading edge of the bubble has passed the intersection of the channel 1 with the liquid reagent input/output channel 3 a short distance, such as until the leading edge of the bubble has reached at least the intersection of the channel 1 with the sensor channel 86.

If the first liquid reagent is then injected into the first liquid reagent input/output port 34, in the manner previously described, it will be appreciated that a separating bubble will be automatically formed between the trailing edge of the liquid test sample and the leading edge of the first liquid reagent as soon as the first liquid reagent starts entering the channel 1. Back flow of the first liquid reagent into the channel 1 towards the valves 42, 46 may be prevented by permanent valves comprising part of the companion instrument with which the fluidic circuit card 10 is intended to interface.

MASS TRANSFER ENHANCEMENT (FIGS. 11–22)

MASS TRANSFER ENHANCEMENT, INTRODUCTION:

A sensor 14's sensing element 37 may detect the target material in a liquid test sample by an interaction between the target material and the sensing element 37 (or a coating on the sensing element 37). For example, as was described above, the sensor 14 may utilize any suitable conventional immunoassay detection method in which a coating of an antibody of choice has been immobilized on the outer surface of the sensing element 37.

In all immunoassays the reaction rates may be dominated by the concentration of the target material in the liquid test sample, and by the rate of diffusion of the target material to the outer surface of the sensing element 37. In many immunoassays the target material and the antibodies are generally very large molecules and diffuse very slowly in water and other liquids. Hence, it may be desirable to have methods by which the rate of reaction may be increased, in order to reduce the overall assay time.

By way of example, let it be assumed that the test sample is a water based solution containing target material that is a typical 40,000 MW (molecular weight) protein having a diffusion coefficient of about $0.8(10^{-6})cm^2/sec$. If such an immunoassay sensing element 37 were simply immersed in a liquid test sample contained in a test tube having a 2 mm internal diameter, with no flow of the test sample over the sensing element 37, it may take as long as about 3–4 hours before the concentration of the target material on the outer surface of the sensing element 37 approached equilibrium.

Such lengthy times for performing immunoassays may be due, in large part, to the fact that the availability of the target material at the surface of the sensing element 37 is limited by diffusion-dominated radial mass transfer in the liquid phase.

Accordingly, it may be desirable for the fluidic circuit card 10 to comprise mass transfer enhancement means for increasing the rate at which the target material may reach the surface of sensing element 37; in order to reduce the time needed for the fluidic circuit card 10 to detect the presence, or to measure the amount, of the target material that is present in the test sample. Although such mass transfer enhancement means may be particularly useful where the target material comprises molecules that are relatively large, i.e., those having at least a 40,000 MW; they may also be useful for target materials having lower molecular weights.

Although mass transfer enhancement is discussed herein primarily with regard to the liquid test sample that may contain the target material, it is understood that mass transfer enhancement may be equally important with respect to any other fluids used in the fluidic circuit card 10, such as reagents and buffers.

It is also to be understand that the sensing element 37 may have any other suitable three-dimensional shape besides cylindrical, such as spiral, flat or ribbon-like, for example. In addition, the sensing element 37 may have any other suitable cross-sectional shape besides circular. For example, the sensing element 37's cross-sectional shape may be any curved figure besides circular, may be any geometric figure with straight sides, and may be any combination of the foregoing shapes.

MASS TRANSFER ENHANCEMENT, BI-DIRECTIONAL FLOW:

It has been discovered that mass transfer enhancement means for increasing the rate at which the target material in a liquid test sample may reach the surface of the sensing element 37 may comprise means for causing the liquid test sample to have an alternating, bi-directional flow, back and forth over the sensing element 37 in the sensor channels 80–86.

Such alternating flow or movement of the liquid test sample over the sensing element 37 in the sensor channels 80–86 was describe in detail above regarding the operation of the fluidic circuit card 10.

MASS TRANSFER ENHANCEMENT, NARROW FLOW CHANNELS (FIGS. 11–12):

Referring now to FIGS. 11–12, a mass transfer enhancement means for increasing the rate at which the target material in a liquid test sample may reach the surface of sensing element 37 may comprise a capillary tube 43 seated, as with a friction fit, in a sensor channel 80–86. As seen in FIG. 11, the capillary tube 43 may be seated in narrowed portion of the sensor channel 80–86. Alternatively, the sensor channel 80–86 need not have a narrowed portion; in which case the outer diameter of the capillary tube may be selected to fit snugly within the non-narrowed sensor channel 80–86.

As seen, by suitably sizing the outer diameter of the sensing element 37 with respect to the inner diameter of the capillary tube 43, a relatively narrow annular flow channel 45 may be defined between the sensing element 37 and the capillary tube 43. During use, the liquid test sample may flow continuously through the flow channel 45.

It has been discovered that the effect of the narrow flow channel 45 may be to greatly minimize the maximum distance the target material in the liquid test sample may have to travel by diffusion before interacting with the sensing element 37; thereby greatly minimizing the amount of time needed before the sensing element 37 is able to detect the presence, or to measure the amount, of the target material that is present in the liquid test sample, as compared to conventional batch protocols.

In addition, it has also been discovered that once the flow channel 45 has been filled with the liquid test sample, the subsequent binding of the target material to the antibodies on the surface of the sensing element 37 (and the resulting output signal from the sensing element 37), may be a linear function of the elapsed time during which the liquid test sample is run through the flow channel 45; at least until a substantial fraction of the active sites on the surface of the sensing element 37 have been used.

It has been further discovered that the slope of this linear, time-dependent function may be directly proportional to the concentration of the target material in the liquid test sample. This is in contrast to conventional batch protocols, where the output signal from the sensing element 37 may be a non-linear parabolic diffusion-shaped curve whose magnitude may be proportional to the concentration of the target material in the liquid test sample. Least squares fitting of a linear output curve from the sensing element 37 may be generally much preferable to the nonlinear least-squares curve fitting needed for conventional batch protocols, since it may be implemented with the use of far less sophisticated (and far less costly) detection instrumentation, and since a statistically significant result may be obtained much sooner.

Figure 28:
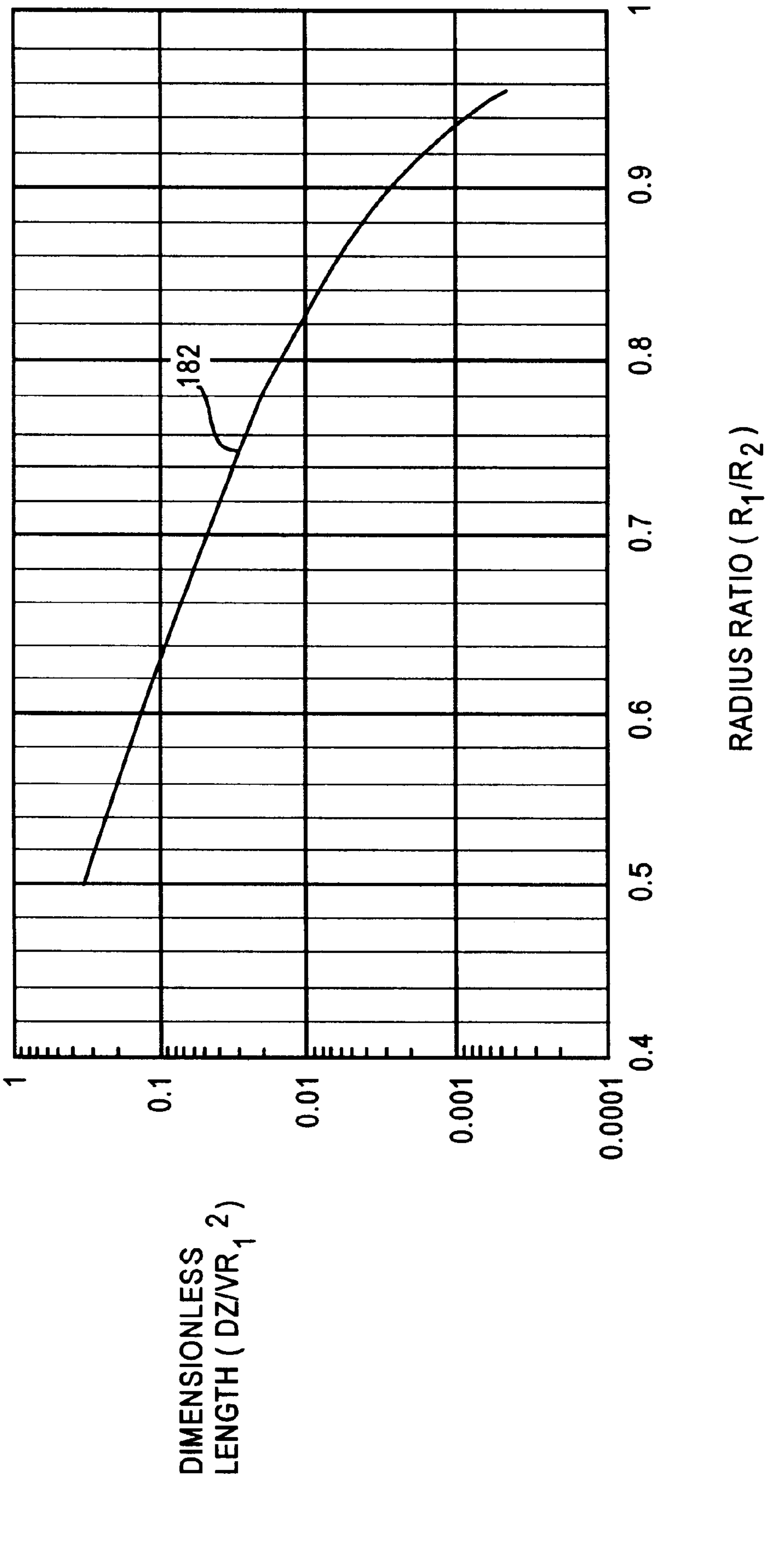
FIG. 28 is a graphical representation regarding the FIGS. 11–12 embodiment of the mass transfer enhancing means.

To find suitable sensing element 37/sensor channel 80–86 designs that have enhanced mass transfer rates, diffusional and convective transport in an annular gap subject to Navier-Stokes laminar coaxial flow may have to be modeled. There is no closed-form solution to this problem, but it may be amenable to modeling by numerical techniques. The graph 182 of FIG. 28 illustrates the relationship between key variables for a tubular-shaped sensing element 37 having a radius of $R_1$ that is located on the axis of a hollow capillary tube 43 having an internal radius of $R_2$. The graph 182 shows the set of conditions that may have to be met in order to remove 50% of the target material (the analyte) from an incoming stream of the liquid test sample. One key parameter is the radius ratio $R_1/R_2$; while the other is a dimensionless length given by:

$$DZ/V(R_1)^2 \quad (1)$$

where D is the diffusion coefficient of the target material in the liquid test sample, Z is the length of the capillary tube 43, and V is the average axial flow velocity in the annular flow channel 45 of the capillary tube 43 during the assay.

By way of example, let it be assumed that $R_1$ and $R_2$ are 300 microns and 350 microns, respectively; that the target material comprises molecules having a 40,000 MW and a D of approximately $0.8(10^{-6})cm^2/sec$; and that 50 $\mu$L of the liquid test sample will flow through the annular flow channel 45 of the capillary tube 43 in a 3 minute period. From FIG. 28, for $R_1/R_2=0.857$ the dimensionless length is approximately 0.0072. Upon substitution of physical values for the variables in the dimensionless length given by Equation 1 above, the physical length Z of the capillary tube 43 is found to be 2.2 cm.

The total flow volume of the liquid test sample in the annular flow channel 45 of this length of capillary tube 43 can be calculated to be about 2.2 $\mu$L. Hence, the volume of the liquid test sample in the annular flow channel 45 will have been replaced 23 times over the 3 minute period, due to the continuous flow of the liquid test sample through the annular flow channel 45 during this period of time. For comparison, if the 50 $\mu$L liquid test sample were instead contained in a stagnant annular volume surrounding the sensing element 37 that was incubated, a corresponding 50% recovery of the target material onto the outer surface of the sensing element 37 may take approximately 1 hour. Thus, the invention illustrated in FIGS. 11–12 offers a dramatic reduction in the analysis time on the order of about 20 times.

This example shows the improvements in the efficiency with which the target material may be stripped from the liquid test sample by the continuous flow, narrow annular flow channel 45 approach illustrated in FIGS. 11–12, as compared to a conventional incubation strategy. Other continuous flow designs of comparable or better performance can be similarly designed using the graph of FIG. 18.

As an alternative construction to that illustrated in FIGS. 11–12, the capillary tube 43 may be eliminated and the narrow flow channel 45 may be defined directly between the sensing element 37, the walls of a suitably sized sensor channel 80–86, and the cover 16.

As a further alternative, the sensing element 37 may have any other suitable cross-sectional geometric configuration besides circular, such as elliptical, triangular, square, rectangular, etc. In such a case, the corresponding cross-sectional configuration of the narrow flow channel 45 may also be elliptical, triangular, square, rectangular, etc., and may be defined by corresponding portions of the sensor channel 80–86 and the cover 16, or by a suitable capillary tube 43 having the desired corresponding internal cross-sectional configuration.

MASS TRANSFER ENHANCEMENT, NON-CORRESPONDING CROSS-SECTIONAL SHAPES (FIG. 13):

Referring now to FIG. 13, it has been discovered that a mass transfer enhancement means for increasing the rate at which the target material in a liquid test sample may reach the surface of sensing element 37 may comprise utilizing a sensing element 37 on the one hand, and a sensor channel 80–86/cover 16 combination on the other hand, that have non-corresponding cross-sectional shapes. Alternatively, the cover 16 may be eliminated, and the cross-sectional shape defined by the sensor channel 80–86/cover 16 combination may be defined entirely by the main body 12, by making the sensor channel 80–86 in the form of a tubular, closed figure in the main body 12.

As used herein "non-corresponding cross-sectional shapes" may be broadly defined as comprising two shapes that are selected such that: (a) they are located one inside of the other, and a flow channel 45*a* is defined between them; (b) the flow channel 45*a* has a non-uniform width as one travels completely about the periphery of the sensing element 37; and (c) turbulent flow is generated by the two shapes as a test fluid flows down the longitudinal length of the flow channel 45*a*.

Examples of such "non-corresponding cross-sectional shapes" may be: (1) two shapes that are different in form from each other, such as a triangle and a circle, or a triangle and a square; (2) two concentric shapes that are the same in form, but different in size, such as two concentric equilateral triangles or two concentric squares; (3) two shapes that are the same in form, but are arranged off-center with respect to each other, such as two non-concentric circles, or two non-concentric equilateral triangles; (4) two shapes that are the same in form, but are rotated with respect to each other, such as two ellipses rotated 90° with respect to each other, or two equilateral triangles rotated 60° with respect to each other; and (5) any combination of the foregoing four examples.

A sensing element 37 on the one hand, and a sensor channel 80–86/cover 16 combination on the other hand, having such non-corresponding cross-sectional shapes may be used to create an unstable or turbulent flow of the liquid test sample within their flow channel 45*a*, as the liquid test sample flows down the longitudinal length of the flow channel 45*a*. Such unstable or turbulent flows may generate secondary circulation flow patterns 47 within the flow channel 45*a* that may carry the target material directly to, and across, the surface of the sensing element 37, where it may promptly interact with the sensing element 37, such as by binding to the antibodies on the surface of the sensing element 37.

A continuous flow of the liquid test sample down the flow channel 45*a* may not be necessary for this mass transfer enhancement technique to be of value. This is because a small increment in the flow of the liquid test sample may be sufficient to activate the secondary flow patterns 47, so that previously stagnant fluid zones within the flow channel 45*a* having high concentrations of the target material are moved into close proximity to the outer surface of the sensing element 37.

By way of example, as seen in FIG. 13 such non-corresponding cross-sectional shapes may comprise a circular shape defined by the sensing element 37, and an equilateral triangular shape defined by the sensor channel 80–86/cover 16 combination. As was explained above, such non-corresponding cross-sectional shapes may create an unstable or turbulent flow of the liquid test sample within the flow channel 45*a* that is defined between the sensing element 37 and the sensor channel 80–86/cover 16 combination, as the liquid test sample flows down the length of the flow channel 45*a*. Such unstable or turbulent flow may generate secondary circulation flow patterns 47 within the flow channel 45*a* that may carry the target material directly to, and across, the surface of the sensing element 37, where it may promptly interact with the sensing element 37, such as by binding to the antibodies on the surface of the sensing element 37.

It should be noted that the flow of the liquid test sample down the flow channel 45*a* need not be strictly turbulent in order to give rise to some degree of secondary flow patterns 47. Accordingly, as an alternative, it may be acceptable for the fluidic circuit card 10 to be operated at flow rates lower than those required for strictly turbulent operation.

Alternatively, instead of the sensing element 37 and the sensor channel 80–86/cover 16 combination having the same respective non-corresponding cross-sectional shapes down their entire lengths, the sensing element 37 and/or the sensor channel 80–86/cover 16 combination may have respective non-corresponding cross-sectional shapes that vary as one travels down their respective lengths.

Alternatively, the cross-sectional shape of the sensing element 37 may comprise any other geometric shape having curved sides, such as an ellipse; having straight sides, such a triangle, a square, a rectangle, a pentagon, etc.; or having any combination of straight and curved sides. Similarly, the cross-sectional shape of the sensor channel 80–86/cover 16 combination may comprise any other geometric shape having straight sides, such an a non-equilateral triangle, a square, a rectangle, a pentagon, etc.; having curved sides, such as a circle or an ellipse; or having any combination of straight and curved sides.

In general, it may be said that the mean Reynold's number for the particular non-corresponding cross-sectional shapes for the sensing element 37 and the sensor channel 80–86/cover 16 combination under consideration should be above that required for nominally turbulent flow down their respective flow channel 45*a*.

MASS TRANSFER ENHANCEMENT, DIVERGING AND/OR CONVERGING NOZZLE SHAPES (FIGS. 14–17):

Referring now to FIGS. 14–17, it has been discovered that a mass transfer enhancement means for increasing the rate at which the target material in a liquid test sample may reach the surface of the sensing element 37 may comprise locating the sensing element 37 within a sensor channel 80–86 that may comprise one, or more, diverging and/or converging nozzle shapes.

It is known that fluid flow out of a diverging nozzle is only conditionally stable, and that at comparatively small nozzle half-angles and flow velocities turbulent circulation patterns may be set up within the fluid flowing through a diverging nozzle. A nozzle half angle may be defined as the angle made between the nozzle's axis and a line parallel to the nozzle's wall.

As seen in FIGS. 14–15, the sensor channel 80–86 may comprise three diverging/converging nozzles 49, although there may be fewer, or more, of such nozzles 49. Each nozzle 49 may have a truncated, conical shape. Alternatively, although the nozzles 49 are illustrated as each comprising one-half (i.e., 180°) of a truncated cone, they may each comprise a greater, or lesser, portion of a truncated cone. Alternatively, the nozzles 49 may comprise any other diverging and/or converging shape other than conical, and may be repeated along the length of the sensor channel 80–86.

If the flow of the liquid test sample is from right to left in FIG. 14, then nozzles 49 may be considered to be diverging nozzles 49, and may easily generate the desired turbulent secondary circulation patterns 51.

In general, for a diverging nozzle 49 with a half-angle of 5°, turbulent, back-flow patterns 51 are generated for Reynolds numbers below approximately 700. As the half-angle increases, initiation of turbulent, back-flow patterns 51 occurs at lower Reynolds numbers. Locally, back-flow patterns 51 occur at the wall of any particular diverging nozzle 49 when the rate-of-change in the radius of the cross-section of the diverging nozzle 49, as one travels down the axis of the diverging nozzle 49, exceeds 12/Re, where Re is the Reynold's number based on the mean flow velocity of the liquid test sample down the sensor channel 80–86, and the mean diameter of the sensor channel 80–88.

Alternatively, if the flow of the liquid test sample were from left to right in FIG. 14, then the nozzles 49 may be considered to be converging nozzles 49. While converging nozzles 49 are generally more stable as to flow profiles than diverging nozzles 49, converging nozzles 49 may still generate the desired turbulent secondary circulation patterns 51 (which may be similar to the circulation patterns 51 for the diverging nozzles 49, but which may circulate in the opposite direction). But whether the nozzles 49 are diverging or converging, the turbulent secondary circulation patterns 51 that they generate may carry the target material directly to, and across, the surface of the sensing element 37, where it may promptly interact with the sensing element 37, such as by binding to the antibodies on the surface of the sensing element 37.

As an alternative to the arrangement of the nozzles 49 seen in FIG. 14, (in which all of the nozzles 49 point in the same direction), the nozzles 49 may be arranged in any sequence of diverging and converging nozzles 49. As a result, a fluid flowing constantly through such a channel 80–86 in the same direction (whether from right to left, or left to right) would encounter both diverging and converging nozzles 49.

Referring now to the alternative embodiment illustrated in FIGS. 16–17, it is seen that the sensor channel 80–86 may comprise four diverging/converging nozzles 53–59, although there may be fewer, or more, of such nozzles 53–59. Although the nozzles 53–59 are illustrated as comprising one-half (i.e., 180°) of a figure of revolution that may be generated by rotating a sinusoidal wave form about the longitudinal axis of the sensing fiber 37, they may each comprise a greater, or lesser, portion of such a figure of revolution; and any other suitable wave form besides sinusoidal may be used to generate the figure of revolution.

If the flow of the liquid test sample is from right to left in FIG. 16, then the nozzles 53 and 57 may be considered to be diverging nozzles, the nozzles 55 and 59 may be considered to be converging nozzles, and the nozzles 53–59 may generate the desired turbulent secondary circulation patterns 61. On the other hand, if the flow of the liquid test sample were from left to right in FIG. 16, then the nozzles 59 and 55 may be considered to be diverging nozzles, the nozzles 57 and 53 may be considered to be converging nozzles, and may generate the desired turbulent secondary circulation patterns which may be similar to the circulation patterns 61, but which may circulate in the opposite direction. The turbulent secondary circulation patterns 61 may carry the target material directly to, and across, the surface of the sensing element 37, where it may promptly interact with the sensing element 37, such as by binding to the antibodies on the surface of the sensing element 37.

The onset, and direction, of the secondary flow patterns 61 of the FIGS. 16–17 embodiment will occur under conditions similar to those discussed above for the FIGS. 14–15 embodiment.

MASS TRANSFER ENHANCEMENT, LIQUID TEST SAMPLE HAVING A CROSS-FLOW COMPONENT (FIGS. 18–19):

It has been discovered that a mass transfer enhancement means for increasing the rate at which the target material in a liquid test sample may reach the surface of sensing element 37 may comprise utilizing a sensor channel 80–86 and a sensing element 37 that follow respective paths selected such that a liquid test sample flowing down the sensor channel 80–86 may have, in at least some portions of its travel down the sensor channel 80–86, a cross-flow component with respect to the longitudinal axis of the sensing element 37.

A "cross-flow component" may be defined as a vector component of the flow of the liquid test sample that is at a right angle with respect to a corresponding portion of the longitudinal axis of the sensing element 37. Such a cross-flow component of the liquid test 28 sample may be desirable since it may carry the target material directly to, and across, the surface of the sensing element 37, where it may promptly interact with the sensing element 37, such as by binding to the antibodies on the surface of the sensing element 37.

Such a cross flow component for the liquid test sample may be generated in a variety of ways.

For example, as seen in FIGS. 18–19, the sensor channel 80–86 may follow a sinuous path 63 with respect to the longitudinal axis of a straight sensing element 37. As a result, the liquid test sample may be forced to flow in a sinuous flow path 65 with respect to the longitudinal axis of the sensing element 37. As seen in FIG. 18, at the six portions 67 on the sinuous flow path 65, where the liquid test sample may be forced to flow across the sensing element 37, the flow of the liquid test sample may have a cross-flow component with respect to the longitudinal axis of the sensing element 37.

The effectiveness of the mass transfer enhancement that occurs when the above cross-flow component invention is utilized is truly remarkable, when compared to how slowly the target antigens (or other target material) in the liquid test sample travel to the sensing element 37 by simple diffusion, as in conventional batch protocols.

For example, let it be assumed that the target material comprises molecules having about a 40,000 MW; that the target material is carried in a water solution at about 20° C.; that longitudinal axis of the sensing element 37 and the longitudinal axis of its sensor channel 80–86 are locally displaced with respect to each other by only 10°; and that the mean flow velocity of the liquid test sample is about 5.8 mm/min. Under these conditions, it may be calculated that the number of target material molecules reaching the surface of the sensing element 37 will be about 62.5 times greater than the number of target material molecules that would reach the surface of the sensing element 37 by simple diffusion, such as when conventional stagnant incubation protocols are used.

The desired cross flow component for the liquid test sample flowing in the sensor channel 86 may be generated in several alternative ways, other than using a sinuous sensor channel 80–86 and a straight sensing element 37.

For example, both the sensor channel 80–86 and the sensing element 37 may be straight, but their respective axes may be oriented at an angle with respect to each other, so that a liquid test sample flowing down the sensor channel 80–86 may have the desired cross-flow component. Alternatively, the sensor channel 80–86 may be straight, and the sensing element may follow a sinuous, helical, or other curved path within the sensor channel 80–86. Alternatively, both the sensor channel 80–86 and the sensing element 37 may follow respective curved paths.

The effectiveness of a particular cross-flow geometry may be estimated by calculating the enhancement ratio:

$$RV_p/D \tag{2}$$

where R is the radius of the flow channel defined between the sensing element 37 and its sensor channel 80–86; $V_p$ is the mean flow velocity component of the liquid test sample that is perpendicular to the sensing element 37's longitudinal axis; and D is the diffusion coefficient of the target material in the liquid test sample. If the enhancement ratio is significantly greater than 1.0, then large improvements in mass transfer rates can be expected for the particular cross-flow geometry under consideration.

MASS TRANSFER ENHANCEMENT, FLOW CHANNEL WITH DEFORMABLE WALL (FIGS. 20–21):

It has been discovered that a mass transfer enhancement means for increasing the rate at which the target material in a liquid test sample may reach the surface of sensing element 37 may comprise a sensor channel 80–86 having a least one deformable wall, and means for moving at least a portion of that deformable wall with respect to the sensing element 37. As the deformable wall is moved with respect to the sensing element 37, a cross-flow component of the liquid test sample flowing down the sensor channel 80–86 may be generated with respect to the longitudinal axis of the sensing element.

A "cross-flow component" may be defined, in the context of

FIGS. 20–21, as a vector component of the movement of the liquid test sample that is at a right angle with respect to a corresponding portion of the longitudinal axis of the sensing element 37. Such a cross-flow component of the liquid test sample may be desirable since it may carry the target material directly to, and across, the surface of the sensing element 37, where it may promptly interact with the sensing element 37, such as by binding to the antibodies on the surface of the sensing element 37.

By way of example, as seen in FIGS. 20–21, the portion 69 of the cover 16 that overlies the sensor channel 80–86 may form a deformable wall for the sensor channel 80–86; and a piezoelectric transducer 71 may be provided to move at least a portion of the deformable wall 69 at a right angle with respect to the longitudinal axis of the sensing element 37, in order to generate the desired cross-flow component of the liquid test sample with respect to the sensing element 37. The deformable wall 69 and/or the transducer 71 may be sized so as to extend over part, or all, of the length and/or width of the sensing element 37.

Alternatively, any other wall of the sensor channel 80–86 may be made deformable, and the transducer 71 may be located so as to move such other wall with respect to the sensing element 37 in the desired fashion.

Alternatively, the wall 69 may not be deformable, and the transducer 71 may be tuned to so as to cause the sensing fiber 37 to resonate, or vibrate, while it is immersed in the liquid test sample flowing through the sensor channel 80–86. Such vibrations of the sensing fiber 37 within the liquid test sample may cause the desired cross-flow component of the liquid test sample with respect to the sensing element 37. Here, however, instead of moving the liquid test sample with respect to the sensing element 37, the sensing element 37 is being moved (vibrated), with respect to the liquid test sample. Accordingly, the term "cross-flow component" is further defined to include such movement or vibration of the sensing element 37 with respect to the liquid test sample.

Alternatively, instead of the piezoelectric transducer 71, any other suitable actuating means may be used to move the deformable wall 69, such as any suitable electrical, magnetic, mechanical, pneumatic or hydraulic actuating means.

Essentially, the FIGS. 20–21 embodiment is another way of providing a flow velocity component of the liquid test sample that is perpendicular to the sensing element 37's longitudinal axis. Thus, the enhancement ratio given by equation 2 above for the FIGS. 18–19 embodiment is also a measure of the effectiveness of the FIGS. 20–21 embodiment, except that the perpendicular flow velocity is now created by a deformable wall of the fluidic circuit card 10, or by vibration of the sensing element 37.

The extent of the perpendicular component of the flow of the liquid test sample or the lateral movement of the sensing element 37 that is required to provide enhanced mass transfer may also be estimated by calculating the value of the dimensionless factor:

$$Dt/H^2 \tag{3}$$

where D is the diffusion coefficient of the target material in the liquid test sample; t is the total assay time; and H is the amount the liquid test sample or the sensing element 37 is moved laterally. If the equation 3 factor is less than or equal to about 0.5, then the lateral translation H should improve mass transfer rates.

MASS TRANSFER ENHANCEMENT, ASYMMETRIC PRESSURE FIELDS (FIG. 22):

It has been discovered that a mass transfer enhancement means for increasing the rate at which the target material in a liquid test sample may reach the surface of sensing element 37 may comprise utilizing asymmetric pressure fields with respect to the sensing element 37. Such asymmetric pressure fields may cause the liquid test sample flowing down the sensor channel 80–86 to have a cross-flow component with respect to the longitudinal axis of the sensing element 37.

A "cross-flow component" may be defined, in the context of FIG. 22, as a vector component of the movement of the liquid test sample that is at a right angle with respect to a corresponding portion of the longitudinal axis of the sensing element 37. Such a cross-flow component of the liquid test sample may be desirable since it may carry the target material directly to, and across, the surface of the sensing element 37, where it may promptly interact with the sensing element 37, such as by binding to the antibodies on the surface of the sensing element 37.

By way of example, one means for generating the desired asymmetric pressure fields with respect to the sensing element 37 is illustrated in FIG. 22. As seen in FIG. 22, a piezoelectric transducer 73 may be used to produce an acoustic beam that propagates into the body 12. The transducer 73 may be sized so as to extend over part, or all, of the length and/or width of the sensing element 37.

As is also seen in FIG. 22, the transducer 73 may be positioned to one side of the longitudinal centerline of the sensing element 37, to help ensure that the fluid in the cavity 80–86 is asymmetrically irradiated with acoustic energy. However, as an alternative, the transducer 73 may be symmetrically positioned with respect to the longitudinal centerline of the sensing element 37.

At the interior surface of the sensor channel 80–86, the acoustic beam may be diffracted, as seen, due to the large difference in the acoustic properties between the body 12 and the liquid test sample flowing within the sensor channel 80–86. This interfacial diffraction, as well as the curved shape of the sensor channel 80–86, may produce a focusing effect on the acoustic beam with the sensor channel 80–86, as shown, before the acoustic beam subsequently scatters off the sensing element 37 and is dissipated within the body 12.

The asymmetric concentrations of acoustic energy within the sensor channel 80–86 may produce the desired asymmetric pressure fields with respect to the sensing element 37. The desired asymmetric pressure fields may, in turn, cause the liquid test sample flowing down the sensor channel 80–86 to have a cross-flow component that is at a right angle with respect to the longitudinal axis of the sensing element 37.

Alternatively, instead of the piezoelectric transducer 73, any other suitable means for producing the desired asymmetric pressure fields may be utilized, such as any suitable acoustical, electrical, magnetic, mechanical, pneumatic or hydraulic pressure producing means.

The following numerical factors may at least partially define the scope of the asymmetric pressure field mass transfer enhancement means of the present invention: (a) the transducer 73 may vibrate at a rate in the range of about 10 KHz to about 2 MHz; (b) the sensing element 37 may have a diameter in the range of about 100–1,000 microns; (c) the sensing element 37, the sensor channel 80–86, and/or the transducer 71 may have a length in the range of about 0.10–30.0 mm; (d) the sensor channel 80–86 and/or the transducer 71 may have a width in the range of about 1–2 mm; (e) the sensor channel 80–86 may have a depth in the range of from about 1–2 mm; (f) the sensor channel 80–86 may have any suitable cross-sectional shape, such as circular, D-shaped, square, rectangular, and elliptical; and (g) the flow velocity of the liquid test sample through the sensor channel 80–86 may be in the range of about 0.00–10 cm/min.

FLUIDIC CIRCUIT CARD 100 (FIGS. 23–27)

Turning now to FIGS. 23–27, they illustrate a second embodiment 100 of the fluidic circuit card of the present invention. The fluidic circuit card 100 may be the same as, or at least similar to, the fluidic circuit card 10 of FIGS. 1–22 with respect to its theory, construction and operation, except for those differences which will be made apparent by the disclosures herein.

Accordingly, for clarity and simplicity, certain parts of the fluidic circuit card 100 of FIGS. 23–27 have been given the same reference numerals, with an "a" appended, as the reference numerals used for the corresponding respective parts of the fluidic circuit card 10 of FIGS. 1–22.

The term "fluid" as used herein regarding the fluidic circuit card 100 is defined to encompass both liquids and gases, unless the context should clearly indicate otherwise.

All of the components of the fluidic circuit card 100 may be made from materials that are selected to be compatible with the various fluids with which any particular fluidic circuit card 100 may be intended to be used.

Although not illustrated, for clarity, the fluidic circuit card 100, like the fluidic circuit card 10, may be provided with a reflective strip 18*a*, and may used with at least one light source 91 and photodetector 93 pair, in either a reflective system or a transmissive system, to detect the presence of liquids and bubbles within the fluidic circuit card 100, in a manner similar to that described in detail above regarding the fluidic circuit card 10. Although also not illustrated, for clarity, the fluidic circuit card 100 may be provided with at least one window 33 which may be used with a reflective strip 18*a* and/or with at least one light source 91 and photodetector 93 pair, in either a reflective or a transmissive system, for encoding information on the fluidic circuit card 100, in a manner similar to that described in detail above regarding the fluidic circuit card 10.

Referring now to FIGS. 23–27, which are drawn to scale, the fluidic circuit card 100 may comprise a main body 12*a*; a cover 16*a*; a first needle septum strip 20*a*; a second needle septum strip 20*b*; an adhesive strip 22*a*; a valve membrane strip 24*a*; a front face 76*a*; a back face 78*a*; four valves 102–108, each having a respective inlet port 110–116 and a respective outlet port 118–124; seven channels 126–138; four fluidic card ports 140–146; a sensor housing means in the form of a sensor cavity 148; a sensor cavity plug 150; an O-ring seal 152 for the plug 150; a sensing element comprising a sensing membrane 154; and a filter 156. It should be noted that the channel 126 is not in direct fluid communication with the sensor cavity 148.

The needle septum strip 20*b*, which may be the same as the needle septum strip 20*a*, except for size, may be adhered to the main body's front face 76*a* and disposed in a rectangular window 158 in the cover 16*a* over the channel 126; in order to permit fluids to be injected into, or withdrawn from, the channel 126 through the cover 16*a* and the needle septum strip 20*b*.

As an alternative, the needle septum strip 20*a* may be eliminated, such as if the external equipment with which the fluidic circuit card 100 was to be used was provided with suitable means for sealing the fluidic card ports 140–146. Similarly, the needle septum strip 20*b* may also be eliminated, such as if the external equipment with which the fluidic circuit card 100 was to be used was provided with suitable means for sealing the entry point of an external needle or probe through the cover 16*a* into the channel 126.

The valves 102–108 of the fluidic circuit card 100 may be the same as the valves 42–46 of the fluidic circuit card 10 in their physical construction and operation. The fluidic card ports 140–146 of the card 100 may be the same as the fluidic card ports 26–40 of the card 10 in their physical construction and operation. The channels 126–138 of the card 100 may be the same as the channels 1, 7, 11, 60–74 and 80–86 of the card 10 in their physical construction and operation.

Figure 23:
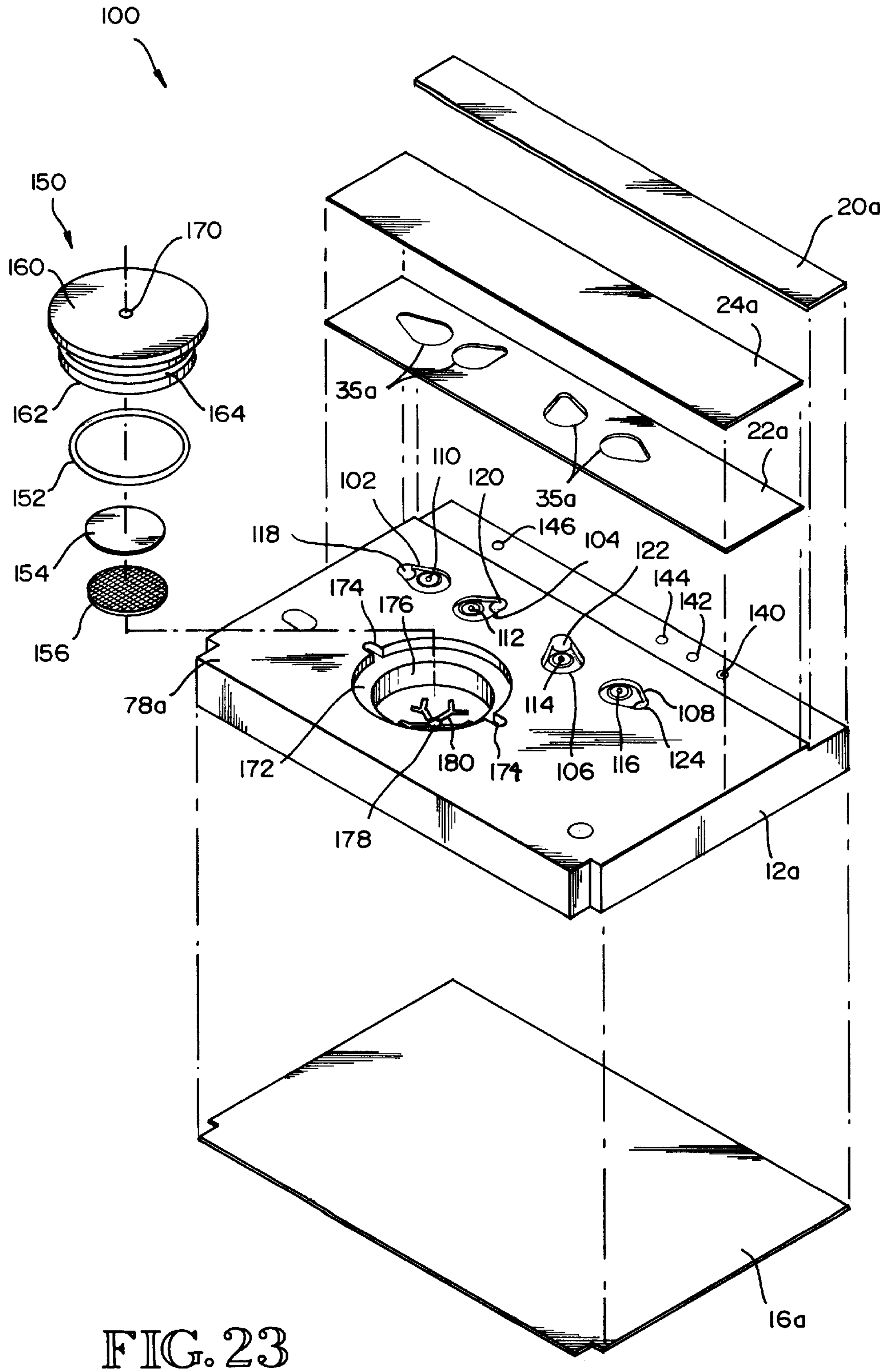
FIG. 23 is an exploded back perspective view of a second embodiment 100 of a disposable fluidic circuit card of the present invention.
Figure 26:
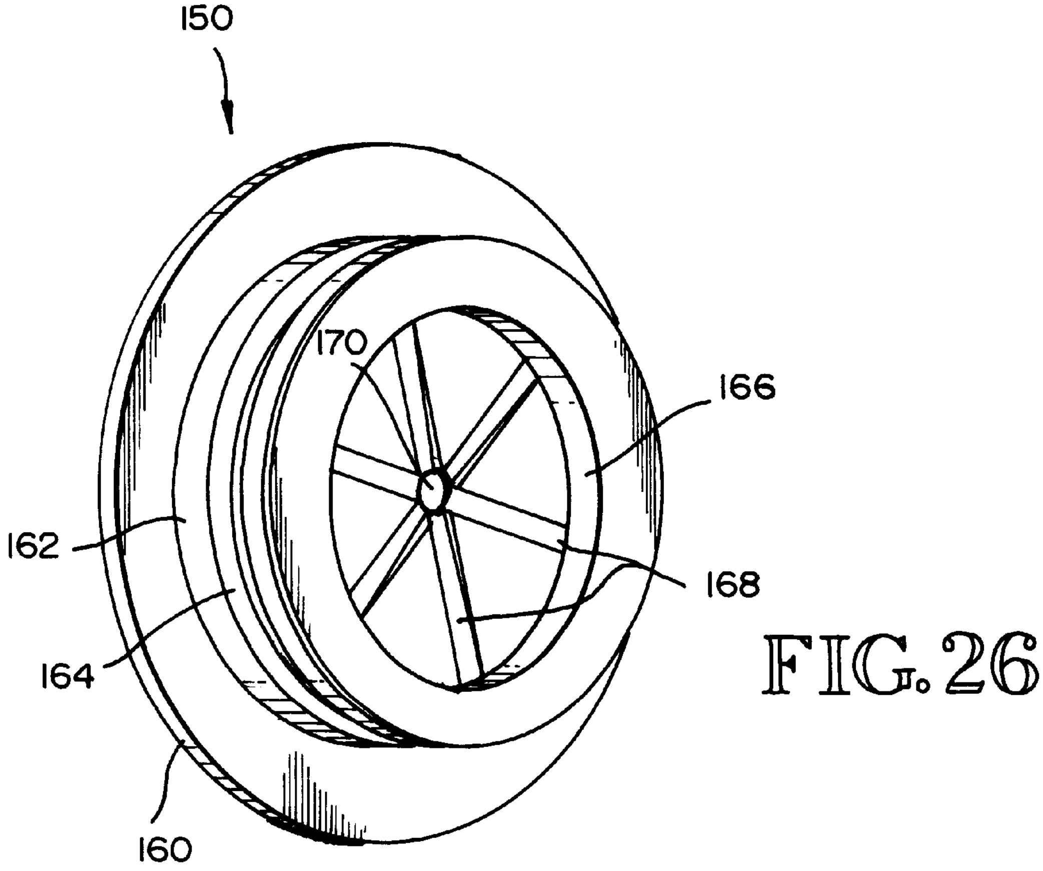
FIG. 26 is an enlarged perspective view of the sensor cavity plug 150 of FIG. 23.
Figure 27:
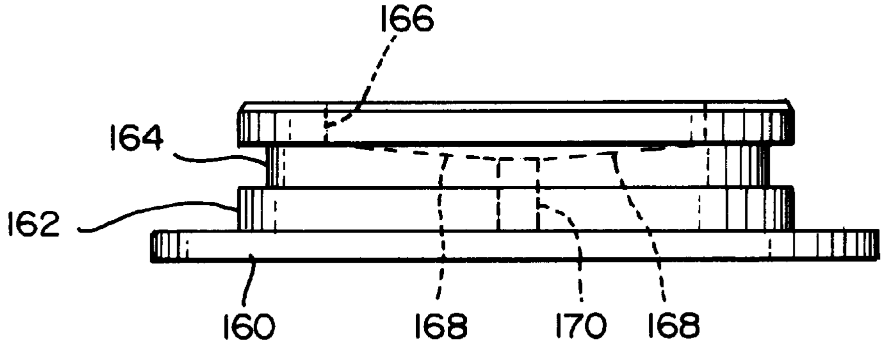
FIG. 27 is a side elevational view thereof.

As best seen in FIGS. 23, 26 and 27, the plug 150 may comprise a top 160; a neck 162; an o-ring recess 164 in the neck 162 for the o-ring 152; a cylindrical cavity 166 that may be sized to snugly receive the sensing membrane 154 and the filter 156; six drainage channels 168; and an outlet port 170.

To assemble the plug 150, the o-ring 152 may be slipped over the neck 162 and seated in its recess 164; the sensing membrane 154 may be seated in the bottom of the cavity 166 over the drainage channels 168; and the filter 156 may be seated in the cavity 166 over the sensing membrane 154. Preferably, the sensing membrane 154 and the filter 156 are sized to snugly fit the cavity 166, to help prevent any leakage of the liquid test sample around their peripheries. Such leakage may also be prevented by the use of any suitable sealant to seal the peripheries of the sensing membrane 154 and the filter 156 to the peripheral wall of the cavity 166.

As an alternative, the filter 156 may be eliminated; in which event the liquid test sample may be filtered before being introduced into the fluidic circuit card 100, or the sensing membrane 154 (or the entire plug assembly 150), may be simply replaced should the sensing membrane 154 become clogged with debris.

As best seen in FIGS. 23–25, the sensor cavity 148 may comprise an annular recess 172 sized to receive the plug 150's top 160; two recesses 174, which may be used in conjunction with any suitable external tool to lever the plug 150 out of the sensor cavity 148, when desired; a cylindrical cavity 176 sized to receive the plug 150's neck 162, and sized to make sealing contact with the plug 150's o-ring 152 when the plug 150 is installed in the sensor cavity 148; an inlet port 178; and six Y-shaped inlet channels 180 in the bottom of the cavity 176. When the plug 150 is installed in the sensor cavity 148, the outer surface of its top 160 may be flush with the back surface 78*a* of the main body 12*a*.

By way of example, the various parts of the fluidic circuit card 10 may have the following dimensions.

The main body 12*a* may be about 1.75 inches long; about 2.6 inches wide; and about 0.25 inches thick. The fluidic card ports 140–146 may each be cylindrical, have a diameter of about 0.063 inches and a length of about 0.24 inches. The valves 102–108 may have the dimensions set forth above by way of example for the valves 42–46 of the card 10. The channels 126–138 may be U-shaped, may be about 0.080 inches wide, may have a maximum depth of about 0.080 inches, and may have a bottom that is semi-circular in cross-section.

Regarding the sensor cavity 148, its annular recess 172 may have an inner diameter of about 0.59 inches, an outer diameter of about 0.75 inches, and a depth of about 0.030 inches; its cylindrical cavity 176 may have a diameter of about 0.59 inches, and a depth of about 0.15 inches; and its inlet port 178 may have a diameter of about 0.055 inches.

The cover 16*a* may be about 2.6 inches wide, about 1.75 inches long, and about 0.010 inches thick. The needle septum strip 20*a* may be about 0.25 inches wide, about 2.6 inches long, and about 0.032 inches thick. The needle septum strip 20*b* may be about 0.32 inches wide, about 0.41 inches long, and have a thickness in the range of about 0.010–0.032 inches. The adhesive layer 22*a* may be about 0.5 inches wide, about 1.75 inches long, and have a thickness in the range of about 0.001–0.005 inches. The valve membrane strip 24*a* may be about 0.25 inches wide, about 2.6 inches long, and have a thickness in the range of about 0.0003–0.001 inches.

Regarding the plug 150, it may be sized to fit within the sensor cavity 148; its cavity 166 may be about 0.38 inches wide and about 0.050 inches deep; and its outlet port may have a diameter of about 0.063 inches.

The card 100, and any of its foregoing components, have any other suitable size and shape. Similarly, there may be fewer, or more, of any of the card 100's various foregoing components; and any of the card 100's various foregoing components may be arranged differently with respect to each other.

Regarding the filter 156 it may, by way of example, comprise a disc about 0.38 inches in diameter and about 0.045 inches thick; and may be made from any suitable filter material such as Porex X4588 manufactured by Porex Technologies, located in Fairburn, Ga. The filter 156 may have any other suitable size and shape, and may comprise more than one layer of material. There may be more than one filter 156.

Regarding the sensing membrane 154 it may, by way of example, comprise a disc about 0.38 inches in diameter and about 0.005 inches thick made from any suitable membrane material, such as Immunodyne ABC membrane, manufactured by Pall Biosupport Division, located in Port Washington, N.Y. The sensing membrane 154 may have any other suitable size and shape, and may comprise more than one layer of material. There may be more than one sensing membrane 154.

If the sensing membrane 154 is to be used in performing immunoassays, such as to detect the explosive TNT, any suitable antibody of choice may be used that is specific for TNT. The antibody may be immobilized on the top, bottom and interior surfaces of the sensing membrane 154 in any suitable way, such as by conventional covalent binding techniques.

Alternatively, the sensing membrane 154 may be replaced by a layer of bead-type biosupport medium, such as MSX-350, manufactured by the 3M Corporation. A filter media or porous film may be employed on the top and bottom surfaces of the layer of bead-type biosupport medium, to prevent the beads from being carried away by the flow of the liquid test sample passing through the fluidic card 100.

An antigen of choice, such as TNT, may then be tagged with a fluorescent dye of choice, such as CY5, manufactured by Jackson Immunoresearch Laboratories, Inc. of West Grove, Pa. The antigen may be fluorescent dye-tagged in any suitable way, such as by conventional covalent binding techniques. The fluorescent dye-tagged antigen may then be bound to the antibodies on the sensing membrane 154 in any suitable way, such as by immersing the membrane 154 in a solution of tagged antigen for a period of several hours.

During use of such a sensing membrane 154, the target antigens (or other target material) in the liquid test sample may bind to the antibodies on the outer surface of the sensing membrane 154. The presence, or the amount of, the displaced fluorescent dye-tagged antigens may then be detected in the fluid leaving the membrane 154 through the outlet port 170 in any suitable way, such as by the use of any suitable external detection apparatus, such as a conventional fluorimeter. In general, the number of displaced fluorescent dye-tagged antigens, and the signal they may produce in the external detection apparatus, may be a function of the presence, or the amount of, the target material in the liquid test sample.

If the first use of the sensing membrane 154 does not displace all of the fluorescent dye-tagged antigens from the sensing membrane 154, the sensing membrane 154 may be used to perform additional tests, at least until all of the antibodies on the sensing membrane 154 have been bound. Up to 25–50 measurements may be made with the sensing membrane 154 before the membrane 154 is exhausted.

After the sensing membrane 154 has been depleted of its fluorescent dye-tagged antigens, it may be replaced in three different ways. First, the entire plug 150 may be considered to a disposable item, in which case the old plug 150 with its depleted sensing membrane 154 may be removed from the sensor cavity 148, and then be replaced with a new plug 150 having a new sensing membrane 154. Second, the plug 150 may be removed from the sensor cavity 148, the filter 156 and the depleted sensing membrane 154 may be removed from the plug 150, a new sensing membrane 154 and filter 156 may be inserted into the plug 150, and the plug 150 may then be inserted into the sensor cavity 148. Third, a reagent containing tagged antibody may be flowed into the fluidic circuit card 100, and replenishment of the depleted sensing membrane 154 may be attained by displacement that occurs during incubation in the reagent solution.

THE OPERATION OF THE FLUIDIC CIRCUIT CARD 100:

The operation of the fluidic circuit card 100 will now be described. In general, any of the fluidic card ports 140–146 may handle the input and/or output of any desired fluid, and the fluidic card ports 140–146 may be connected with each other by the valves 102–108 in a variety of ways. Accordingly, the following descriptions of the operation of the fluidic circuit card 100 are only a few examples of the many ways in which it might be operated.

The valves 102–108 may all be normally open, due to the tension in their valve membranes 29*a*; and may be closed by any suitable externally applied closure force applied to their valve membranes 29*a*. Thus, when the following description indicates that any of the valves 102–108 are opened, that may mean either that an already open valve 102–108 is left open, or that a closed valve 102–108 is opened by ceasing to apply the externally applied closure force that acts on its valve membrane 29. Similarly, when the following description indicates that any of the valves 102–108 are closed, that may mean either that an already closed valve 102–108 is left closed, or that an open valve 102–108 is closed by applying a suitable externally applied closure force to its valve membrane 29*a*.

If a liquid test sample is to be injected into the card 100 through the port 140, the valves 104 and 108 may be closed, and the valve 102 may be opened. The injected liquid test sample may then sequentially travel through the port 140, the channel 126, the valve 102, the channel 136, the valve 102, the channel 138, and the liquid waste outlet port 146.

Meanwhile, a stable measurement baseline has been created by simultaneously opening the valve 106 and flowing a buffer, such as a phosphate buffered saline solution, through the system from the buffer inlet port 144, through the channels 132 and 134, through the sensor cavity 148, and to the external analyzing instrument via the outlet port 170 in the plug 150.

To perform the core assay procedure, the valves 102, 106 and 108 are closed, the valve 104 is opened, and the buffer is introduced into the fluidic circuit card 100 through the port 140. Alternatively, the port 142 may be used if the valve 108 is opened. This buffer pushes the volume of the liquid test sample in the channel 126 through the valve 104 and the channel 134 into the sensor cavity 148, and on to the external analyzing instrument via the outlet port 170 in the plug 150. The amount of the liquid test sample that is stored in the channel 126 may typically be in the range of about 50–250 μL. As the liquid test sample flows through the sensing membrane 154, a fraction of any antigen in the test sample displaces fluorophor-tagged antigen from the membrane 154. This fluorescent species can then be detected in the external analyzing instrument using standard fluorimeter techniques.

Alternatively, other tagging and detection techniques may be employed. For example, the tagged antigen may have an absorbing molecular species bonded to it and an absorbance-based spectrometer may be used to determine the amount of the target material that is present in the liquid test sample. It may also be possible to use magnetic, radioactive, electrochemical or diverse tags to meet a specific assay requirement.

Undesired back flow of the liquid test sample through the channels 128 and 136 may be prevented by permanent valves comprising part of the companion instrument with which the fluidic circuit card 100 is intended to interface.

Alternatively, instead of injecting the liquid test sample into the port 140, it may be injected directly into the channel 126 through the needle septum strip 26*b* that may be located on the front of the card in the rectangle labeled 158. Undesired back flow of the liquid test sample through the port 140 and channel 128; and through the channel 136 may be prevented by permanent valves comprising part of the companion instrument with which the fluidic circuit card 100 is intended to interface.

Prior to injecting a liquid test sample into the card 100, a calibration sample (containing a known amount of the target material), may be injected into the port 140, or into the channel 126 via the needle septum strip 126*b*, and then pass though the card 100 and out its outlet port 170, in the manner described above regarding a liquid test sample. The calibration sample may be used to calibrate the external detection equipment for the particular sensing membrane 154 being used, since the calibration sample may bind a certain amount of the antibodies on the surface of the particular sensing membrane 154 being used, as a function of the known amount of the target material in the calibration sample.

Alternatively, the calibration sample may be used to verify whether or not all of the sensing membrane 154's antibodies have been bound; since if the detection equipment is unable to obtain a reading from the calibration sample, the sensing membrane 154 may be considered to have been effectively depleted of all of its fluorescent dye-tagged antigens. After the test or calibration has been completed, the card 100 may be emptied (and/or cleaned) in any suitable way. For example, the valves 102, 106 and 108 may be closed, and the valve 104 may be opened. Air may then be injected into the port 140 or 142 until all of the liquid test sample or calibration sample has been forced out through the outlet port 170. Alternatively, the valves 102 and

108 may be opened, and the valves 104 and 106 may be closed, so that the liquid test sample or the calibration sample in the channel 126 may be flushed out through the channels 130, 128, 126 and 136; the valve 102; the channel 138; and the port 146.

As indicated earlier, some sensing membranes 154 may need to be periodically treated with one or more liquid reagents containing a high concentration of tagged antigen, in order to maintain their sensitivity to the target material in the liquid test sample, for example. In order to treat the sensing membrane 154 with a reagent, the valve 104 may be opened, and the valves 102, 106 and 108 may be closed. The desired quantity of reagent may then be injected into the port 140 or the septum strip 126*b*, from which it may then travel sequentially through the channel 126, the valve 104, the channel 134, the inlet port 178, the inlet channels 180, the filter 156, the sensing membrane 154, the drainage channels 168, and the outlet port 170.

It is understood that all of the foregoing forms of the invention were described and/or illustrated strictly by way of non-limiting example.

In view of all of the disclosures herein, these and further modifications, adaptations and variations of the present invention will now be apparent to those skilled in the art to which it pertains, within the scope of the following claims.

What is claimed is:

1. A fluidic circuit card capable of performing more than one of fluid handling, fluid control, fluid sensing, and/or fluid property measurement functions; wherein said fluidic circuit card comprises:

a main body and a cover means;

wherein said main body comprises a plurality of fluidic circuit components and an interior volume; wherein said cover means is for isolating at least a portion of said interior volume from external conditions, and comprises at least one sheet of cover material applied to said main body;

wherein said fluidic circuit card provides the benefits of disporsability or non-disposability, inexpensive mass manufacture, replaceability or non-replaceability of at least one of said fluidic circuit components, compactness, and renewability or non-renewability of at least one of said fluidic circuit components;

wherein said main body further comprises one integral, molded plastic part, and an exterior surface;

wherein said plurality of fluidic circuit components comprise a main body input port; a main body output port; a sensing element; a sensor housing means for housing said sensing element; and fluid communication means for providing fluid communication among said main body input port, said main body output port, and said sensor housing means;

wherein said sensor housing means comprises at least one sensor channel;

wherein at least a portion of each of said fluidic circuit components is defined by said exterior surface of said main body; and wherein said cover means is also for covering at least a portion of said sensor housing means and said fluid communication means.

2. The fluidic circuit card according to claim 1, wherein said sheet of cover material comprises a thin sheet of material that is adhesively secured to said main body.

3. The fluidic circuit card according to claim 1, wherein said fluidic circuit card further comprises a needle septum; wherein said needle septum comprises a thin sheet of needle septum material that is adhesively secured to said main body; and wherein said needle septum comprises a seal for said main body inlet port and said main body outlet port.

4. The fluidic circuit card according to claim 1, wherein said fluidic circuit card further comprises a needle septum; wherein said needle septum comprises a thin sheet of needle septum material that is adhesively secured to said main body; and wherein said needle septum comprises a seal for at least a portion of said fluid communication means.

5. The fluidic circuit card according to claim 1, wherein said fluidic circuit card further comprises a valve;

wherein said valve comprises a valve body; a valve input port for said valve body; a valve output port for said valve body; and a valve membrane means for providing a valve membrane for said valve body;

wherein said fluidic circuit components further comprise said valve body;

wherein said valve body is defined by said exterior surface of said main body; and wherein said fluid communication means are for providing fluid communication among said main body input port, said main body output port, said sensor housing means, and said valve.

6. The fluidic circuit card according to claim 5, wherein said valve membrane means comprises a thin sheet of valve membrane material that is adhesively secured to said main body.

7. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card further comprises a valve;

wherein said valve comprises a valve body; a valve input port for said valve body; a valve output port for said valve body; and a valve membrane means for providing a valve membrane for said valve body;

wherein said fluidic circuit components further comprise said valve body;

wherein said valve body is defined by said exterior surface of said main body;

wherein said fluid communication means are for providing fluid communication among said main body input port, said main body output port, said sensor housing means, and said valve;

wherein said valve membrane means comprises a secured portion for securing said valve membrane to said main body; wherein said fluidic circuit card further comprises a thin strip of adhesive material defining a valve hole for said valve body; wherein said thin strip of adhesive material secures said secured portion of said valve membrane means to said exterior surface of said main body; and wherein said thin layer of adhesive material does not secure said valve membrane to said valve body.

8. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card further comprises a valve:

wherein said valve comprises a valve body; a valve input port for said valve body; a valve output port for said valve body; and a valve membrane means for providing a valve membrane for said valve body;

wherein said fluidic circuit components further comprise said valve body;

wherein said valve body is defined by said exterior surface of said main body;

wherein said fluid communication means are for providing fluid communication among said main body input port, said main body output port, said sensor housing means, and said valve;

wherein said valve membrane means comprises a thin sheet of heat-shrink plastic; wherein said thin sheet of heat-shrink plastic comprises a secured portion that is secured to said main body; and wherein said valve membrane comprises a heat-shrunk portion of said thin sheet of heat-shrink plastic that has been heat-shrunk to the point that said valve membrane is taut and is free from any substantial wrinkles.

9. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card further comprises a valve;

wherein said valve comprises a valve body; a valve input port for said valve body; a valve output sort for said valve body; and a valve membrane means for providing a valve membrane for said valve body;

wherein said fluidic circuit components further comprise said valve body;

wherein said valve body is defined by said exterior surface of said main body;

wherein said fluid communication means are for providing fluid communication among said main body input port, said main body output port, said sensor housing means, and said valve;

wherein said fluidic circuit card further comprises a layer of adhesive material; wherein said valve membrane means comprises a thin sheet of heat-shrink plastic; wherein said thin sheet of heat-shrink plastic comprises said valve membrane and a secured portion that is secured to said main body by said layer of adhesive material; wherein a surface of said secured portion of said thin sheet of heat-shrink plastic comprises a corona discharge changed surface; wherein said corona discharge changed surface was changed by a high voltage corona discharge in a gas comprising a suitable amount of oxygen; and wherein said corona discharge changed surface exhibits an increased adhesive bonding strength with respect to said layer of adhesive material, as compared to a non-corona discharge changed surface.

10. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card further comprises a valve;

wherein said valve comprises a valve body; a valve input port for said valve body; a valve output port for said valve body; and a valve membrane means for providing a valve membrane for said valve body;

wherein said fluidic circuit components further comprise said valve body;

wherein said valve body is defined by said exterior surface of said main body;

wherein said fluid communication means are for providing fluid communication among said main body input port, said main body output port, said sensor housing means, and said valve;

wherein said fluidic circuit card further comprises a layer of adhesive material; wherein said valve membrane means comprises a thin sheet of heat-shrink plastic; wherein said thin sheet of heat-shrink plastic comprises said valve membrane and a secured portion that is secured to said main body by said layer of adhesive material; wherein a surface of said secured portion of said thin sheet of heat-shrink plastic comprises an ionized plasma discharge changed surface; and wherein said ionized plasma discharge changed surface exhibits an increased adhesive bonding strength with respect to said layer of adhesive material, as compared to a non-ionized plasma discharge changed surface.

11. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card further comprises a valve;

wherein said valve comprises a valve body; a valve input port for said valve body; a valve output port for said valve body; and a valve membrane means for providing a valve membrane for said valve body;

wherein said fluidic circuit components further comprise said valve body;

wherein said valve body is defined by said exterior surface of said main body;

wherein said fluid communication means are for providing fluid communication among said main body input port, said main body output port, said sensor housing means, and said valve;

wherein said valve body further comprises a valve seat comprising a valve seat top surface; and wherein at least a portion of said valve seat top surface is convex, to help enable said portion of said valve seat top surface to make a good sealing contact with said valve membrane when said valve is closed.

12. The fluidic circuit card according to claim 5, wherein said valve body further comprises a valve cavity; wherein said valve cavity comprises a valve cavity floor that surrounds said valve input port; and wherein at least a portion of said valve cavity floor acts as a valve seat and seals against said valve membrane when said valve is closed.

13. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card further comprises a valve;

wherein said valve comprises a valve body; a valve input port for said valve body; a valve output port for said valve body; and a valve membrane means for providing a valve membrane for said valve body;

wherein said fluidic circuit components further comprise said valve body;

wherein said valve body is defined by said exterior surface of said main body;

wherein said fluid communication means are for providing fluid communication among said main body input port, said main body output port, said sensor housing means, and said valve;

wherein said valve body further comprises a valve seat and a valve cavity; wherein said valve seat comprises a valve seat top having a valve seat top surface area; wherein said valve cavity has a valve cavity surface area; and wherein a ratio of said valve seat top surface area to said valve cavity surface area is in the range of from about 1:5–1:20.

14. The fluidic circuit card according to claim 5, wherein said exterior surface of said main body further comprises a main body first exterior surface and a main body second exterior surface; wherein at least a substantial portion of said fluid communication means is located in said main body first exterior surface; and wherein at least a substantial portion of at least one of said main body input port, said main body output port and said sensor housing means is located in said main body second exterior surface, to provide an unusually compact fluidic circuit card.

15. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card further comprises a valve;

wherein said valve comprises a valve body; a valve input port for said valve body; a valve output port for said valve body; and a valve membrane means for providing a valve membrane for said valve body;

wherein said fluidic circuit components further comprise said valve body;

wherein said valve body is defined by said exterior surface of said main body;

wherein said fluid communication means are for providing fluid communication among said main body input port, said main body output port, said sensor housing means, and said valve;

wherein said exterior surface of said main body further comprises a main body first exterior surface and a main body second exterior surface; wherein at least a substantial portion of said fluid communication means and at least a substantial portion of said sensor housing means are located in at least one of said main body first and second exterior surfaces, to provide an unusually compact fluidic circuit card;

wherein said main body and all of said fluidic circuit components comprise shapes that are selected to permit said main body and all of said fluidic circuit components to be integrally formed in one piece from plastic in an injection mold, to help minimize the cost of said fluidic circuit card.

16. The fluidic circuit card according to claim 14, wherein said exterior surface of said main body further comprises a main body edge surface; wherein said sensor housing means comprises an access portion; wherein said access portion of said sensor housing means is located in said main body edge surface; wherein said access portion of said sensor housing means permits said sensing element to be introduced into said sensor housing means through said main body edge surface; and wherein said access portion of said sensor housing means helps to provide an unusually compact fluidic circuit card.

17. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card further comprises a valve:

wherein said valve comprises a valve body; a valve input port for said valve body; a valve output port for said valve body; and a valve membrane means for providing a valve membrane for said valve body;

wherein said fluidic circuit components further comprise said valve body;

wherein said valve body is defined by said exterior surface of said main body;

wherein said fluid communication means are for providing fluid communication among said main body input port, said main body output port, said sensor housing means, and said valve;

wherein said valve body further comprises a valve cavity and fitting means; and wherein said fitting means are for permitting said valve membrane to at least substantially empty said valve cavity when said valve is closed.

18. The fluidic circuit card according to claim 17, wherein said valve body further comprises a valve seat and a valve cavity periphery; and wherein said fitting means comprise at least one of a chamfer around said valve seat and a chamfer extending along said valve cavity periphery.

19. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluid communication means comprises at least one fluid channel having a bend and a half-width; and wherein said bend comprises a radius of curvature in the range of at least about 3–4 times said half-width, to avoid undesired trapping of a liquid in said bend when said liquid in said bend is forced out of said bend by a gas.

20. The fluidic circuit card according to claim 1, wherein said fluidic circuit card is adapted to be used with a liquid; and wherein said fluidic circuit components are selected to permit a bi-directional flow of said liquid through said fluidic circuit components, to permit said liquid to be recovered from said main body input port after said liquid has been introduced into said sensor housing means via said main body input port.

21. The fluidic circuit card according to claim 1, wherein said fluidic circuit card is adapted to be used with a liquid test sample containing a target material to be detected by said sensing element;

wherein said sensing element comprises a sensing element surface;

wherein, during use of said fluidic circuit card, there is a flow of said liquid test sample between said sensor housing means and said sensing element surface; and wherein said fluidic circuit card further comprises mass transfer enhancement means for increasing the rate at which said target material reaches said sensing element surface, to provide at least one of a reduced time for said sensing element to sense said target material and an increased sensitivity of said sensing element to said target material, as compared to if said fluidic circuit card did not comprise said mass transfer enhancement means.

22. The fluidic circuit card according to claim 21, wherein said mass transfer enhancement means comprise a narrowed portion of said sensor housing means; wherein said narrowed portion has a narrowed portion radius; wherein said sensing element surface has a sensing element surface radius; and wherein a ratio of said sensing element surface radius to said narrowed portion radius is less than 1.0 and greater than about 0.4.

23. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card is adapted to be used with a liquid test sample containing a target material to be detected by said sensing element;

wherein said sensing element comprises a sensing element surface;

wherein, during use of said fluidic circuit card, there is a flow of said liquid test sample between said sensor housing means and said sensing element surface;

wherein said fluidic circuit card further comprises mass transfer enhancement means for increasing the rate at which said target material reaches said sensing element surface, to provide at least one of a reduced time for said sensing element to sense said target material and an increased sensitivity of said sensing element to said target material, as compared to if said fluidic circuit card did not comprise said mass transfer enhancement means;

wherein said mass transfer enhancement means comprise a narrowed portion of said sensor housing means; wherein said narrowed portion has a narrowed portion radius; wherein said sensing element surface has a sensing element surface radius; wherein a ratio of said sensing element surface radius to said narrowed portion radius is less than 1.0 and greater than about 0.4 wherein said sensing element surface comprises an elongated, cylindrical, three-dimensional shape; wherein said narrowed portion of said sensor housing means comprises an elongated tube; and wherein said sensing element surface is sized to fit within said elongated tube.

24. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card is adapted to be used with a liquid test sample containing a target material to be detected by said sensing element;

wherein said sensing element comprises a sensing element surface;

wherein, during use of said fluidic circuit card, there is a flow of said liquid test sample between said sensor housing means and said sensing element surface;

wherein said fluidic circuit card further comprises mass transfer enhancement means for increasing the rate at which said target material reaches said sensing element surface, to provide at least one of a reduced time for said sensing element to sense said target material and an increased sensitivity of said sensing element to said target material, as compared to if said fluidic circuit card did not comprise said mass transfer enhancement means;

wherein said fluidic circuit components are selected to permit said flow of said liquid test sample to comprise an alternating, bi-directional flow of said liquid test sample with respect to said sensing element surface; and wherein said mass transfer enhancement means comprise said fluidic circuit components that are so selected.

25. The fluidic circuit card according to claim 21, wherein said sensing element comprises a sensing element cross-sectional shape; wherein said sensor housing means comprises a sensor housing means cross-sectional shape; wherein said sensing element cross-sectional shape and said sensor housing means cross-sectional shape comprise turbulence-inducing, non-corresponding, cross-sectional shapes; and wherein said mass transfer enhancement means comprise said turbulence-inducing, non-corresponding, cross-sectional shapes.

26. The fluidic circuit card according to claim 25, wherein said sensing element cross-sectional shape at least partially comprises a curve; and wherein said sensor housing means cross-sectional shape comprises at least one at least generally straight side.

27. The fluidic circuit card according to claim 21, wherein a mass transfer portion of said sensor housing means comprises at least one of a turbulence-inducing, diverging nozzle shape and a turbulence-inducing, converging nozzle shape; and wherein said mass transfer enhancement means comprise said mass transfer portion of said sensor housing means.

28. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card is adapted to be used with a liquid test sample containing a target material to be detected by said sensing element;

wherein said sensing element comprises a sensing element surface;

wherein, during use of said fluidic circuit card, there is a flow of said liquid test sample between said sensor housing means and said sensing element surface;

wherein said fluidic circuit card further comprises mass transfer enhancement means for increasing the rate at which said target material reaches said sensing element surface, to provide at least one of a reduced time for said sensing element to sense said target material and an increased sensitivity of said sensing element to said target material, as compared to if said fluidic circuit card did not comprise said mass transfer enhancement means;

wherein a mass transfer portion of said sensor housing means comprises at least one of a turbulence-inducing, diverging nozzle shape and a turbulence-inducing, converging nozzle shape; wherein said mass transfer enhancement means comprise said mass transfer portion of said sensor housing means; and wherein at least one of said turbulence-inducing, diverging nozzle shape and said turbulence-inducing, converging nozzle shape comprises at least part of a surface of a cone.

29. The fluidic circuit card according to claim 28, wherein said mass transfer portion of said sensor housing means comprises both said turbulence-inducing, diverging nozzle shape and said turbulence-inducing, converging nozzle shape.

30. The fluidic circuit card according to claim 29, wherein said turbulence-inducing, diverging nozzle shape and said turbulence-inducing, converging nozzle shape merge into each other with a smooth contour.

31. The fluidic circuit card according to claim 21, wherein said sensing element surface follows a sensing element surface path; wherein a mass transfer portion of said sensor housing means follows a mass transfer portion path; wherein said sensing element surface path and said mass transfer portion path are selected to generate a cross-flow component vector in said flow of said liquid test sample; wherein said cross-flow component vector is in a direction that is at a right angle with respect to a corresponding portion of said sensing element surface; and wherein said mass transfer enhancement means comprise said sensing element surface path and said mass transfer portion path.

32. The fluidic circuit card according to claim 31, wherein said sensing element surface path comprises an at least substantially straight path; and wherein said mass transfer portion path comprises an at least substantially sinuous path.

33. A fluidic circuit card comprising:

a main body; and a cover means;

wherein said main body comprises an exterior surface and fluidic circuit components;

wherein said fluidic circuit components comprise a main body input port; a main body output port; a sensor housing means for housing a sensing element; and fluid communication means for providing fluid communication among said main body input port, said main body output port, and said sensor housing means;

wherein at least a portion of each of said fluidic circuit components is defined by said exterior surface of said main body;

wherein said cover means is for covering at least a portion of said sensor housing means and said fluid communication means;

wherein said fluidic circuit card is adapted to be used with a liquid test sample containing a target material to be detected by said sensing element;

wherein said sensing element comprises a sensing element surface;

wherein, during use of said fluidic circuit card, there is a flow of said liquid test sample between said sensor housing means and said sensing element surface;

wherein said fluidic circuit card further comprises mass transfer enhancement means for increasing the rate at which said target material reaches said sensing element surface, to provide at least one of a reduced time for said sensing element to sense said target material and an increased sensitivity of said sensing element to said target material, as compared to if said fluidic circuit card did not comprise said mass transfer enhancement means;

wherein said fluidic circuit card further comprises a deformable portion and a deforming means for selectively deforming said deformable portion, to generate a cross-flow component vector in said flow of said liquid test sample; wherein said cross-flow component vector is in a direction that is at a right angle with respect to a corresponding portion of said sensing element surface; and wherein said mass transfer enhancement means comprise said deformable portion and said deforming means.

34. The fluidic circuit card according to claim 1, wherein said fluidic circuit card is adapted to be used with a liquid test sample containing a target material to be detected by said sensing element; and wherein, during use of said fluidic circuit card, there is contact between said liquid test sample and said sensing element.

35. The fluidic circuit card according to claim 34, wherein said sensing element comprises a material that is impermeable to said liquid test sample.

36. The fluidic circuit card according to claim 34, wherein said sensing element comprises a material that is permeable to said liquid test sample.

37. A method for the recovery of a liquid from a fluidic circuit card containing said liquid; wherein said fluidic circuit card comprises an input port, an output port, and fluid communication means for providing fluid communication between said input port and said output port; and wherein said method comprises the steps of:

constructing said input port, said output port and said fluid communication means to permit alternating, bi-directional flow of said liquid through said input port, said output port and said fluid communication means;

introducing said liquid into said fluid communication means through said input port in a forward direction; and recovering said liquid from said fluid communication means from said input port in a reverse direction.

* * * * *

UNITED STATES PATENT AND TRADEMARK OFFICE
CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

Insert the following claims:

38. The fluidic circuit card according to claim 1, wherein said fluidic circuit card is adapted to be used with a gas and with two different liquids; and wherein said fluidic circuit card further comprises means for permitting a gas bubble to be introduced between said two different liquids when said two different liquids are present in said fluid communication means, to help avoid cross-contamination between said two different liquids.

39. The fluidic circuit card according to claim 21, wherein said fluidic circuit card further comprises an acoustic transducer means for generating acoustic waves; wherein said acoustic waves have a frequency selected to cause said sensing element to vibrate within said flow of said liquid test sample; and wherein said mass transfer enhancement means comprise said acoustic transducer means and said sensing element that is caused to vibrate.

40. The fluidic circuit card according to claim 21, wherein said fluidic circuit card further comprises an asymmetric pressure field generating means for generating an asymmetric pressure field in said flow of said liquid test sample; wherein said asymmetric pressure field generates a cross-flow component in said flow of said liquid test sample; wherein said cross-flow component is in a direction that is at a right angle with respect to a longitudinal axis of said sensing element; and wherein said mass transfer enhancement means comprise said asymmetric pressure field generating means.

41. The fluidic circuit card according to claim 40, wherein said asymmetric pressure field generating means comprise an ultrasonic transducer.

42. The fluidic circuit card according to claim 1, wherein said fluidic circuit card further comprises a light source; and a photodetector; and wherein said light source, said photodetector and said fluid communication means are located with respect to each other to permit said photodetector to receive light from said light source that has passed through at least part of said fluid communication means, to detect the presence of at least one of a liquid, a gas, and a liquid/gas interface in said fluid communication means.

UNITED STATES PATENT AND TRADEMARK OFFICE

CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

43. The fluidic circuit card according to claim 1, wherein said fluidic circuit card further comprises a light source; a photodetector; and a light reflecting means for reflecting light from said light source; and wherein said light source, said photodetector, said light reflecting means, and said fluid communication means are located with respect to each other to permit said photodetector to receive light from said light source that has passed through at least part of said fluid communication means and that has been reflected from said light reflecting means, to detect the presence of at least one of a liquid, a gas, and a liquid/gas interface in said fluid communication means.

44. The fluidic circuit card according to claim 1, wherein said fluidic circuit card further comprises a light source; a photodetector; and a light reflecting means for reflecting light from said light source; wherein said light source, said photodetector, said light reflecting means, and said fluid communication means are located with respect to each other to permit said photodetector to receive light from said light source that has been reflected from said light reflecting means, to detect the presence of at least one of a liquid, a gas, and a liquid/gas interface in said fluid-communication means; and wherein said light reflecting means comprise at least one of said liquid and said gas/liquid interface.

45. The fluidic circuit card according to claim 1, wherein said fluidic circuit card further comprises an encoding window means for encoding said fluidic circuit card; wherein said encoding window means is adapted to be read by a light source/photodetector pair; and wherein said encoding window means is recessed below said exterior surface of said main body to help prevent damage to said encoding window means.

46. The fluidic circuit card according to claim 1, wherein said fluidic circuit card further comprises a light source; a photodetector; and encoding window means for encoding said fluidic circuit card; wherein said light source, said photodetector and said encoding window means are located with respect to each other to permit said photodetector to receive light from said light source that has passed through at least part of said encoding window means when said encoding window means is clear; and wherein when said encoding window means is opaque, said encoding window means blocks the passage of light from said light source to said photodetector.

UNITED STATES PATENT AND TRADEMARK OFFICE
CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

47. The fluidic circuit card according to claim 1, wherein said fluidic circuit card further comprises a light source; a photodetector; a light reflecting means for reflecting light from said light source; and encoding window means for encoding said fluidic circuit card; wherein said light source, said photodetector, said light reflecting means, and said encoding window means are located with respect to each other to permit said photodetector to receive light from said light source that has passed through at least part of said encoding window means when said encoding window means is clear, and that has been reflected from said light reflecting means; and wherein when said encoding window means is opaque, said encoding window means blocks the passage of light from said light source to said photodetector.

48. The fluidic circuit card according to claim 1, wherein said fluidic circuit card further comprises a light source; a photodetector; and encoding window means for encoding said fluidic circuit card; wherein said light source, said photodetector, and said encoding window means are located with respect to each other to permit said photodetector to receive light from said light source that has been reflected from said reflective encoding window means when said encoding window means is reflective; and wherein when said encoding window means is not reflective, said photodetector does not receive light from said light source.

49. The fluidic circuit card according to claim 1, wherein said sensing element comprises an elongated optical sensing fiber; wherein said sensor housing means comprises an elongated said sensor channel for said optical sensing fiber; wherein said fluidic circuit card is adapted to be used with a liquid test sample containing target material to be detected by said sensing element; and wherein, during use of said fluidic circuit card, there is a flow of said liquid test sample between said sensor channel and said optical sensing fiber.

50. The fluidic circuit card according to claim 49, wherein said optical sensing fiber comprises a distal end; wherein said main body further comprises an end recess for said distal end, and a black material located in said end recess; wherein said black material helps to hold said distal end of said optical sensing fiber in said end recess; wherein said black material acts as a light sink for any light reaching said distal end of said optical sensing fiber from a light source; and wherein -said black material helps to accommodate any differential temperature expansion and contraction of said optical sensing fiber and a remaining portion of said main body with respect to each other.

UNITED STATES PATENT AND TRADEMARK OFFICE

CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

51. The fluidic circuit card according to claim 49, wherein said optical sansing fiber comprises an unclad, distal end portion of a clad optical fiber; wherein said main body further comprises a main body edge surface; wherein said sensor housing means further comprises an access portion; wherein said access portion of said sensor housing means is located in said main body edge surface; wherein said access portion permits said unclad, distal end portion of said clad optical fiber to be introduced into said sensor housing means from said main body edge surface; and wherein said access portion helps to provide an unusually compact fluidic card.

52. The fluidic circuit card according to claim 49, wherein said fluidic circuit card further comprises a sensor; wherein said sensor comprises said optical sensing fiber, and a light collecting means; wherein said light collecting means is adapted for collecting an input light from an input light source and delivering said input light to said optical sensing fiber; and wherein said light collecting means is adapted for collecting an output light from said optical sensing fiber and delivering said output light to a detector.

53. The fluidic circuit card according to claim 52, wherein said main body further comprises a main body edge surface; wherein said sensor housing means further comprises an access portion; wherein said access portion of said sensor housing means is located in said main body edge surface; wherein said access portion permits said optical sensing fiber to be introduced into said sensor housing means from said main body edge surface; wherein said access portion houses at least part of said light collecting means; and wherein said access portion helps to provide an unusually compact fluidic card.

54. The fluidic circuit card according to claim 52, wherein said optical sensing fiber and said light collecting means are integrally formed in one piece.

55. The fluidic circuit card according to claim 34, wherein said sensing element comprises a support surface, a layer of antibody immobilized on said support surface, and fluorescent dye-tagged antigen bound to said layer of antibody; and wherein said antibody and said fluorescent dye-tagged antigen are selected to enable said target material to displace said fluorescent dye-tagged antigen from said antibody.

UNITED STATES PATENT AND TRADEMARK OFFICE
CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

55. The fluidic circuit card according to claim 34, wherein said target material comprises target antigen; wherein said sensing element comprises a support surface and a layer of antibody immobilized on said support surface; wherein said antibody is selected to enable said target antigen to bind with said antibody to form bound antibody/target antigen pairs on said support surface; and wherein said bound antibody/target antigen pairs are each adapted to bind a fluorescent dye-tagged antibody.

57. The fluidic circuit card according to claim 34, wherein said target material comprises target antigen; wherein said liquid test sample further comprises a known amount of a fluorescent dye-tagged antigen; wherein said sensing element comprises a support surface and a layer of antibody immobilized on said support surface; and wherein said antibody is selected to enable said target antigen and said fluorescent dye-tagged antigen to bind with said antibody to form, on said support surface, bound antibody/target antigen pairs and bound antibody/fluorescent dye-tagged antigen pairs.

58. The fluidic circuit card according to claim 1, wherein said fluidic circuit card is adapted to be used with a liquid test sample containing target material; wherein said sensing element comprises two optical sensing elements; wherein said two optical sensing elements are separated from each other by a separating portion of said main body; wherein said two optical sensing elements are adapted to receive an input light from a light source and to generate an output light as a function of said target material; and wherein at least said separating portion of said main body comprises a material selected to absorb said input light, to help prevent cross-talk between said two optical sensing elements.

59. A method for increasing the adhesive bonding strength of a plastic with respect to an adhesive material; wherein said method comprises the step of treating a surface of a plastic with a ionized plasma discharge in a low pressure gas; wherein said low pressure is less than about 10 mmHg.

60. The method according to claim 59, wherein said plastic comprises a heat-shrink plastic.

61. The method according to claim 60, wherein said heat-shrink plastic comprises a polyolefin.

UNITED STATES PATENT AND TRADEMARK OFFICE

CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

62. A method for manufacturing a taut valve membrane fox a valve body; wherein said valve body comprises part of a main body; wherein said main body further comprises a main body securing surface that surrounds said valve body; and wherein said method comprises the steps of: providing a sheet of heat-shrink plastic comprising a securing portion and a valve membrane portion; securing said securing portion of said sheet of heat-shrink plastic to said main body securing surface; heating said valve membrane portion of said sheet of heat-shrink plastic until said valve membrane portion of said sheet of heat-shrink plastic forms said taut valve membrane; and ceasing to heat said valve membrane portion of said sheet of heat-shrink plastic.

63. A method for preventing the cross-contamination of a first liquid and a second liquid in a fluidic circuit card; wherein said fluidic circuit card comprises an input port, an output port, and fluid communication means for providing fluid communication between said input port and said output port; and wherein said method comprises the steps of: introducing said first liquid, said second liquid and a gas bubble into said fluid communication means; and locating said gas bubble between said first liquid and said second liquid.

64. A method for increasing the rate at which a target material in a liquid test sample reaches a sensing element surface in a fluidic circuit card; wherein said fluidic circuit card comprises an input port, an output port, and fluid communication means for providing fluid communication between said input port and said output port; wherein said sensing element surface is located in a sensing element portion of said fluid communication means; and wherein said method comprises the step of: providing alternating, bi-directional flow of said liquid test sample with respect to said sensing element surface in said sensing element portion of said fluid communication means.

Signed and Sealed this

Sixteenth Day of October, 2001

*Attest:*

Nicholas P. Godici

NICHOLAS P. GODICI

*Attesting Officer* *Acting Director of the United States Patent and Trademark Office*

UNITED STATES PATENT AND TRADEMARK OFFICE

CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

Insert the following claims:

38. The fluidic circuit card according to claim 1, wherein said fluidic circuit card is adapted to be used with a gas and with two different liquids; and wherein said fluidic circuit card further comprises means for permitting a gas bubble to be introduced between said two different liquids when said two different liquids are present in said fluid communication means, to help avoid cross-contamination between said two different liquids.

39. The fluidic circuit card according to claim 21, wherein said fluidic circuit card further comprises an acoustic transducer means for generating acoustic waves; wherein said acoustic waves have a frequency selected to cause said sensing element to vibrate within said flow of said liquid test sample; and wherein said mass transfer enhancement means comprise said acoustic transducer means and said sensing element that is caused to vibrate.

40. The fluidic circuit card according to claim 21, wherein said fluidic circuit card further comprises an asymmetric pressure field generating means for generating an asymmetric pressure field in said flow of said liquid test sample; wherein said asymmetric pressure field generates a cross-flow component in said flow of said liquid test sample; wherein said cross-flow component is in a direction that is at a right angle with respect to a longitudinal axis of said sensing element; and wherein said mass transfer enhancement means comprise said asymmetric pressure field generating means.

41. The fluidic circuit card according to claim 40, wherein said asymmetric pressure field generating means comprise an ultrasonic transducer.

42. The fluidic circuit card according to claim 1, wherein said fluidic circuit card further comprises a light source; and a photodetector; and wherein said light source, said photodetector and said fluid communication means are located with respect to each other to permit said photodector to receive light from said light source that has passed through at least part of said fluid communication means, to detect the presence of at least one of a liquid, a gas, and a liquid/gas interface in said fluid communication means.

UNITED STATES PATENT AND TRADEMARK OFFICE
CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

43. The fluidic circuit card according to claim 1, wherein said fluidic circuit card further comprises a light source; and photodetector; and a light relecting means for reflecting light from said light source; and wherein said light source, said photodetector, said light reflecting means, and said fluid communication means are located with respect to each other to permit said photodetector to receive light from said light source that has passed through at least part of said fluid communication means and that has been reflected from said light reflecting means, to detect the presence of at least one of a liquid, a gas, and a liquid/gas interface in said fluid communication means.

44. The fluidic circuit card according to claim 1, wherein said fluidic circuit card further comprises a light source; a photodetector; and a light reflecting means for reflecting light from said light source; wherein said light source, said photodetector, said light reflecting means, and said fluid communication means are located with respect to each other to permit said photodetector to receive light from said light source that has been reflected from said light reflecting means, to detect the presence of at least one of a liquid, a gas, and a liquid/gas interface in said fluid-communication means; and wherein said light reflecting means comprise at least one of said liquid and said gas/liquid interface.

45. The fluidic circuit card according to claim 1, wherein said fluidic circuit card further comprises an encoding window means for encoding said fluidic circuit card; wherein said encoding window means is adapted to be read by a light source/photodetector pair; and wherein said encoding window means is recessed below said exterior surface of said main body to help prevent damage to said encoding window means.

46. The fluidic circuit card according to claim 1, wherein said fluidic circuit card further comprises a light source; a photodetector; and encoding window means for encoding said fluidic circuit card; wherein said light source, said photodetector and said encoding window means are located with respect to each other to permit said photodetector to receive light from said light source that has passed through at least part of said encoding window means when said encoding window means is clear; and wherein when said encoding window means is opaque, said encoding window means blocks the passage of light from said light source to said photodetector.

UNITED STATES PATENT AND TRADEMARK OFFICE
CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

47. The fluidic circuit card according to claim 1, wherein said fluidic circuit card further comprises a light source; a photodetector; a light reflecting means for reflecting light from said light source; and encoding window means for encoding said fluidic circuit card; wherein said light source, said photodetector, said light reflecting means, and said encoding window means are located with respect to each other to permit said photodetector to receive light from said light source that has passed through at least part of said encoding window means when said encoding window means is clear, and that has been reflected from said light reflecting means; and wherein when said encoding window means is opaque, said encoding window means blocks the passage of light from said light source to said photodetector.

48. The fluidic circuit card according to claim 1, wherein said fluidic circuit card further comprises a light source; a photodetector; and encoding window means for encoding said fluidic circuit card; wherein said light source, said photodetector, and said encoding window means are located with respect to each other to permit said photodetector to receive light from said light source that has been reflected from said reflective encoding window means when said encoding window means is reflective; and wherein when said encoding window means is not reflective, said photodetector does not receive light from said light source.

49. The fluidic circuit card according to claim 1, wherein said sensing element comprises an elongated optical sensing fiber; wherein said sensor housing means comprises an elongated said sensor channel for said optical sensing fiber; wherein said fluidic circuit card is adapted to be used with a liquid test sample containing target material to be detected by said sensing element; and wherein, during use of said fluidic circuit card, there is a flow of said liquid test sample between said sensor channel and said optical sensing fiber.

50. The fluidic circuit card according to claim 49, wherein said optical sensing fiber comprises a distal end; wherein said main body further comprises an end recess for said distal end, and a black material located in said end recess; wherein said black material helps to hold said distal end of said optical sensing fiber in said end recess; wherein said black material acts as a light sink for any light reaching said distal end of said optical sensing fiber from a light source; and wherein -said black material helps to accommodate any differential temperature expansion and contraction of said optical sensing fiber and a remaining portion of said main body with respect to each other.

UNITED STATES PATENT AND TRADEMARK OFFICE
CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

51. The fluidic circuit card according to claim 49, wherein said optical sansing fiber comprises an unclad, distal end portion of a clad optical fiber; wherein said main body further comprises a main body edge surface; wherein said sensor housing means further comprises an access portion; wherein said access portion of said sensor housing means is located in said main body edge surface; wherein said access portion permits said unclad, distal end portion of said clad optical fiber to be introduced into said sensor housing means from said main body edge surface; and wherein said access portion helps to provide an unusually compact fluidic card.

52. The fluidic circuit card according to claim 49, wherein said fluidic circuit card further comprises a sensor; wherein said sensor comprises said optical sensing fiber, and a light collecting means; wherein said light collecting means is adapted for collecting an input light from an input light source and delivering said input light to said optical sensing fiber; and wherein said light collecting means is adapted for collecting an output light from said optical sensing fiber and delivering said output light to a detector.

53. The fluidic circuit card according to claim 52, wherein said main body further comprises a main body edge surface; wherein said sensor housing means further comprises an access portion; wherein said access portion of said sensor housing means is located in said main body edge surface; wherein said access portion permits said optical sensing fiber to be introduced into said sensor housing means from said main body edge surface; wherein said access portion houses at least part of said light collecting means; and wherein said access portion helps to provide an unusually compact fluidic card.

54. The fluidic circuit card according to claim 52, wherein said optical sensing fiber and said light collecting means are integrally formed in one piece.

55. The fluidic circuit card according to claim 34, wherein said sensing element comprises a support surface, a layer of antibody immobilized on said support surface, and fluorescent dye-tagged antigen bound to said layer of antibody; and wherein said antibody and said fluorescent dye-tagged antigen are selected to enable said target material to displace said fluorescent dye-tagged antigen from said antibody.

56. The fluidic circuit card according to claim 34, wherein said target material comprises target antigen; wherein said sensing element comprises a support surface and a layer of antibody immobilized on said support surface; wherein said antibody is selected to enable said target antigen to bind with said antibody to form bound antibody/ target antigen pairs on said support surface; and wherein said bound antibody/target antigen pairs are each adapted to bind a fluorescent dye-tagged antibody.

UNITED STATES PATENT AND TRADEMARK OFFICE
CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

57. The fluidic circuit card according to claim 34, wherein said target material comprises target antigen; wherein said liquid test sample further comprises a known amount of a fluorescent dye-tagged antigen; wherein said sensing element comprises a support surface and a layer of antibody immobilized on said support surface; and wherein said antibody is selected to enable said target antigen and said fluorescent dye-tagged antigen to bind with said antibody to form, on said support surface, bound antibody/target antigen pairs and bound antibody/fluorescent dye-tagged antigen pairs.

58. The fluidic circuit card according to claim 1, wherein said fluidic circuit card is adapted to be used with a liquid test sample containing target material; wherein said sensing element comprises two optical sensing elements; wherein said two optical sensing elements are separated from each other by a separating portion of said main body; wherein said two optical sensing elements are adapted to receive an input light from a light source and to generate an output light as a function of said target material; and wherein at least said separating portion of said main body comprises a material selected to absorb said input light, to help prevent cross-talk between said two optical sensing elements.

59. A method for increasing the adhesive bonding strength of a plastic with respect to an adhesive material; wherein said method comprises the step of treating a surface of a plastic with a ionized plasma discharge in a low pressure gas; wherein said low pressure is less than about 10 mmHg.

60. The method according to claim 59, wherein said plastic comprises a heat-shrink plastic.

61. The method according to claim 60, wherein said heat-shrink plastic comprises a polyolefin.

62. A method for manufacturing a taut valve membrane fox a valve body; wherein said valve body comprises part of a main body; wherein said main body further comprises a main body securing surface that surrounds said valve body; and wherein said method comprises the steps of: providing a sheet of heat-shrink plastic comprising a securing portion and a valve membrane portion; securing said securing portion of said sheet of heat-shrink plastic to said main body securing surface; heating said valve membrane portion of said sheet of heat-shrink plastic until said valve membrane portion of said sheet of heat-shrink plastic forms said taut valve membrane; and ceasing to heat said valve membrane portion of said sheet of heat-shrink plastic.

UNITED STATES PATENT AND TRADEMARK OFFICE

CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

63. A method for preventing the cross-contamination of a first liquid and a second liquid in a fluidic circuit card; wherein said fluidic circuit card comprises an input port, an output port, and fluid communication means for providing fluid communication between said input port and said output port; and wherein said method comprises the steps of: introducing said first liquid, said second liquid and a gas bubble into said fluid communication means; and locating said gas bubble between said first liquid and said second liquid.

64. A method for increasing the rate at which a target material in a liquid test sample reaches a sensing element surface in a fluidic circuit card; wherein said fluidic circuit card comprises an input port, an output port, and fluid communication means for providing fluid communication between said input port and said output port; wherein said sensing element surface is located in a sensing element portion of said fluid communication means; and wherein said method comprises the step of: providing alternating, bi-directional flow of said liquid test sample with respect to said sensing element surface in said sensing element portion of said fluid communication means.

This certificate supersedes Certificate of Correction issued October 16, 2001

Signed and Sealed this

Twenty-ninth Day of January, 2002

*Attest:*

JAMES E. ROGAN

*Attesting Officer* *Director of the United States Patent and Trademark Office*

UNITED STATES PATENT AND TRADEMARK OFFICE

CERTIFICATE OF CORRECTION

PATENT NO. : 6,082,185 
DATED : July 4, 2000
INVENTOR(S) : Elric W. Saaski

It is certified that error appears in the above-identified patent and that said Letters Patent is hereby corrected as shown below:

Insert the following claims:

38. The fluidic circuit card according to claim 1, wherein said fluidic circuit card is adapted to be used with a gas and with two different liquids; and wherein said fluidic circuit card further comprises means for permitting a gas bubble to be introduced between said two different liquids when said two different liquids are present in said fluid communication means, to help avoid cross-contamination between said two different liquids.

39. The fluidic circuit card according to claim 21, wherein said fluidic circuit card further comprises an acoustic transducer means for generating acoustic waves; wherein said acoustic waves have a frequency selected to cause said sensing element to vibrate within said flow of said liquid test sample; and wherein said mass transfer enhancement means comprise said acoustic transducer means and said sensing element that is caused to vibrate.

40. The fluidic circuit card according to claim 21, wherein said fluidic circuit card further comprises an asymmetric pressure field generating means for generating an asymmetric pressure field in said flow of said liquid test sample; wherein said asymmetric pressure field generates a cross-flow component in said flow of said liquid test sample; wherein said cross-flow component is in a direction that is at a right angle with respect to a longitudinal axis of said sensing element; and wherein said mass transfer enhancement means comprise said asymmetric pressure field generating means.

41. The fluidic circuit card according to claim 40, wherein said asymmetric pressure field generating means comprise an ultrasonic transducer.

42. The fluidic circuit card according to claim 1, wherein said fluidic circuit card further comprises a light source; and a photodetector; and wherein said light source, said photodetector and said fluid communication means are located with respect to each other to permit said photodector to receive light from said light source that has passed through at least part of said fluid communication means, to detect the presence of at least one of a liquid, a gas, and a liquid/gas interface in said fluid communication means.

UNITED STATES PATENT AND TRADEMARK OFFICE
CERTIFICATE OF CORRECTION

PATENT NO. : 6,082,185

DATED : July 4, 2000
INVENTOR(S) : Elric W. Saaski

It is certified that error appears in the above-identified patent and that said Letters Patent is hereby corrected as shown below:

43. The fluidic circuit card according to claim 1, wherein said fluidic circuit card further comprises a light source; and photodetector; and a light relecting means for reflecting light from said light source; and wherein said light source, said photodetector, said light reflecting means, and said fluid communication means are located with respect to each other to permit said photodetector to receive light from said light source that has passed through at least part of said fluid communication means and that has been reflected from said light reflecting means, to detect the presence of at least one of a liquid, a gas, and a liquid/gas interface in said fluid communication means.

44. The fluidic circuit card according to claim 1, wherein said fluidic circuit card further comprises a light source; a photodetector; and a light reflecting means for reflecting light from said light source; wherein said light source, said photodetector, said light reflecting means, and said fluid communication means are located with respect to each other to permit said photodetector to receive light from said light source that has been reflected from said light reflecting means, to detect the presence of at least one of a liquid, a gas, and a liquid/gas interface in said fluid-communication means; and wherein said light reflecting means comprise at least one of said liquid and said gas/liquid interface.

45. The fluidic circuit card according to claim 1, wherein said fluidic circuit card further comprises an encoding window means for encoding said fluidic circuit card; wherein said encoding window means is adapted to be read by a light source/photodetector pair; and wherein said encoding window means is recessed below said exterior surface of said main body to help prevent damage to said encoding window means.

46. The fluidic circuit card according to claim 1, wherein said fluidic circuit card further comprises a light source; a photodetector; and encoding window means for encoding said fluidic circuit card; wherein said light source, said photodetector and said encoding window means are located with respect to each other to permit said photodetector to receive light from said light source that has passed through at least part of said encoding window means when said encoding window means is clear; and wherein when said encoding window means is opaque, said encoding window means blocks the passage of light from said light source to said photodetector.

UNITED STATES PATENT AND TRADEMARK OFFICE

CERTIFICATE OF CORRECTION

PATENT NO. : 6,082,185 
DATED : July 4, 2000
INVENTOR(S) : Elric W. Saaski

It is certified that error appears in the above-identified patent and that said Letters Patent is hereby corrected as shown below:

47. The fluidic circuit card according to claim 1, wherein said fluidic circuit card further comprises a light source; a photodetector; a light reflecting means for reflecting light from said light source; and encoding window means for encoding said fluidic circuit card; wherein said light source, said photodetector, said light reflecting means, and said encoding window means are located with respect to each other to permit said photodetector to receive light from said light source that has passed through at least part of said encoding window means when said encoding window means is clear, and that has been reflected from said light reflecting means; and wherein when said encoding window means is opaque, said encoding window means blocks the passage of light from said light source to said photodetector.

48. The fluidic circuit card according to claim 1, wherein said fluidic circuit card further comprises a light source; a photodetector; and encoding window means for encoding said fluidic circuit card; wherein said light source, said photodetector, and said encoding window means are located with respect to each other to permit said photodetector to receive light from said light source that has been reflected from said reflective encoding window means when said encoding window means is reflective; and wherein when said encoding window means is not reflective, said photodetector does not receive light from said light source.

49. The fluidic circuit card according to claim 1, wherein said sensing element comprises an elongated optical sensing fiber; wherein said sensor housing means comprises an elongated said sensor channel for said optical sensing fiber; wherein said fluidic circuit card is adapted to be used with a liquid test sample containing target material to be detected by said sensing element; and wherein, during use of said fluidic circuit card, there is a flow of said liquid test sample between said sensor channel and said optical sensing fiber.

50. The fluidic circuit card according to claim 49, wherein said optical sensing fiber comprises a distal end; wherein said main body further comprises an end recess for said distal end, and a black material located in said end recess; wherein said black material helps to hold said distal end of said optical sensing fiber in said end recess; wherein said black material acts as a light sink for any light reaching said distal end of said optical sensing fiber from a light source; and wherein -said black material helps to accommodate any differential temperature expansion and contraction of said optical sensing fiber and a remaining portion of said main body with respect to each other.

UNITED STATES PATENT AND TRADEMARK OFFICE

CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

51. The fluidic circuit card according to claim 49, wherein said optical sansing fiber comprises an unclad, distal end portion of a clad optical fiber; wherein said main body further comprises a main body edge surface; wherein said sensor housing means further comprises an access portion; wherein said access portion of said sensor housing means is located in said main body edge surface; wherein said access portion permits said unclad, distal end portion of said clad optical fiber to be introduced into said sensor housing means from said main body edge surface; and wherein said access portion helps to provide an unusually compact fluidic card.

52. The fluidic circuit card according to claim 49, wherein said fluidic circuit card further comprises a sensor; wherein said sensor comprises said optical sensing fiber, and a light collecting means; wherein said light collecting means is adapted for collecting an input light from an input light source and delivering said input light to said optical sensing fiber; and wherein said light collecting means is adapted for collecting an output light from said optical sensing fiber and delivering said output light to a detector.

53. The fluidic circuit card according to claim 52, wherein said main body further comprises a main body edge surface; wherein said sensor housing means further comprises an access portion; wherein said access portion of said sensor housing means is located in said main body edge surface; wherein said access portion permits said optical sensing fiber to be introduced into said sensor housing means from said main body edge surface; wherein said access portion houses at least part of said light collecting means; and wherein said access portion helps to provide an unusually compact fluidic card.

54. The fluidic circuit card according to claim 52, wherein said optical sensing fiber and said light collecting means are integrally formed in one piece.

55. The fluidic circuit card according to claim 34, wherein said sensing element comprises a support surface, a layer of antibody immobilized on said support surface, and fluorescent dye-tagged antigen bound to said layer of antibody; and wherein said antibody and said fluorescent dye-tagged antigen are selected to enable said target material to displace said fluorescent dye-tagged antigen from said antibody.

56. The fluidic circuit card according to claim 34, wherein said target material comprises target antigen; wherein said sensing element comprises a support surface and a layer of antibody immobilized on said support surface; wherein said antibody is selected to enable said target antigen to bind with said antibody to form bound antibody/target antigen pairs on said support surface; and wherein said bound antibody/target antigen pairs are each adapted to bind a fluorescent dye-tagged antibody.

UNITED STATES PATENT AND TRADEMARK OFFICE

CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

57. The fluidic circuit card according to claim 34, wherein said target material comprises target antigen; wherein said liquid test sample further comprises a known amount of a fluorescent dye-tagged antigen; wherein said sensing element comprises a support surface and a layer of antibody immobilized on said support surface; and wherein said antibody is selected to enable said target antigen and said fluorescent dye-tagged antigen to bind with said antibody to form, on said support surface, bound antibody/target antigen pairs and bound antibody/fluorescent dye-tagged antigen pairs.

58. The fluidic circuit card according to claim 1, wherein said fluidic circuit card is adapted to be used with a liquid test sample containing target material; wherein said sensing element comprises two optical sensing elements; wherein said two optical sensing elements are separated from each other by a separating portion of said main body; wherein said two optical sensing elements are adapted to receive an input light from a light source and to generate an output light as a function of said target material; and wherein at least said separating portion of said main body comprises a material selected to absorb said input light, to help prevent cross-talk between said two optical sensing elements.

59. A method for increasing the adhesive bonding strength of a plastic with respect to an adhesive material; wherein said method comprises the step of treating a surface of a plastic with a ionized plasma discharge in a low pressure gas; wherein said low pressure is less than about 10 mmHg.

60. The method according to claim 59, wherein said plastic comprises a heat-shrink plastic.

61. The method according to claim 60, wherein said heat-shrink plastic comprises a polyolefin.

62. A method for manufacturing a taut valve membrane fox a valve body; wherein said valve body comprises part of a main body; wherein said main body further comprises a main body securing surface that surrounds said valve body; and wherein said method comprises the steps of: providing a sheet of heat-shrink plastic comprising a securing portion and a valve membrane portion; securing said securing portion of said sheet of heat-shrink plastic to said main body securing surface; heating said valve membrane portion of said sheet of heat-shrink plastic until said valve membrane portion of said sheet of heat-shrink plastic forms said taut valve membrane; and ceasing to heat said valve membrane portion of said sheet of heat-shrink plastic.

UNITED STATES PATENT AND TRADEMARK OFFICE

CERTIFICATE OF CORRECTION

PATENT NO. : 6,082,185 
DATED : July 4, 2000
INVENTOR(S) : Elric W. Saaski

It is certified that error appears in the above-identified patent and that said Letters Patent is hereby corrected as shown below:

63. A method for preventing the cross-contamination of a first liquid and a second liquid in a fluidic circuit card; wherein said fluidic circuit card comprises an input port, an output port, and fluid communication means for providing fluid communication between said input port and said output port; and wherein said method comprises the steps of: introducing said first liquid, said second liquid and a gas bubble into said fluid communication means; and locating said gas bubble between said first liquid and said second liquid.

64. A method for increasing the rate at which a target material in a liquid test sample reaches a sensing element surface in a fluidic circuit card; wherein said fluidic circuit card comprises an input port, an output port, and fluid communication means for providing fluid communication between said input port and said output port; wherein said sensing element surface is located in a sensing element portion of said fluid communication means; and wherein said method comprises the step of: providing alternating, bi-directional flow of said liquid test sample with respect to said sensing element surface in said sensing element portion of said fluid communication means.

This certificate supersedes Certificate of Correction issued October 16, 2001

Signed and Sealed this

Sixth Day of August, 2002

*Attest:*

JAMES E. ROGAN

*Attesting Officer* *Director of the United States Patent and Trademark Office*

UNITED STATES PATENT AND TRADEMARK OFFICE

CERTIFICATE OF CORRECTION

PATENT NO. : 6,082,185
DATED : July 4, 2000
INVENTOR(S) : Elric W. Saaski

It is certified that error appears in the above-identified patent and that said Letters Patent is hereby corrected as shown below:

Column 1,
Line 2, the following two sentences should be inserted:

-- This invention was made with Government support under Grant/Contract Number N00014-95-C-2251 awared by the Department of the Navy. The Government has certain rights in the invention. --

Signed and Sealed this

Twenty-fourth Day of December, 2002

JAMES E. ROGAN
*Director of the United States Patent and Trademark Office*